United States Patent
Messerly et al.

(10) Patent No.: US 10,828,056 B2
(45) Date of Patent: Nov. 10, 2020

(54) ULTRASONIC TRANSDUCER TO WAVEGUIDE ACOUSTIC COUPLING, CONNECTIONS, AND CONFIGURATIONS

(71) Applicant: Ethicon LLC, Guaynabo, PR (US)

(72) Inventors: Jeffrey D. Messerly, Cincinnati, OH (US); Benjamin D. Dickerson, Cincinnati, OH (US); Rafael J. Ruiz Ortiz, Mason, OH (US); Ryan M. Asher, Cincinnati, OH (US); Joseph D. Dennis, Wyoming, OH (US); Brian D. Black, Loveland, OH (US); Craig T. Davis, Cincinnati, OH (US); Mark E. Tebbe, Lebanon, OH (US); Ion V. Nicolaescu, Cincinnati, OH (US); Frederick Estera, Cincinnati, OH (US); William A. Olson, Lebanon, OH (US); Amelia Pierce, Cincinnati, OH (US); James Wilson, Cincinnati, OH (US); William D. Dannaher, Cincinnati, OH (US); Fajian Zhang, Mason, OH (US); Foster B. Stulen, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 195 days.

(21) Appl. No.: 15/679,959

(22) Filed: Aug. 17, 2017

(65) Prior Publication Data
US 2018/0056095 A1 Mar. 1, 2018

Related U.S. Application Data

(60) Provisional application No. 62/379,550, filed on Aug. 25, 2016.

(51) Int. Cl.
*A61N 7/02* (2006.01)
*A61B 17/32* (2006.01)
(Continued)

(52) U.S. Cl.
CPC ............ *A61B 17/320068* (2013.01); *A61B 17/00234* (2013.01); *A61N 7/02* (2013.01);
(Continued)

(58) Field of Classification Search
CPC combination set(s) only.
See application file for complete search history.

(56) References Cited

U.S. PATENT DOCUMENTS 5,213,103 A 5/1993 Martin et al.
5,322,055 A 6/1994 Davison et al.
(Continued)

FOREIGN PATENT DOCUMENTS

GB 2318298 A 4/1998
JP H04161078 A 6/1992
(Continued)

OTHER PUBLICATIONS https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
(Continued)

*Primary Examiner* — Bryan P Gordon

(57) ABSTRACT

Various ultrasonic instruments are disclosed. The ultrasonic instruments include an ultrasonic waveguide acoustically coupled to an ultrasonic transducer. Several techniques for acoustically coupling the ultrasonic transducer to the ultrasonic waveguide are disclosed.

10 Claims, 34 Drawing Sheets

(51) Int. Cl.
  *H01L 41/053* (2006.01)
  *H01L 41/083* (2006.01)
  *H01L 41/09* (2006.01)
  *A61B 17/00* (2006.01)
  *B29C 65/48* (2006.01)
  *A61B 17/22* (2006.01)
  *A61B 17/29* (2006.01)
  *B29L 31/00* (2006.01)
  *A61B 17/16* (2006.01)
  *A61B 18/00* (2006.01)

(52) U.S. Cl.
  CPC ...... *B29C 65/4805* (2013.01); *H01L 41/0536* (2013.01); *H01L 41/083* (2013.01); *H01L 41/0835* (2013.01); *H01L 41/0986* (2013.01); *A61B 17/1628* (2013.01); *A61B 2017/00017* (2013.01); *A61B 2017/0088* (2013.01); *A61B 2017/00402* (2013.01); *A61B 2017/00477* (2013.01); *A61B 2017/00526* (2013.01); *A61B 2017/22027* (2013.01); *A61B 2017/294* (2013.01); *A61B 2017/32007* (2017.08); *A61B 2017/320074* (2017.08); *A61B 2017/320082* (2017.08); *A61B 2017/320088* (2013.01); *A61B 2017/320089* (2017.08); *A61B 2017/320098* (2017.08); *A61B 2018/00565* (2013.01); *A61B 2018/00589* (2013.01); *A61B 2018/00595* (2013.01); *B29L 2031/7546* (2013.01)

(56) References Cited

U.S. PATENT DOCUMENTS

| | | |
|---|---|---|
| 5,695,510 A * | 12/1997 | Hood ............ A61B 17/320068 606/169 |
| 5,800,449 A | 9/1998 | Wales |
| 5,954,736 A | 9/1999 | Bishop et al. |
| 6,278,218 B1 | 8/2001 | Madan et al. |
| 6,283,981 B1 | 9/2001 | Beaupre |
| 6,309,400 B2 | 10/2001 | Beaupre |
| 6,325,811 B1 | 12/2001 | Messerly |
| 6,436,115 B1 | 8/2002 | Beaupre |
| 6,561,983 B2 | 5/2003 | Cronin et al. |
| 7,282,836 B2 | 10/2007 | Kwon et al. |
| 7,449,004 B2 | 11/2008 | Yamada et al. |
| 7,533,830 B1 * | 5/2009 | Rose ............... H01L 41/0835 239/4 |
| 7,578,166 B2 | 8/2009 | Ethridge et al. |
| 7,879,035 B2 | 2/2011 | Garrison et al. |
| 8,246,642 B2 | 8/2012 | Houser et al. |
| 8,319,400 B2 | 11/2012 | Houser et al. |
| 8,334,635 B2 | 12/2012 | Voegele et al. |
| 8,734,476 B2 | 5/2014 | Rhee et al. |
| 9,084,878 B2 | 7/2015 | Kawaguchi et al. |
| 9,114,245 B2 | 8/2015 | Dietz et al. |
| 9,510,906 B2 | 12/2016 | Boudreaux et al. |
| 9,700,339 B2 | 7/2017 | Nield |
| 9,737,735 B2 | 8/2017 | Dietz et al. |
| 9,801,648 B2 | 10/2017 | Houser et al. |
| 9,839,796 B2 | 12/2017 | Sawada |
| 9,901,339 B2 | 2/2018 | Farascioni |
| 10,188,385 B2 | 1/2019 | Kerr et al. |
| 10,368,892 B2 | 8/2019 | Stulen et al. |
| 10,420,580 B2 | 9/2019 | Messerly et al. |
| 2007/0130771 A1 | 6/2007 | Ehlert et al. |
| 2007/0132343 A1* | 6/2007 | Kwon ............... H01L 41/083 310/366 |
| 2007/0191713 A1 | 8/2007 | Eichmann et al. |
| 2008/0214967 A1 | 9/2008 | Aranyi et al. |
| 2009/0069830 A1 | 3/2009 | Mulvihill et al. |
| 2009/0178466 A1* | 7/2009 | Ethridge ............ G01N 29/07 73/1.86 |
| 2010/0063528 A1 | 3/2010 | Beaupre |
| 2011/0291526 A1* | 12/2011 | Abramovich ........... F03G 7/08 310/339 |
| 2012/0059289 A1 | 3/2012 | Nield et al. |
| 2014/0081299 A1 | 3/2014 | Dietz et al. |
| 2014/0135663 A1 | 5/2014 | Funakubo et al. |
| 2014/0323926 A1 | 10/2014 | Akagane |
| 2015/0011889 A1 | 1/2015 | Lee |
| 2015/0289854 A1 | 10/2015 | Cho et al. |
| 2017/0036044 A1* | 2/2017 | Ito ..................... H01L 41/083 |
| 2018/0055529 A1 | 3/2018 | Messerly et al. |
| 2018/0055531 A1 | 3/2018 | Messerly et al. |
| 2018/0055532 A1 | 3/2018 | Messerly et al. |
| 2018/0078268 A1 | 3/2018 | Messerly et al. |

FOREIGN PATENT DOCUMENTS

| | | |
|---|---|---|
| JP | 2005094552 A | 4/2005 |
| JP | 2005253674 A | 9/2005 |
| JP | 2009297352 A | 12/2009 |
| WO | WO-2012066983 A1 | 5/2012 |
| WO | WO-2013048963 A2 | 4/2013 |

OTHER PUBLICATIONS

Douglas, S.C. "Introduction to Adaptive Filter". Digital Signal Processing Handbook. Ed. Vijay K. Madisetti and Douglas B. Williams. Boca Raton: CRC Press LLC, 1999.

Leonard I. Malis, M.D., "The Value of Irrigation During Bipolar Coagulation," 1989.

Covidien Brochure, The LigaSure Precise™ Instrument, dated Mar. 2011 (2 pages).

Glaser and Subak-Sharpe,Integrated Circuit Engineering, Addison-Wesley Publishing, Reading, MA (1979). (book—not attached).

Jang, J. et al. "Neuro-fuzzy and Soft Computing." Prentice Hall, 1997, pp. 13-89, 199-293, 335-393, 453-496, 535-549.

Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.

Mitsui Chemicals Names DuPont™ Vespel® Business as Exclusive U.S., European Distributor of AUTUM® Thermoplastic Polyimide Resin, Feb. 24, 2003; http://www2.dupont.com/Vespel/en_US/news_events/article20030224.html.

Sadiq Muhammad et al: "High-performance planar ultrasonic tool based on d31-mode piezocrystal", IEEE Transactions on Ultrasonics, Ferroelectrics and Frequency Control, IEEE, US, vol. 62, No. 3, Mar. 30, 2015 (Mar. 30, 2015), pp. 428-438, XP011574640, ISSN: 0885-3010, DOI: 10.1109/TUFFC.2014.006437.

* cited by examiner

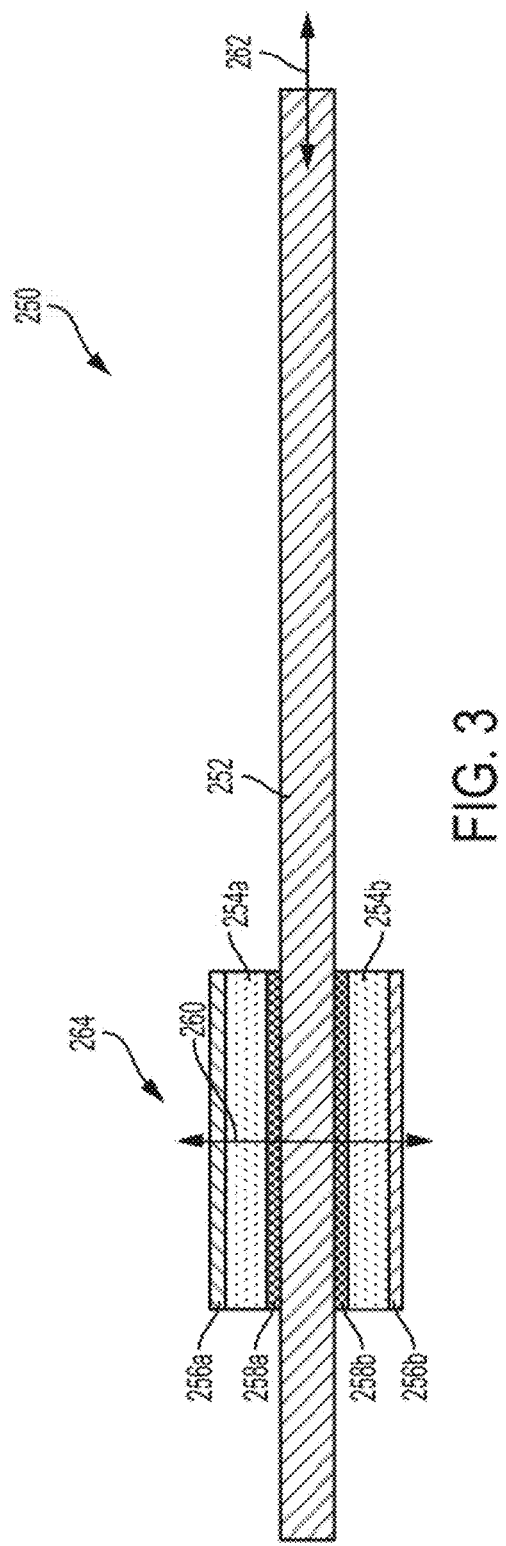

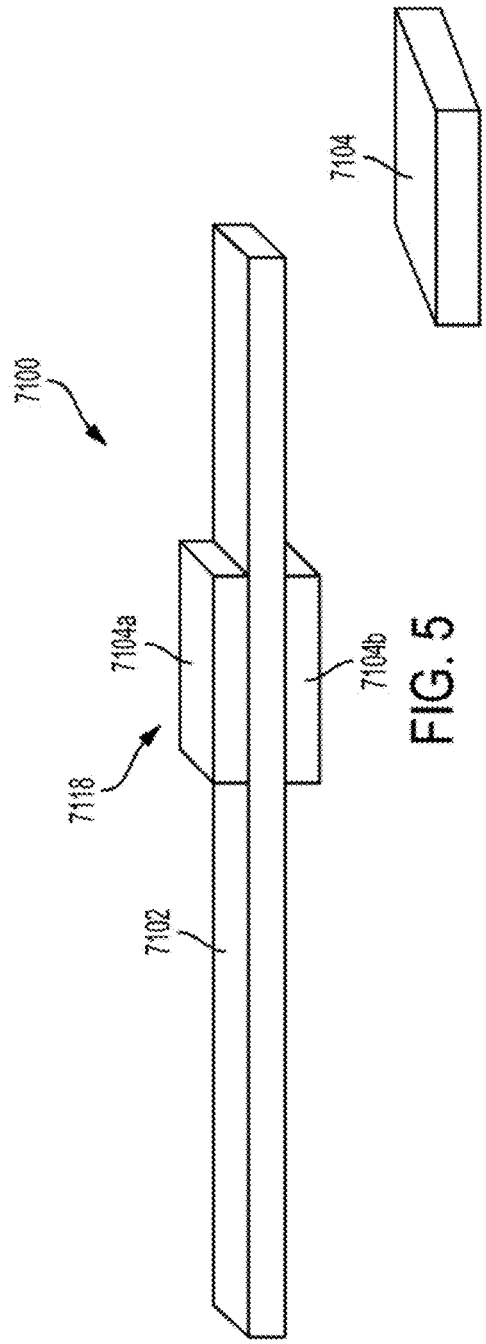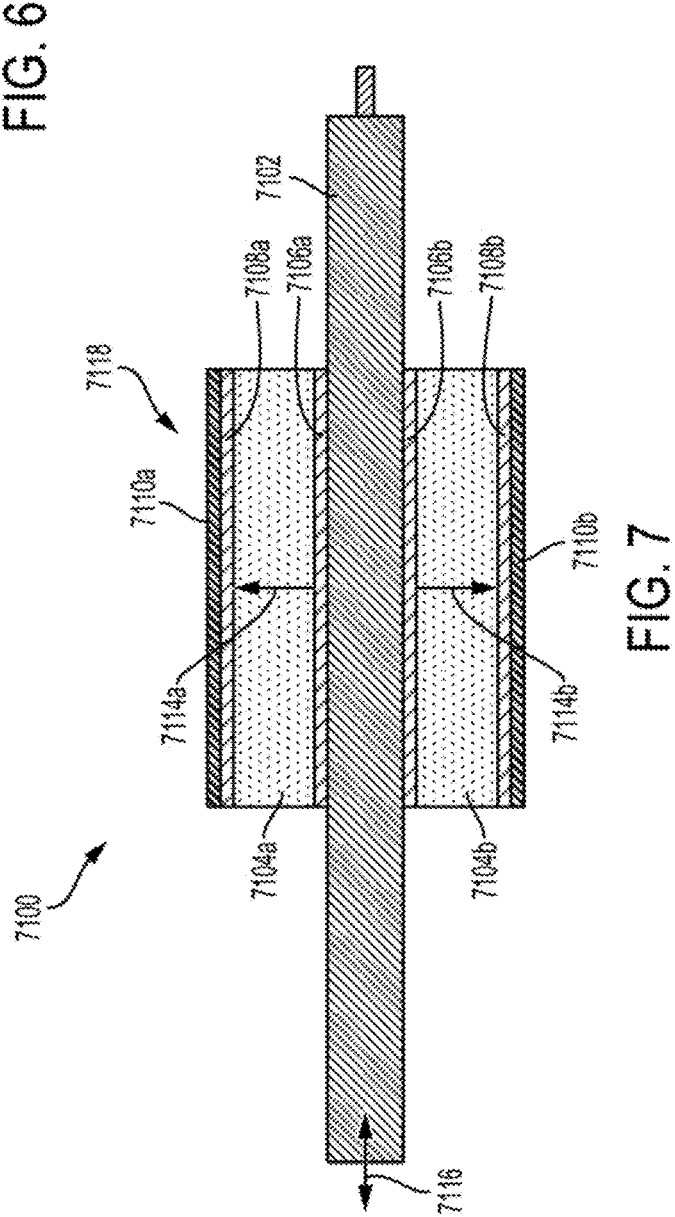

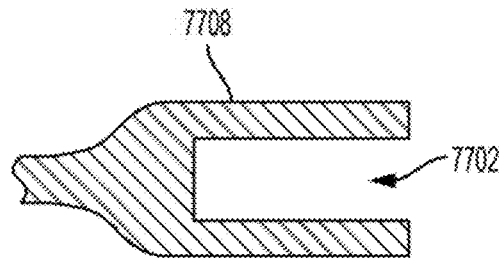
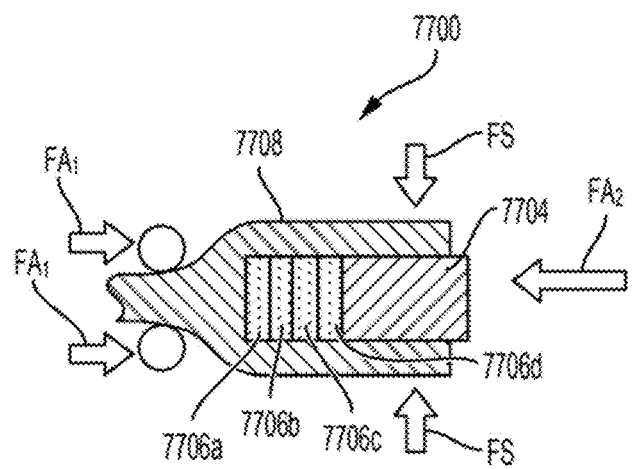
FIG. 19A
FIG. 19B
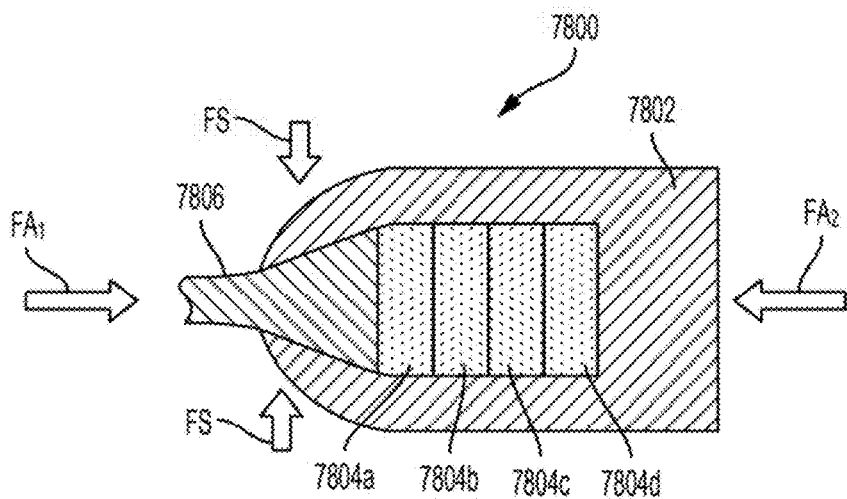
FIG. 20
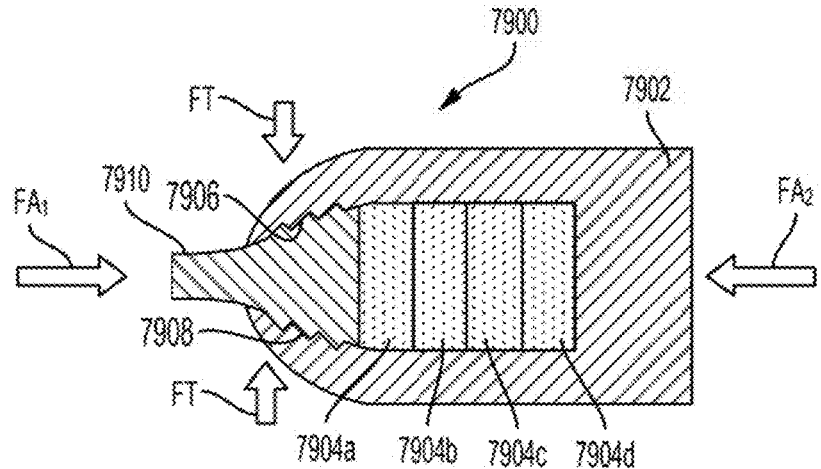
FIG. 21

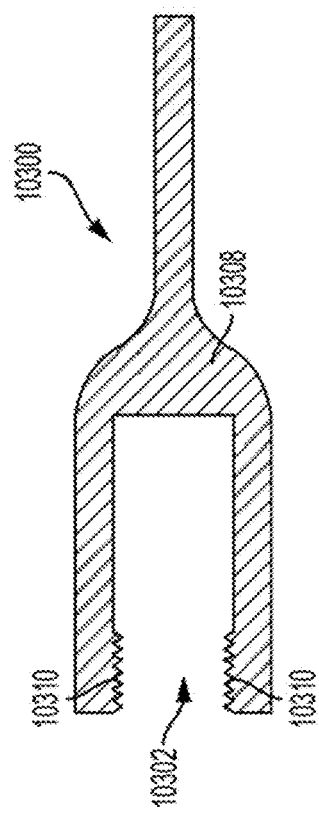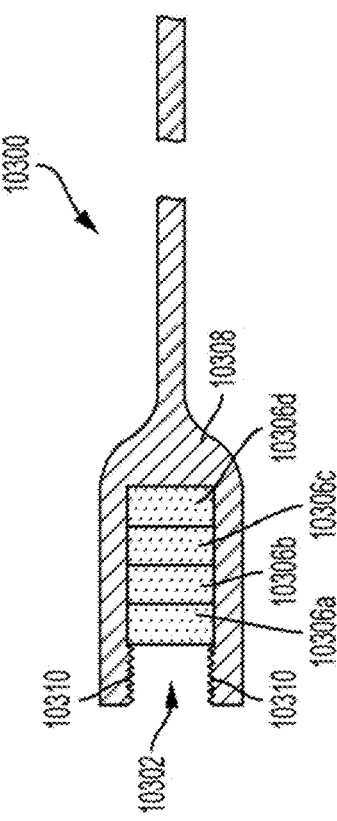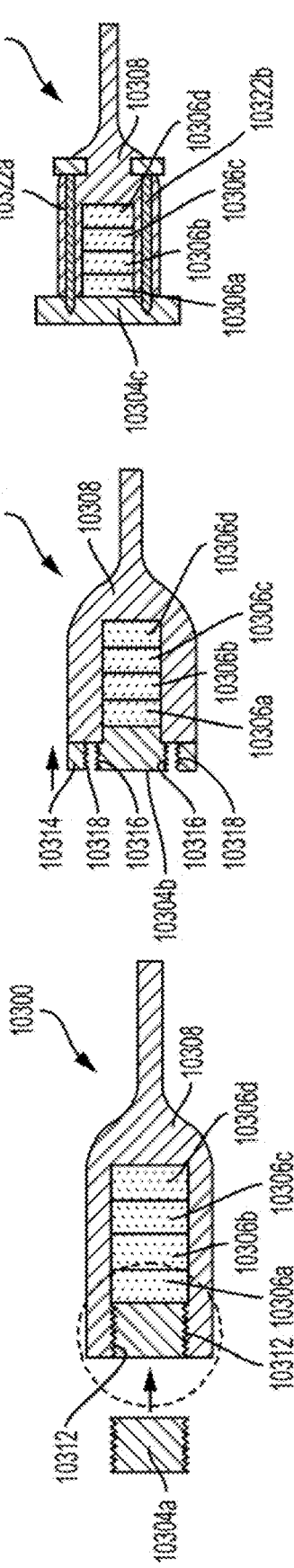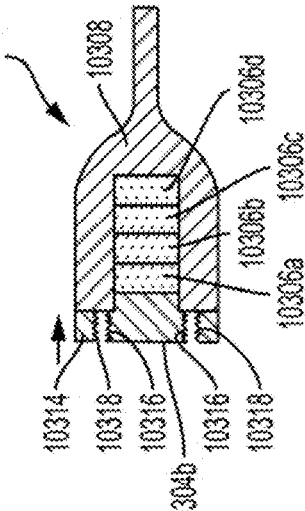

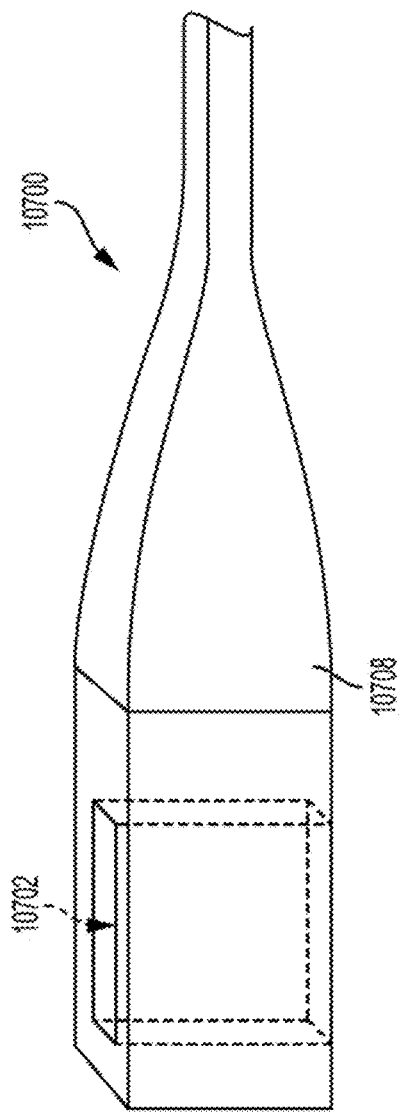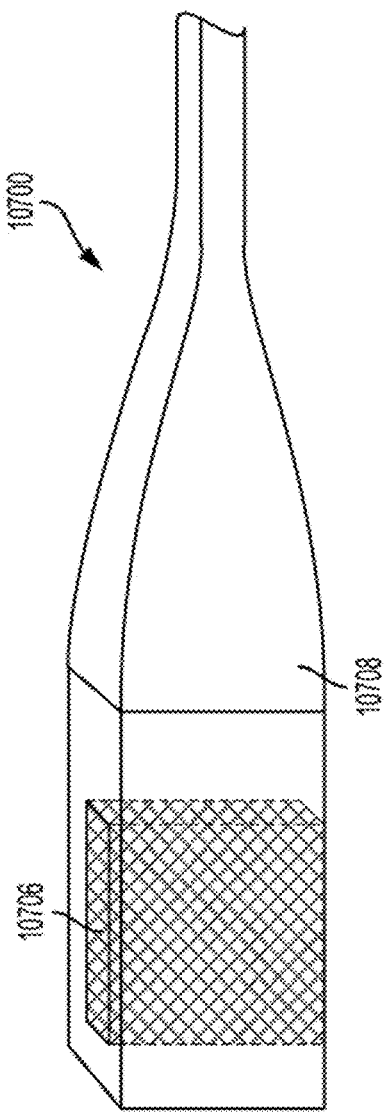

ULTRASONIC TRANSDUCER TO WAVEGUIDE ACOUSTIC COUPLING, CONNECTIONS, AND CONFIGURATIONS

PRIORITY

This application claims the benefit of U.S. Provisional Application Ser. No. 62/379,550 filed Aug. 25, 2016, which is incorporated herein by reference in its entirety.

BACKGROUND

The present disclosure relates, in general, to ultrasonic surgical instruments and more particularly to ultrasonic transducers to drive ultrasonic waveguides. Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, elevate or cauterize tissue or to separate muscle tissue from bone. Ultrasonic instruments utilizing solid core technology are particularly advantageous because of the amount of ultrasonic energy that may be transmitted from the ultrasonic transducer, through a waveguide, and to the surgical end effector. Such instruments may be used for open procedures or minimally invasive procedures, such as endoscopic or laparoscopic procedures, wherein the end effector is passed through a trocar to reach the surgical site.

Activating or exciting the end effector (e.g., cutting blade) of such instruments at ultrasonic frequencies induces longitudinal vibratory movement that generates localized heat within adjacent tissue. Because of the nature of ultrasonic instruments, a particular ultrasonically actuated end effector may be designed to perform numerous functions, including, for example, cutting and coagulation. Ultrasonic vibration is induced in the surgical end effector by electrically exciting a transducer, for example. The transducer may be constructed of one or more piezoelectric or magnetostrictive elements in the instrument hand piece. Vibrations generated by the transducer are transmitted to the surgical end effector via an ultrasonic waveguide extending from the transducer to the surgical end effector. The waveguide and end effector are designed to resonate at the same frequency as the transducer. Therefore, when an end effector is attached to a transducer, the overall system frequency is the same frequency as the transducer itself.

The amplitude of the longitudinal ultrasonic vibration at the tip, d, of the end effector behaves as a simple sinusoid at the resonant frequency as given by:

$$d = A \sin(\omega t)$$

where:

$\omega$=the radian frequency which equals $2\pi$ times the cyclic frequency, f; and A=the zero-to-peak amplitude.

The longitudinal excursion of the end effector tip is defined as the peak-to-peak (p-t-p) amplitude, which is just twice the amplitude of the sine wave or 2A. Often, the end effector can comprise a blade which, owing to the longitudinal excursion, can cut and/or coagulate tissue. U.S. Pat. No. 6,283,981, which issued on Sep. 4, 2001 and is entitled METHOD OF BALANCING ASYMMETRIC ULTRASONIC SURGICAL BLADES; U.S. Pat. No. 6,309,400, which issued on Oct. 30, 2001 and is entitled CURVED ULTRASONIC WAVEGUIDE HAVING A TRAPEZOIDAL CROSS SECTION; and U.S. Pat. No. 6,436,115, which issued on Aug. 20, 2002 and is entitled BALANCED ULTRASONIC WAVEGUIDE INCLUDING A PLURALITY OF BALANCE ASYMMETRIES, the entire disclosures of which are hereby incorporated by reference herein, disclose various ultrasonic surgical instruments.

SUMMARY

In one general aspect, various aspects are directed to an ultrasonic surgical instrument that comprises a transducer configured to produce vibrations along a longitudinal axis of a surgical tool at a predetermined frequency. In various aspects, the surgical tool may include an ultrasonic waveguide that extends along the longitudinal axis and is coupled to the transducer. In various aspects, the surgical tool includes a body having a proximal end and a distal end, wherein the distal end is movable relative to the longitudinal axis by the vibrations produced by the transducer, and the proximal end is mechanically coupled to the transducer.

In one aspect, a compressed ultrasonic transducer assembly is provided. The compressed ultrasonic transducer assembly comprises a metal housing defining an opening; at least two piezoelectric elements disposed within the opening and compressed by a compressive force, wherein the at least two piezoelectric elements are configured to work in a D33 mode; and a metal plug joined to the metal housing to close the opening and to maintain the at least two piezoelectric elements in a compressed state within the metal housing.

In another aspect, an ultrasonic surgical instrument is provided. The ultrasonic surgical instrument comprises an ultrasonic waveguide; an ultrasonic transducer mounted to the ultrasonic waveguide and configured to operated in a D31 mode, ultrasonic transducer comprising: a first ceramic piezoelectric element having a first side attached to a first side of the ultrasonic waveguide by a first bonding material; and a second ceramic piezoelectric element having a first side attached to a second side of the ultrasonic waveguide by the first bonding material, wherein the first side of the ultrasonic waveguide is opposite the second side of the ultrasonic waveguide.

In another aspect, an ultrasonic surgical instrument is provided. The ultrasonic surgical instrument comprises an ultrasonic waveguide comprising: a base portion; first and second walls extending from one side of the base portion; and first and second ledges projecting from the corresponding first and second walls, wherein a first space is defined between the first ledge and the base portion and wherein a second space is defined between the second ledge and the base portion; and an ultrasonic transducer attached to the ultrasonic waveguide, wherein the ultrasonic transducer comprises at least one piezoelectric element slidably disposed between the first and second spaces and fixed therein.

In another aspect, an ultrasonic surgical instrument is provided. The ultrasonic surgical instrument comprises an ultrasonic waveguide; and an ultrasonic transducer attached to the ultrasonic waveguide; wherein the ultrasonic waveguide comprises a tuning-fork-like frame comprising: an upper prong; and a lower prong defining a U-shaped aperture therebetween configured to receive the ultrasonic transducer therein.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 3 illustrates a D31 ultrasonic transducer architecture that includes an ultrasonic waveguide and one or more piezoelectric elements fixed to the ultrasonic waveguide, according to one aspect of the present disclosure.

FIG. 5 is a perspective view of an ultrasonic surgical instrument, according to one aspect of this disclosure.

FIG. 6 is perspective view of a piezoelectric element for use with the ultrasonic surgical instrument shown in FIG. 5, according to one aspect of this disclosure.

FIG. 7 is sectional view of the ultrasonic surgical instrument shown in FIG. 5, according to one aspect of this disclosure.

FIGS. 19A and 19B illustrate a D33 ultrasonic transducer configuration, according to one aspect of this disclosure.

FIG. 20 illustrates a D33 ultrasonic transducer configuration, according to one aspect of this disclosure.

FIG. 21 illustrates a D33 ultrasonic transducer configuration, according to one aspect of this disclosure.

FIGS. 22A-D illustrate a D33 ultrasonic transducer configuration, according to one aspect of this disclosure.

Figure 23:
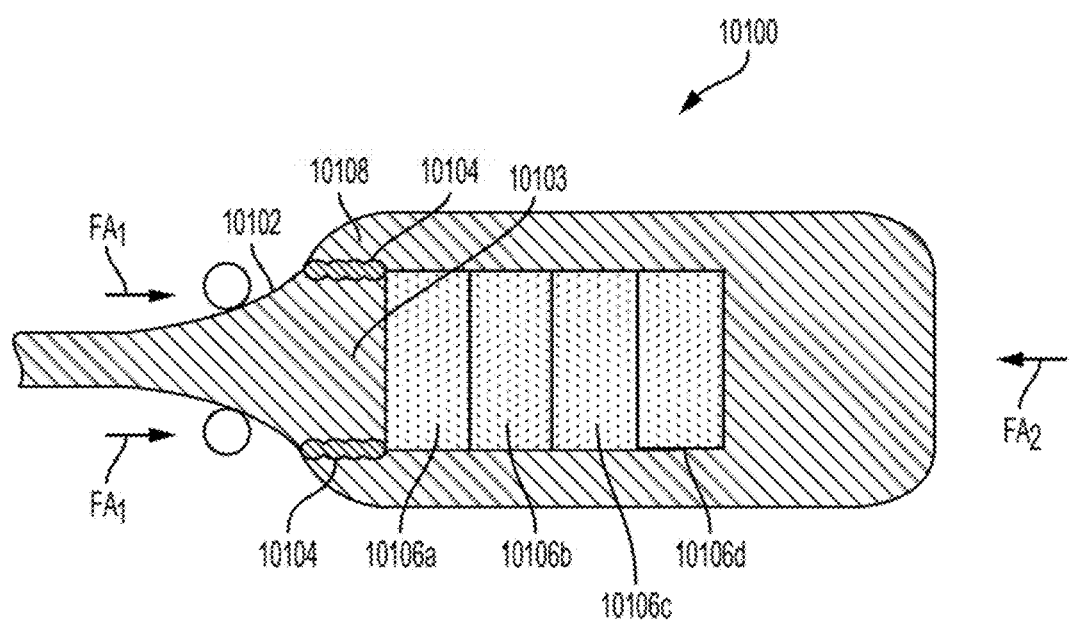

FIG. 23 illustrates a D33 ultrasonic transducer configuration, according to one aspect of this disclosure.

Figure 24A:
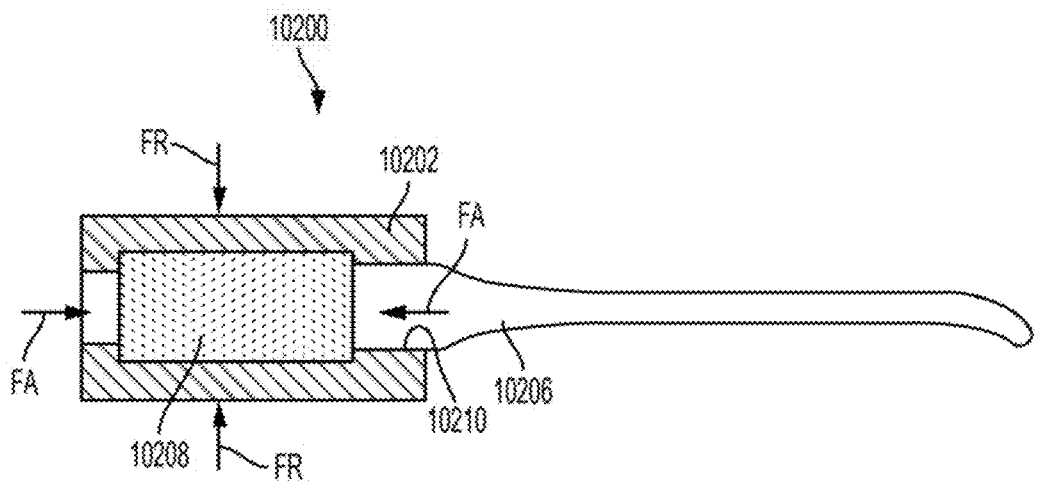

FIG. 24A illustrates a sectional view of a D31 ultrasonic transducer configuration along line 24A-24A, according to one aspect of this disclosure.

Figure 24B:
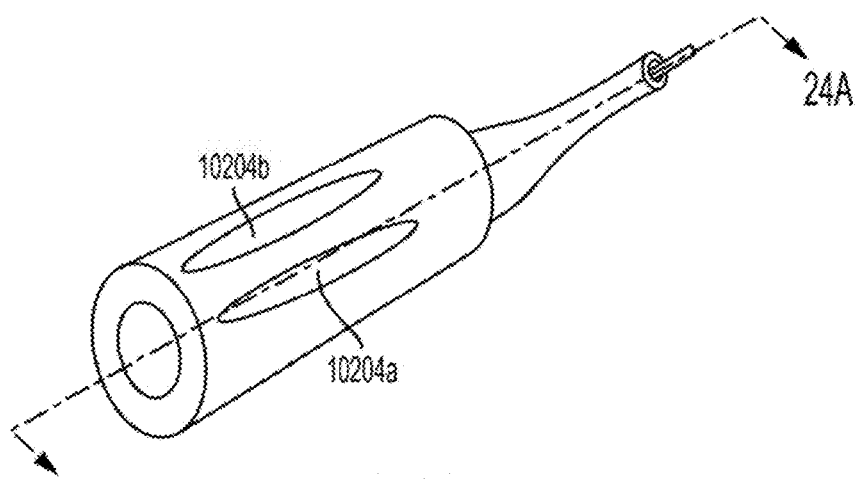

FIG. 24B illustrates a D31 ultrasonic transducer configuration, according to one aspect of this disclosure.

Figure 24C:
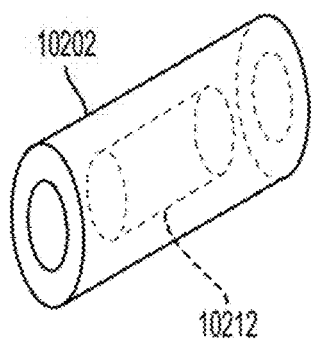

FIG. 24C illustrates the change in shape of the housing of the D31 ultrasonic transducer configuration shown in FIGS. 24A-B, according to one aspect of this disclosure.

FIGS. 25A-E illustrate a D33 ultrasonic transducer configuration, according to one aspect of this disclosure.

Figure 26A:
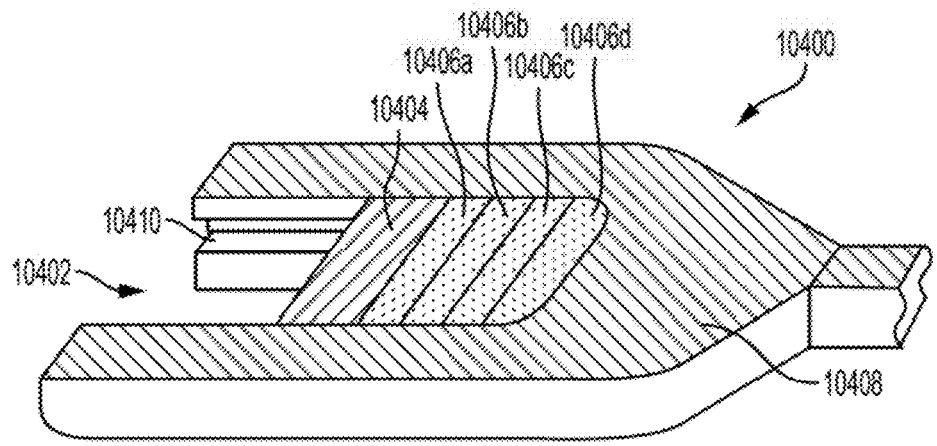

FIG. 26A illustrates a D33 ultrasonic transducer configuration, according to one aspect of this disclosure.

Figure 26B:
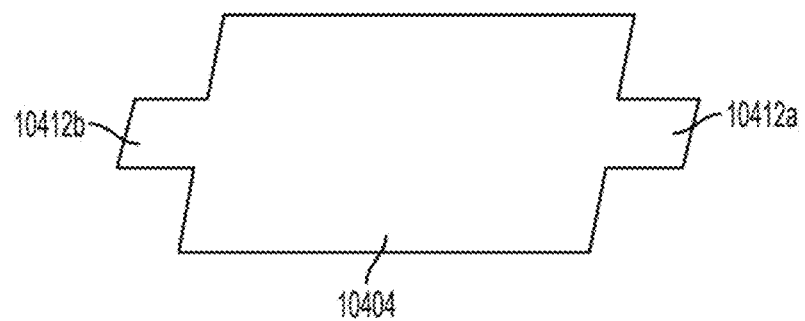

FIG. 26B illustrates the plug of the ultrasonic transducer configuration shown in FIG. 26A, according to one aspect of this disclosure.

Figure 26C:
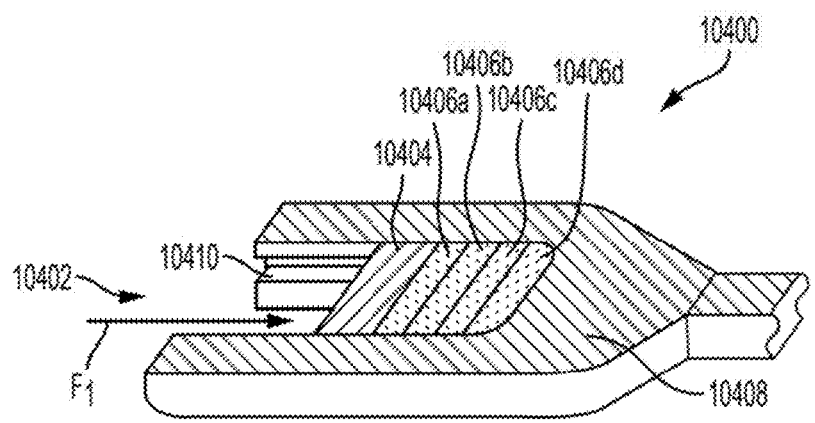
Figure 26D:
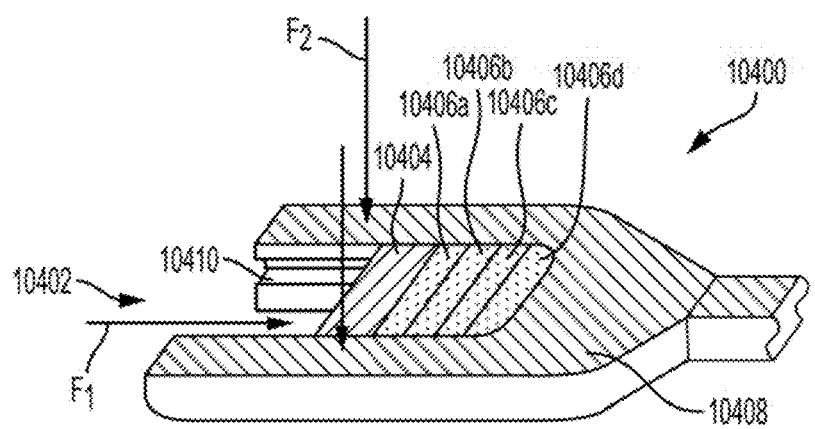

FIGS. 26C-D illustrate a method of installing the D33 ultrasonic transducer configuration shown in FIG. 26A, according to one aspect of this disclosure.

Figure 27:
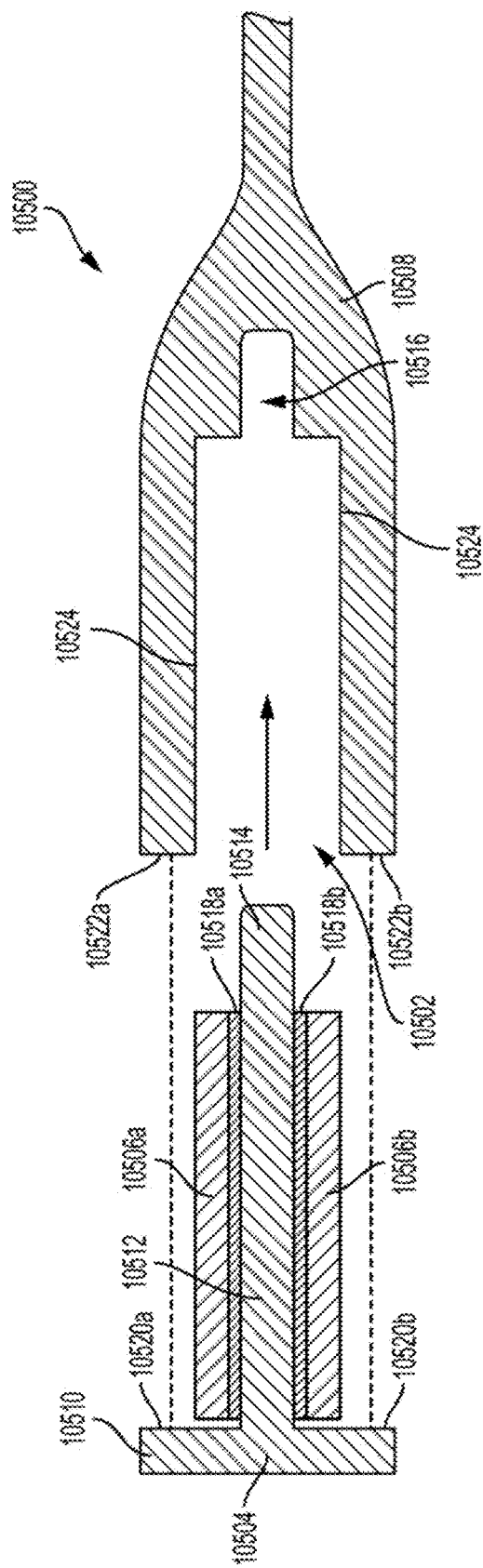

FIG. 27 illustrates a D31 ultrasonic transducer configuration, according to one aspect of this disclosure.

Figure 28:
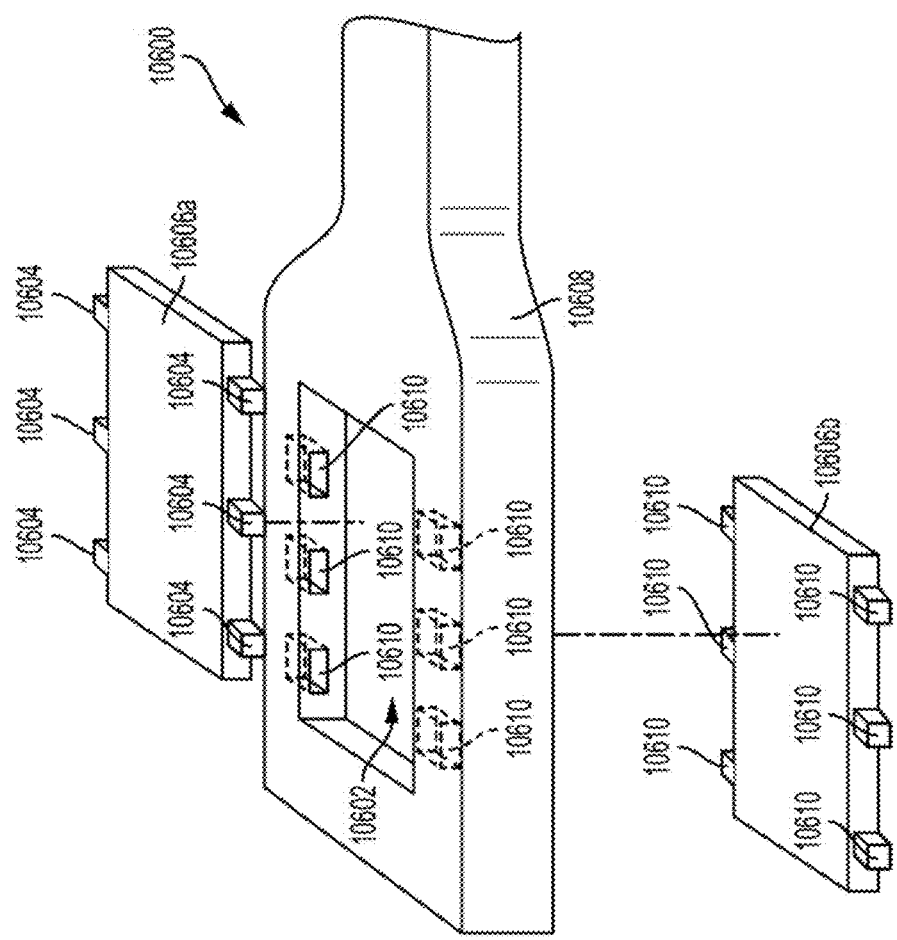

FIG. 28 illustrates a D31 ultrasonic transducer configuration, according to one aspect of this disclosure.

FIGS. 29A-B illustrate a D31 ultrasonic transducer configuration, according to one aspect of this disclosure.

Figure 30A:
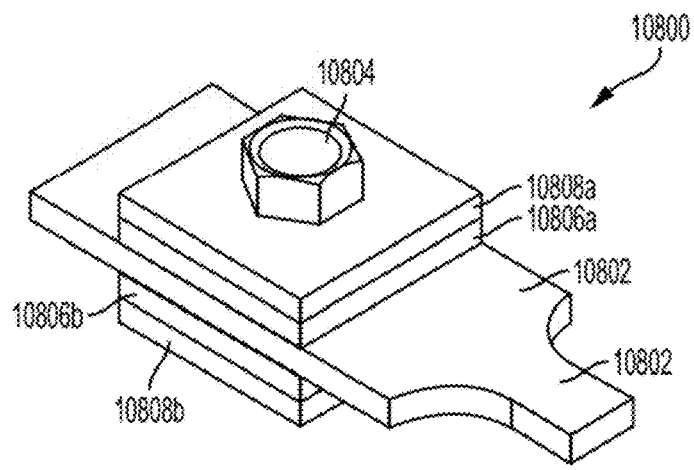

FIG. 30A illustrates a D31 ultrasonic transducer configuration, according to one aspect of this disclosure.

Figure 30B:
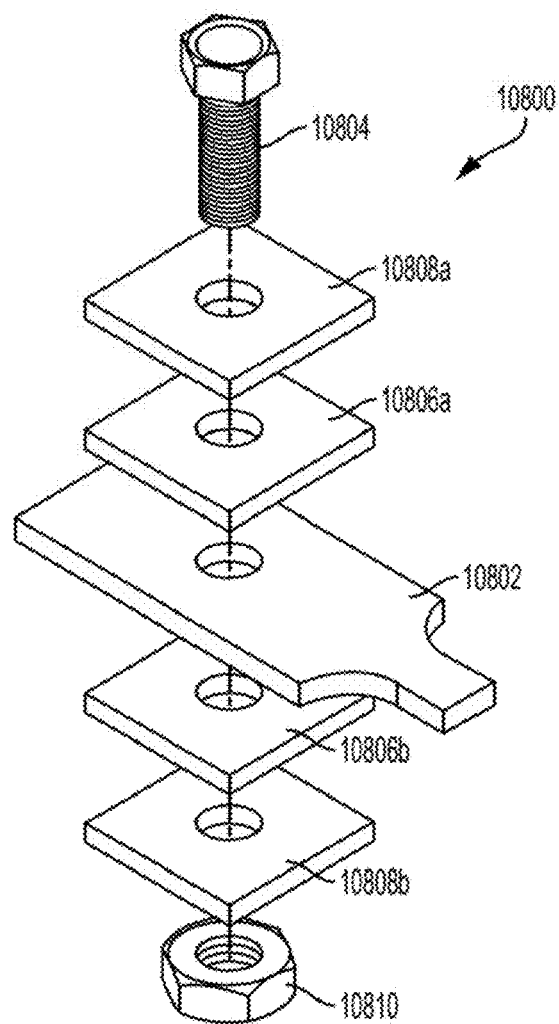

FIG. 30B illustrates an exploded view of the D31 ultrasonic transducer configuration shown in FIG. 30A, according to one aspect of this disclosure.

Figure 30C:
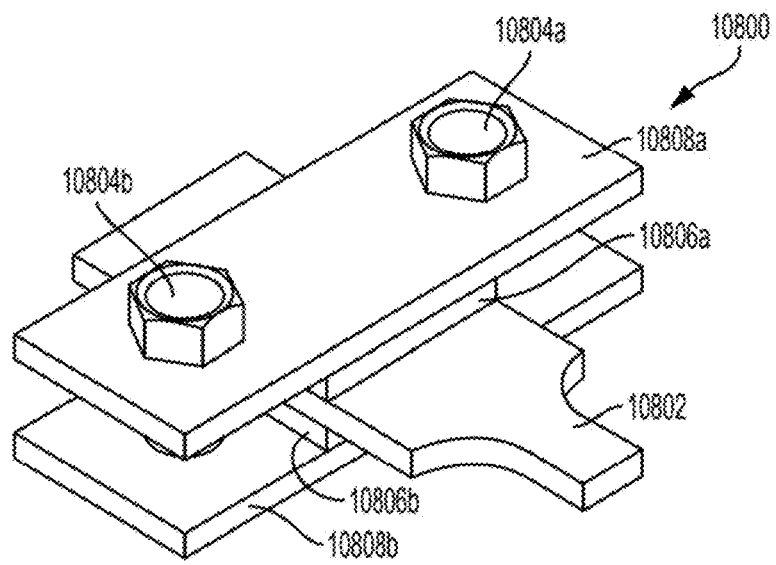

FIG. 30C illustrates a D31 ultrasonic transducer configuration, according to one aspect of this disclosure.

Figure 30D:
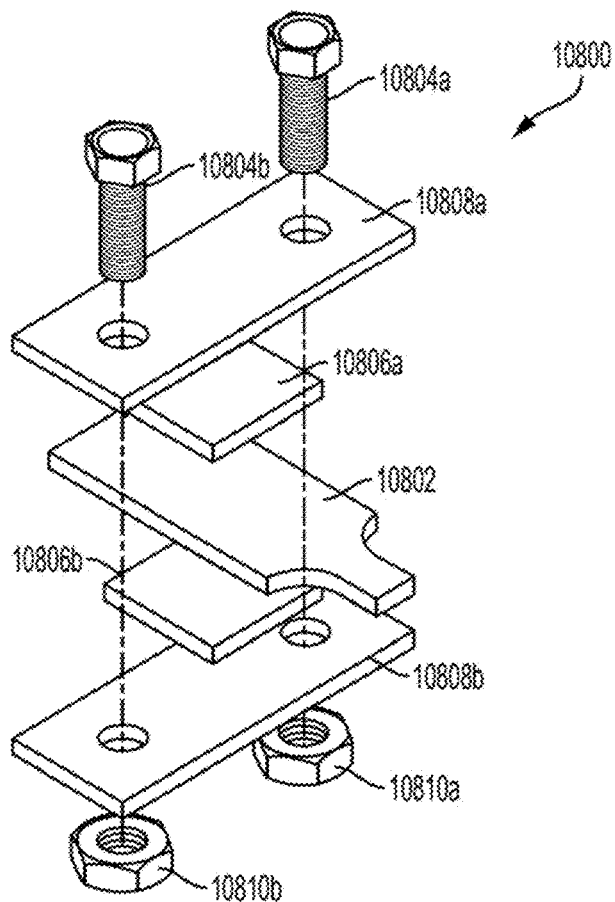

FIG. 30D illustrates an exploded view of the D31 ultrasonic transducer configuration shown in FIG. 30C, according to one aspect of this disclosure.

Figure 31:
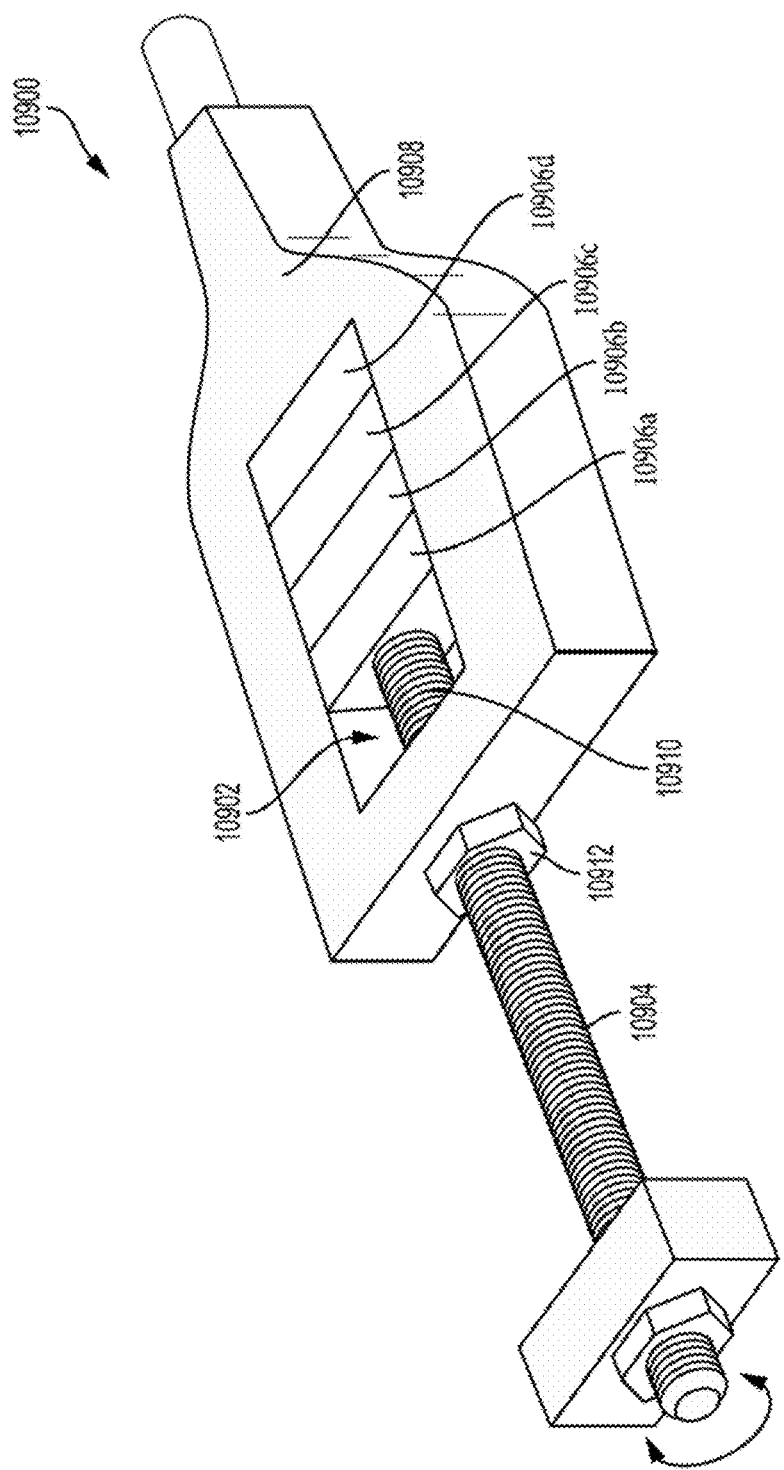

FIG. 31 illustrates a D33 ultrasonic transducer configuration, according to one aspect of this disclosure.

Figure 32A:
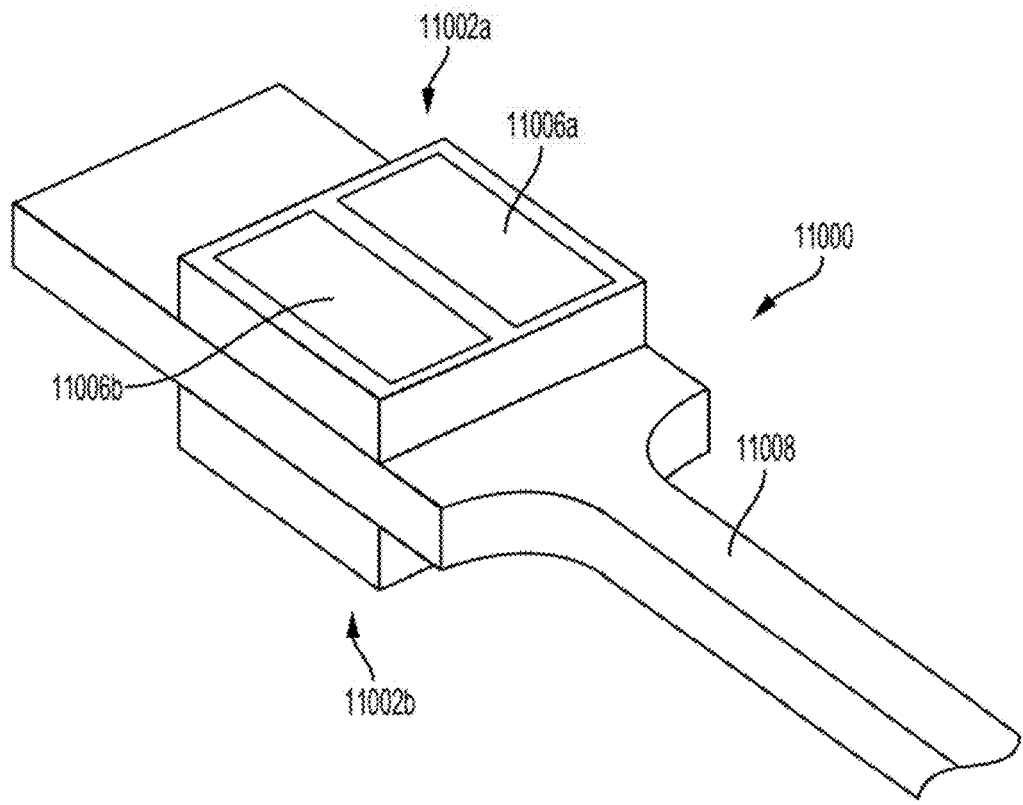
Figure 32B:
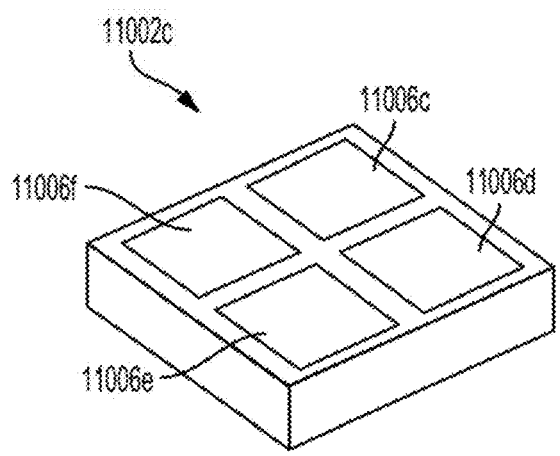

FIGS. 32A-B illustrate D31 ultrasonic transducer configurations having asymmetrically excitable piezoelectric transducer assemblies, according to one aspect of this disclosure.

Figure 33A:
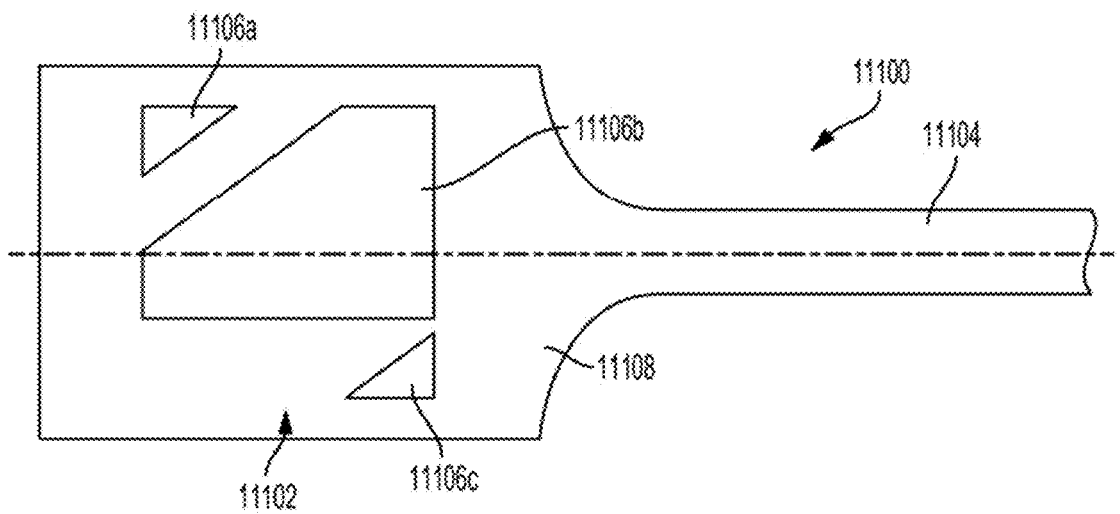
Figure 33B:
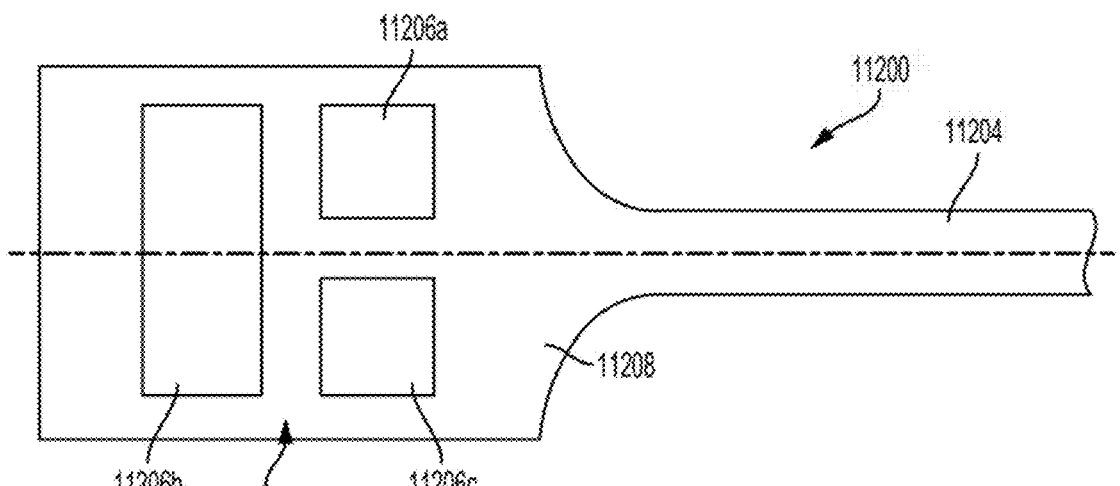
Figure 33C:
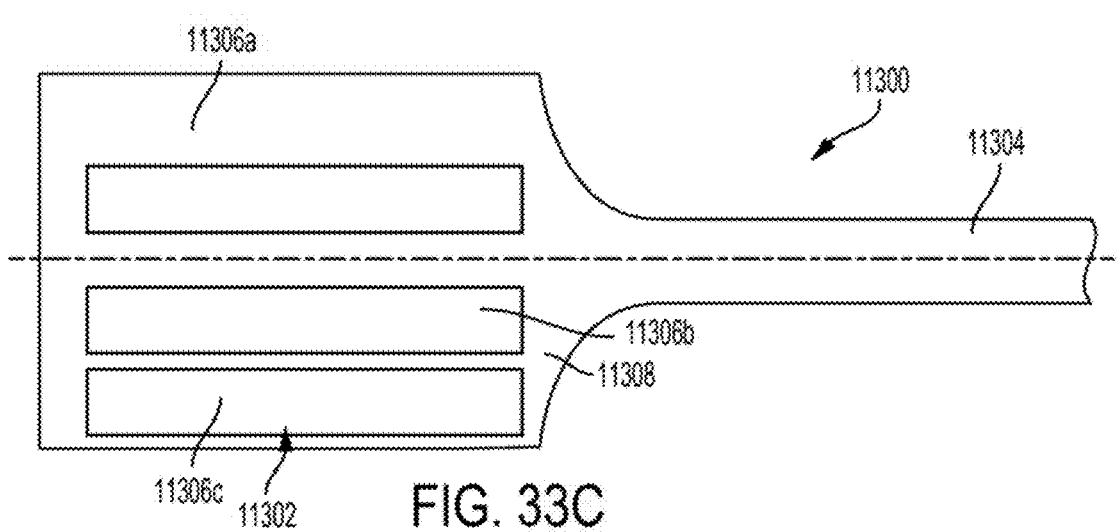

FIGS. 33A-C illustrate D31 ultrasonic transducer configurations having asymmetrically excitable piezoelectric transducer assemblies, according to one aspect of this disclosure.

Figure 34A:
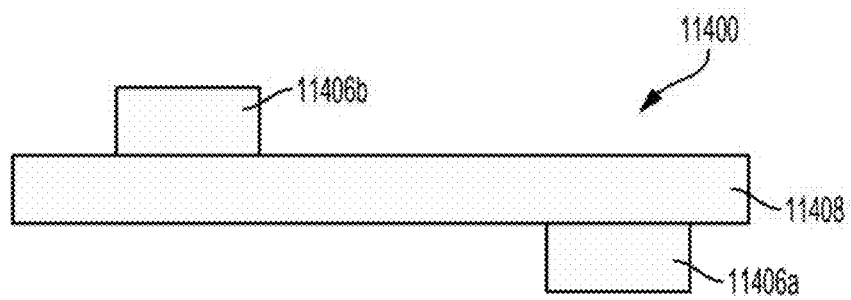
Figure 34B:
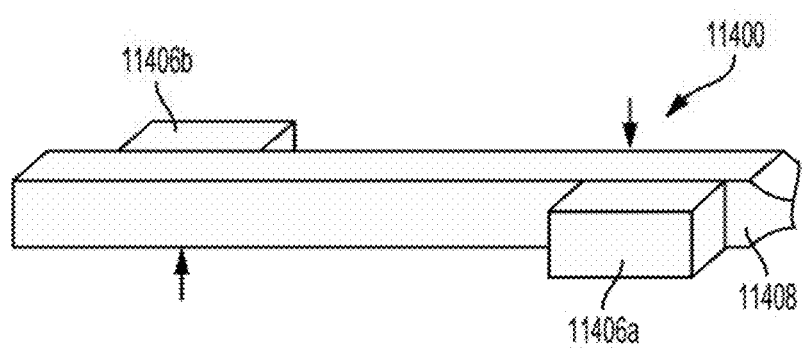

FIGS. 34A-B illustrate a D31 ultrasonic transducer configuration wherein the piezoelectric elements are offset relative to each other, according to one aspect of this disclosure.

Figure 34C:
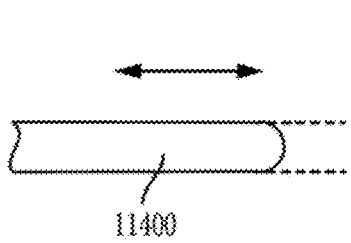
Figure 34D:
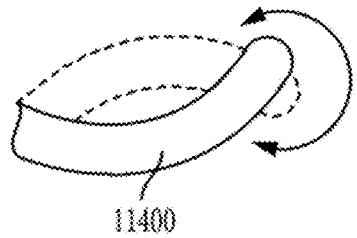

FIGS. 34C-D illustrate plan views of an end effector of a surgical instrument undergoing longitudinal and non-longitudinal motion, respectively, according to one aspect of this disclosure.

Figure 35A:
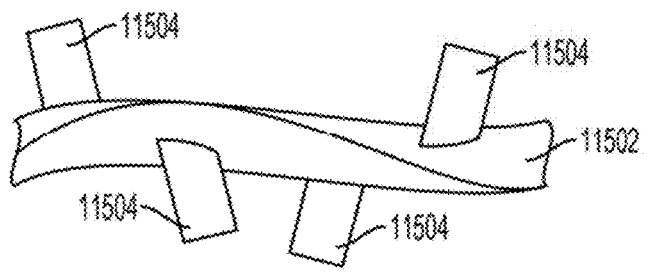

FIG. 35A illustrates a perspective view of a distal end of a waveguide of a surgical instrument having complex features, according to one aspect of this disclosure.

FIGS. 35B-E illustrate a process of fabricating the surgical instrument shown in FIG. 35A, according to one aspect of this disclosure.

Figure 36A:
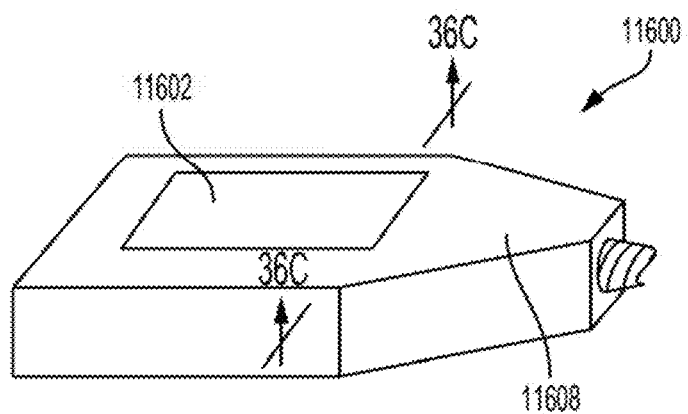

FIG. 36A illustrates a perspective view of a D31 ultrasonic transducer configuration configured to generate non-longitudinal motion, according to one aspect of this disclosure.

Figure 36B:
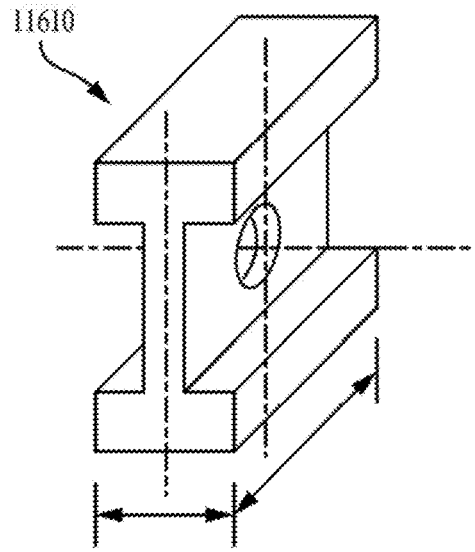

FIG. 36B illustrates a perspective view of an electrode of the D31 ultrasonic transducer configuration shown in FIG. 36A, according to one aspect of this disclosure.

Figure 36C:
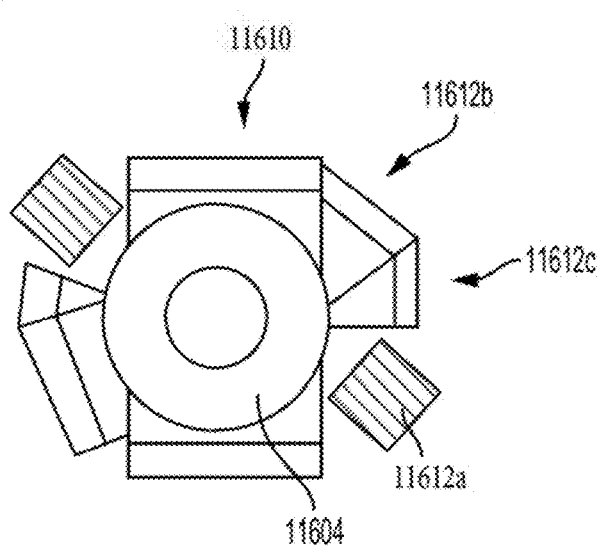

FIG. 36C illustrates a sectional view of the D31 ultrasonic transducer configuration shown in FIG. 36A along line 36C-36C, according to one aspect of this disclosure.

Figure 36D:
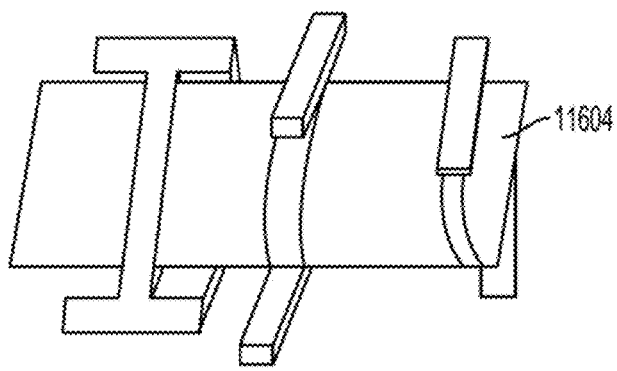

FIG. 36D illustrates a side view of the electrode and piezoelectric transducer assembly of the D31 ultrasonic transducer configuration shown in FIG. 36A, according to one aspect of this disclosure.

Figure 37:
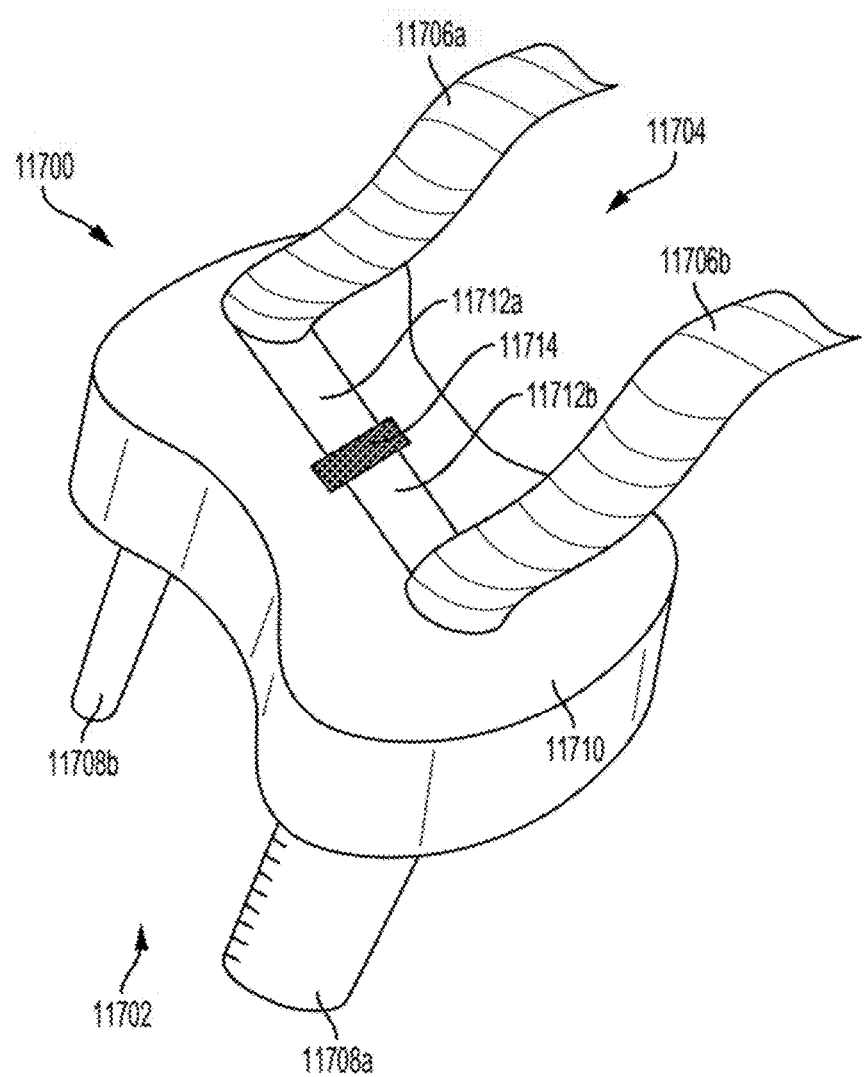

FIG. 37 illustrates a perspective view of an electrical connector to an ultrasonic signal generator for a surgical instrument, according to one aspect of this disclosure.

Figure 38:
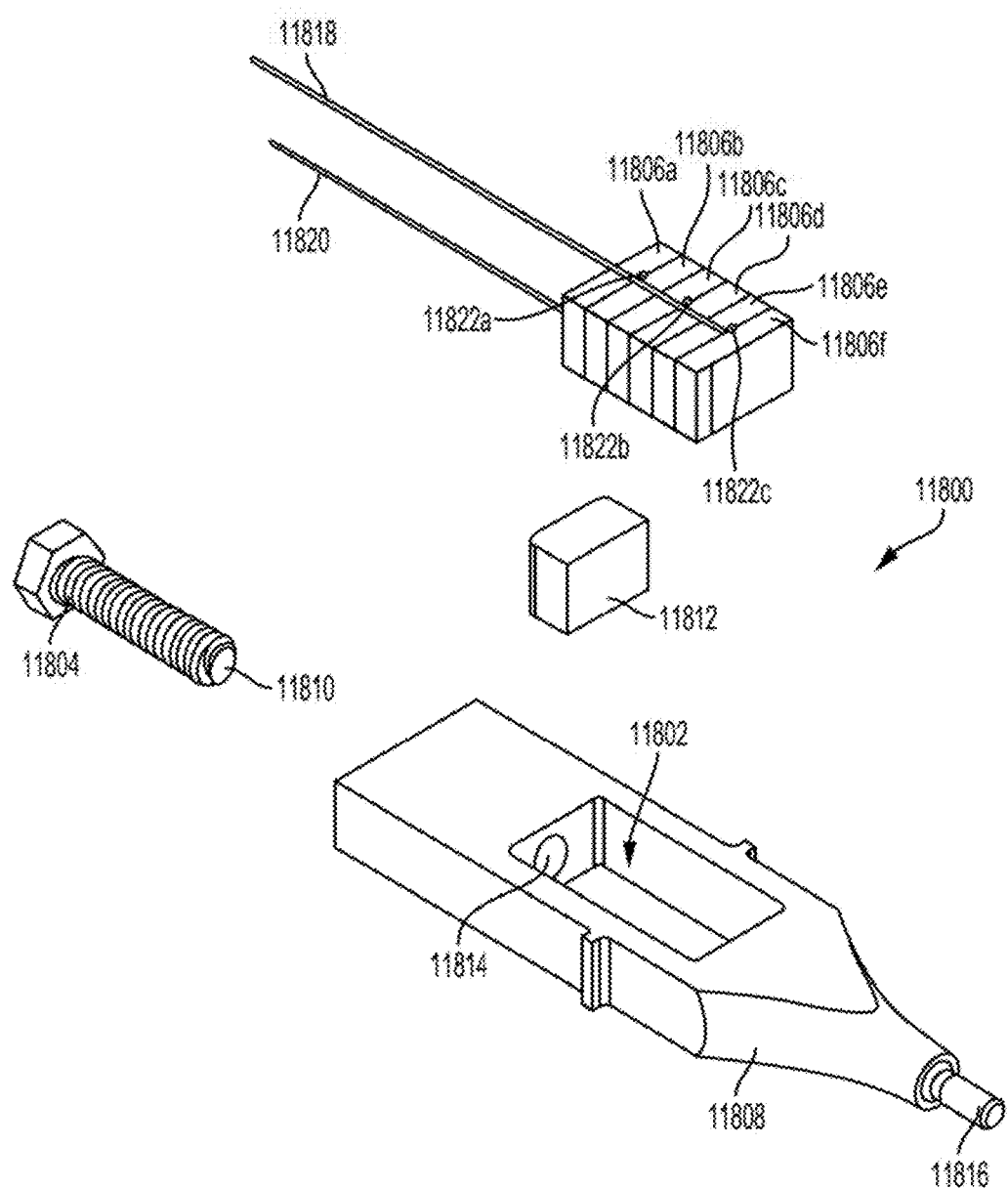

FIG. 38 illustrates an exploded view of a D33 ultrasonic transducer configuration, according to one aspect of this disclosure.

Figure 39:
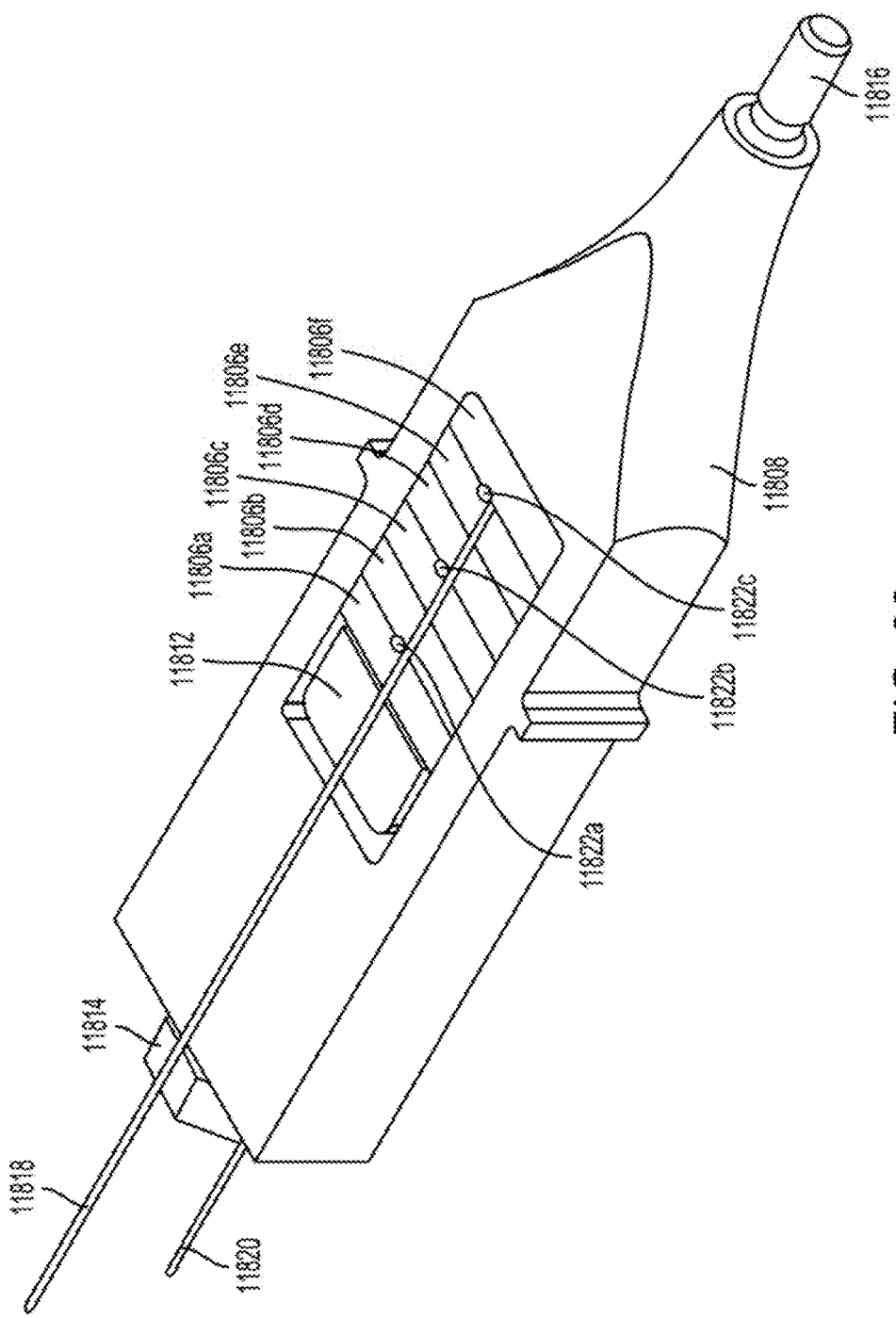

FIG. 39 illustrates a perspective view of the D33 ultrasonic transducer configuration of FIG. 38, according to one aspect of this disclosure.

Figure 40:
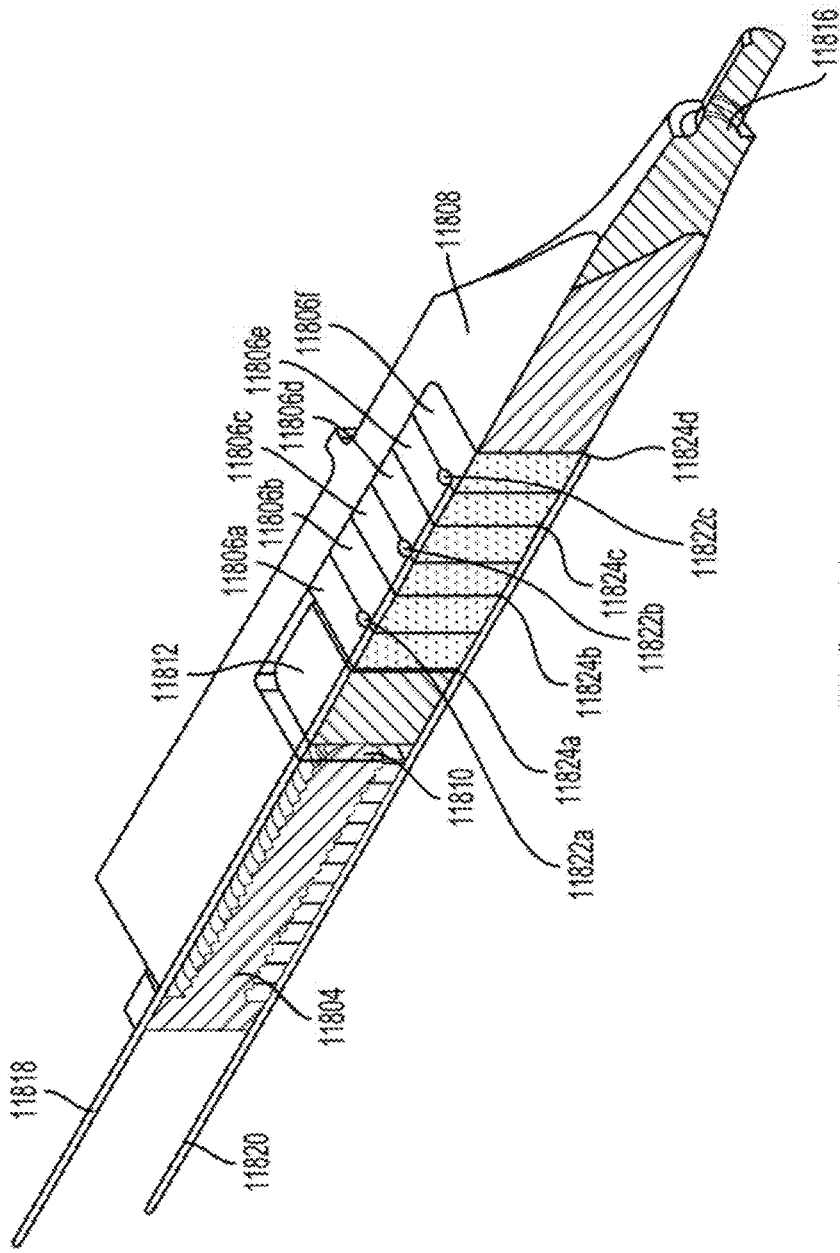

FIG. 40 illustrates a perspective sectional view of the D33 ultrasonic transducer configuration of FIG. 38, according to one aspect of this disclosure.

Figure 41:
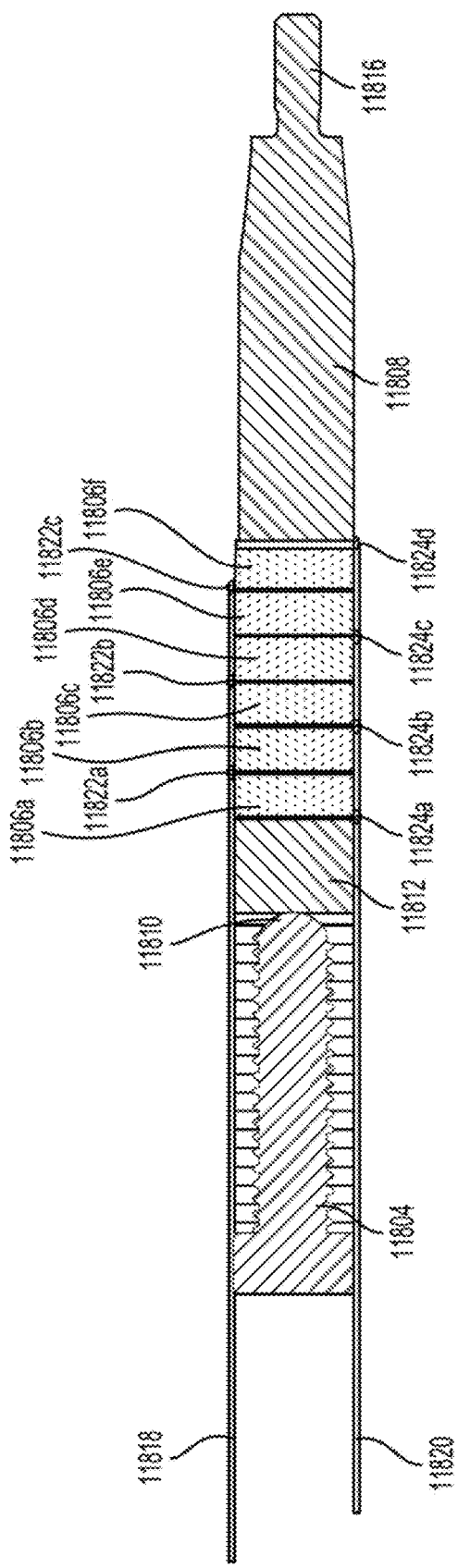

FIG. 41 illustrates a plan sectional view of the D33 ultrasonic transducer configuration of FIG. 38, according to one aspect of this disclosure.

DESCRIPTION

Before explaining various aspects in detail, it should be noted that such aspects are not limited in their application or use to the details of construction and arrangement of parts illustrated in the accompanying drawings and description. The illustrative aspects may be implemented or incorporated in other aspects, variations and modifications, and may be practiced or carried out in various ways. For example, the surgical instruments disclosed below are illustrative only and not meant to limit the scope or application thereof. Furthermore, unless otherwise indicated, the terms and expressions employed herein have been chosen for the purpose of describing the illustrative aspects for the convenience of the reader and are not to limit the scope thereof.

Certain aspects will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting examples aspects and that the scope of the various aspects is defined solely by the claims. The features illustrated or described in connection with one aspect may be combined with the features of other aspects. Such modifications and variations are intended to be included within the scope of the claims.

Various aspects described herein relate, in general, to ultrasonic surgical instruments and blades for use therewith. Examples of ultrasonic surgical instruments and blades are disclosed in U.S. Pat. Nos. 5,322,055; 5,954,736; 6,309,400; 6,278,218; 6,283,981; 6,325,811; and 8,319,400, wherein the entire disclosures of which are incorporated by reference herein.

According to various aspects, an ultrasonic instrument comprising a surgical tool having an end effector such as a blade can be of particular benefit, among others, in orthopedic procedures where it is desirable to remove cortical bone and/or tissue while controlling bleeding. Due to its cutting and coagulation characteristics, a blade of an ultrasonic surgical instrument may be useful for general soft tissue cutting and coagulation. In certain circumstances, a blade according to various aspects may be useful to simultaneously cut and hemostatically seal or cauterize tissue. A blade may be straight or curved, and useful for either open or laparoscopic applications. A blade according to various aspects may be useful in spine surgery, especially to assist in posterior access in removing muscle from bone.

Applicant of the present application owns the following patent applications filed Aug. 17, 2017 and which are each herein incorporated by reference in their respective entireties:

U.S. patent application Ser. No. 15/679,940, entitled Ultrasonic Transducer Techniques for Ultrasonic Surgical Instrument, by inventors Jeffrey Messerly et al., now U.S. Patent Application Publication No. 2018/0055529.

U.S. patent application Ser. No. 15/679,848, entitled "Ultrasonic Transducer For Surgical Instrument, by inventors Jeffrey Messerly et al., now U.S. Pat. No. 10,420,580.

U.S. patent application Ser. No. 15/679,952, entitled "Electrical And Thermal Connections For Ultrasonic Transducer" by inventors Jeffrey Messerly et al., now U.S. Pat. No. 10,736,649.

U.S. patent application Ser. No. 15/679,960, entitled "Ultrasonic Transducer to Waveguide Joining" by inventors Jeffrey Messerly et al., now U.S. Patent Application Publication No. 2018/0055532.

U.S. patent application Ser. No. 15/679,967, entitled "Tissue Loading Of A Surgical Instrument" by inventors Jeffrey Messerly et al., now U.S. Patent Application Publication No. 2018/0078268.

Figure 1:
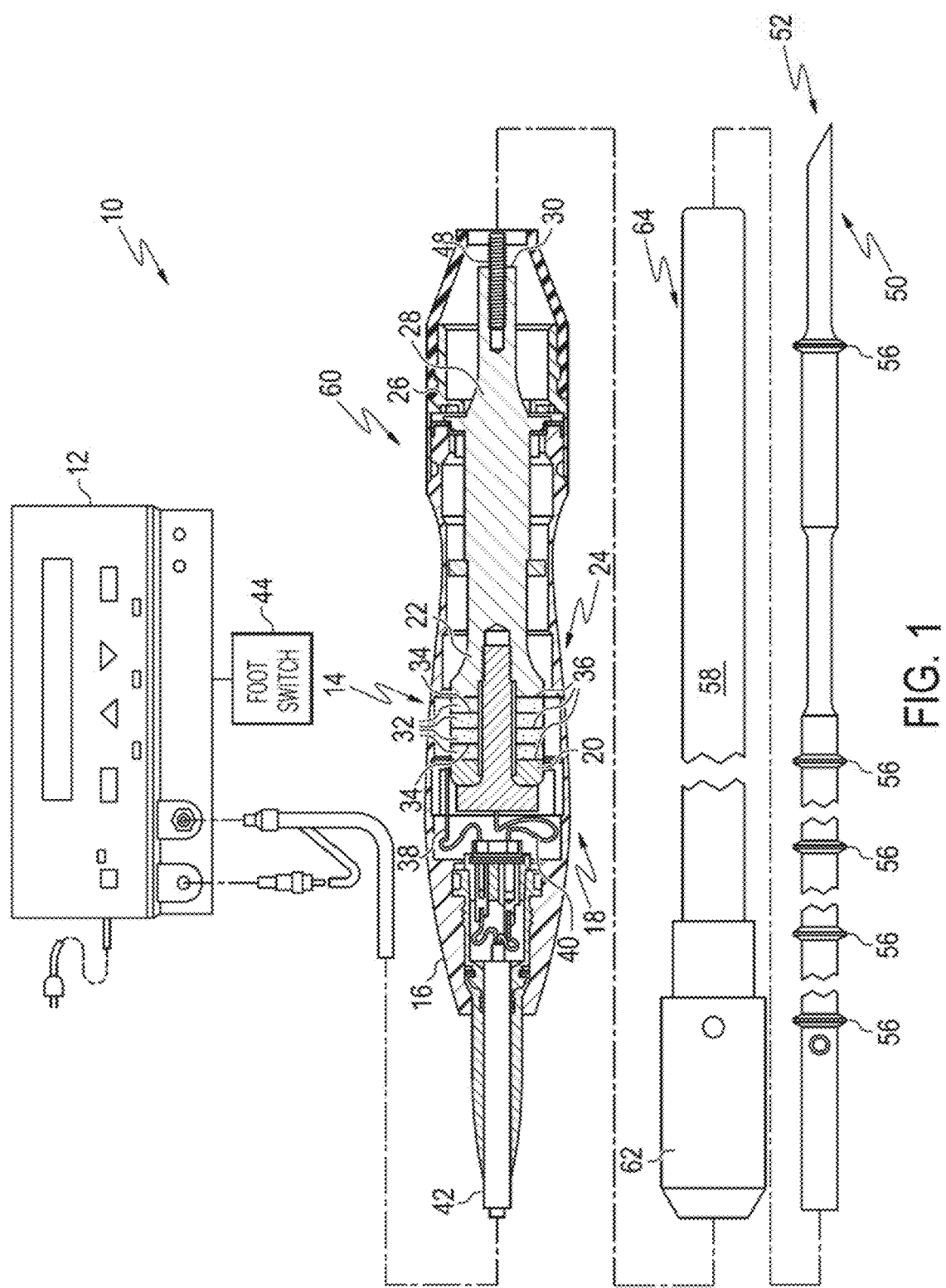
FIG. 1 illustrates an ultrasonic surgical instrument system, according to one aspect of this disclosure.

FIG. 1 illustrates one aspect of an ultrasonic system 10. One aspect of the ultrasonic system 10 comprises an ultrasonic signal generator 12 coupled to an ultrasonic transducer 14, a hand piece assembly 60 comprising a hand piece housing 16, and an end effector 50. The ultrasonic transducer 14, which is known as a "Langevin stack," generally includes a transduction portion 18, a first resonator or end-bell 20, and a second resonator or fore-bell 22, and ancillary components. In various aspects, the ultrasonic transducer 14 is preferably an integral number of one-half system wavelengths ($n\lambda/2$) in length as will be described in more detail below. An acoustic assembly 24 can include the ultrasonic transducer 14, a mount 26, a velocity transformer 28, and a surface 30.

It will be appreciated that the terms "proximal" and "distal" are used herein with reference to a clinician gripping the hand piece assembly 60. Thus, the end effector 50 is distal with respect to the more proximal hand piece assembly 60. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The distal end of the end-bell 20 is connected to the proximal end of the transduction portion 18, and the proximal end of the fore-bell 22 is connected to the distal end of the transduction portion 18. The fore-bell 22 and the end-bell 20 have a length determined by a number of variables, including the thickness of the transduction portion 18, the density and modulus of elasticity of the material used to manufacture the end-bell 20 and the fore-bell 22, and the resonant frequency of the ultrasonic transducer 14. The fore-bell 22 may be tapered inwardly from its proximal end to its distal end to amplify the ultrasonic vibration amplitude of the velocity transformer 28, or, alternately, fore-bell 22 may have no amplification.

Referring again to FIG. 1, end-bell 20 can include a threaded member extending therefrom which can be configured to be threadably engaged with a threaded aperture in fore-bell 22. In various aspects, piezoelectric elements, such as piezoelectric elements 32, for example, can be compressed between end-bell 20 and fore-bell 22 when end-bell 20 and fore-bell 22 are assembled together. Piezoelectric elements 32 may be fabricated from any suitable material, such as, for example, lead zirconate-titanate, lead meta-niobate, lead titanate, and/or any suitable piezoelectric crystal material, for example.

In various aspects, as discussed in greater detail below, transducer 14 can further comprise electrodes, such as positive electrodes 34 and negative electrodes 36, for example, which can be configured to create a voltage potential across one or more piezoelectric elements 32. Each of the positive electrodes 34, negative electrodes 36, and the piezoelectric elements 32 can comprise a bore extending through the center which can be configured to receive the threaded member of end-bell 20. In various aspects, the positive and negative electrodes 34 and 36 are electrically coupled to wires 38 and 40, respectively, wherein the wires 38 and 40 can be encased within a cable 42 and electrically connectable to the ultrasonic signal generator 12 of the ultrasonic system 10.

In various aspects, the ultrasonic transducer 14 of the acoustic assembly 24 converts the electrical signal from the ultrasonic signal generator 12 into mechanical energy that results in primarily longitudinal vibratory motion of the ultrasonic transducer 14 and the end effector 50 at ultrasonic frequencies. A suitable generator is available as model number GEN11, from Ethicon Endo-Surgery, Inc., Cincinnati, Ohio. When the acoustic assembly 24 is energized, a vibratory motion standing wave is generated through the acoustic assembly 24. A suitable vibrational frequency range may be about 20 Hz to 120 kHz and a well-suited vibrational frequency range may be about 30-70 kHz and one Example operational vibrational frequency may be approximately 55.5 kHz.

The amplitude of the vibratory motion at any point along the acoustic assembly 24 may depend upon the location along the acoustic assembly 24 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node (i.e., where motion is usually maximal). The distance between an anti-node and its nearest node is one-quarter wavelength ($\lambda/4$).

As outlined above, the wires 38 and 40 transmit an electrical signal from the ultrasonic signal generator 12 to the positive electrodes 34 and the negative electrodes 36. The piezoelectric elements 32 are energized by the electrical signal supplied from the ultrasonic signal generator 12 in response to a foot switch 44, for example, to produce an acoustic standing wave in the acoustic assembly 24. The electrical signal causes disturbances in the piezoelectric elements 32 in the form of repeated small displacements resulting in large compression forces within the material. The repeated small displacements cause the piezoelectric elements 32 to expand and contract in a continuous manner along the axis of the voltage gradient, producing longitudinal waves of ultrasonic energy.

In various aspects, the ultrasonic energy produced by transducer 14 can be transmitted through the acoustic assembly 24 to the end effector 50 via an ultrasonic transmission waveguide 46. In order for the acoustic assembly 24 to deliver energy to the end effector 50, the components of the acoustic assembly 24 are acoustically coupled to the end effector 50. For example, the distal end of the ultrasonic transducer 14 may be acoustically coupled at the surface 30 to the proximal end of the ultrasonic transmission waveguide 46 by a threaded connection such as a stud 48.

The components of the acoustic assembly 24 can be acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 24, and where n is any positive integer. It is also contemplated that the acoustic assembly 24 may incorporate any suitable arrangement of acoustic elements.

The ultrasonic end effector 50 may have a length substantially equal to an integral multiple of one-half system wavelengths ($\lambda/2$). A distal end 52 of the ultrasonic end effector 50 may be disposed at, or at least near, an antinode in order to provide the maximum, or at least nearly maximum, longitudinal excursion of the distal end. When the transducer assembly is energized, in various aspects, the distal end 52 of the ultrasonic end effector 50 may be configured to move in the range of, for example, approximately 10 to 500 microns peak-to-peak and preferably in the range of approximately 30 to 150 microns at a predetermined vibrational frequency.

As outlined above, the ultrasonic end effector 50 may be coupled to the ultrasonic transmission waveguide 46. In various aspects, the ultrasonic end effector 50 and the ultrasonic transmission guide 46 as illustrated are formed as a single unit construction from a material suitable for transmission of ultrasonic energy such as, for example, Ti6Al4V (an alloy of titanium including aluminum and vanadium), aluminum, stainless steel, and/or any other suitable material. Alternately, the ultrasonic end effector 50 may be separable (and of differing composition) from the ultrasonic transmission waveguide 46, and coupled by, for example, a stud, weld, glue, quick connect, or other suitable known methods. The ultrasonic transmission waveguide 46 may have a length substantially equal to an integral number of one-half system wavelengths ($\lambda/2$), for example. The ultrasonic transmission waveguide 46 may be preferably fabricated from a solid core shaft constructed out of material that propagates ultrasonic energy efficiently, such as titanium alloy (i.e., Ti6Al4V) or an aluminum alloy, for example.

In the aspect illustrated in FIG. 1, the ultrasonic transmission waveguide 46 comprises a plurality of stabilizing silicone rings or compliant supports 56 positioned at, or at least near, a plurality of nodes. The silicone rings 56 can dampen undesirable vibration and isolate the ultrasonic energy from a sheath 58 at least partially surrounding waveguide 46, thereby assuring the flow of ultrasonic energy in a longitudinal direction to the distal end 52 of the end effector 50 with maximum efficiency.

As shown in FIG. 1, the sheath 58 can be coupled to the distal end of the handpiece assembly 60. The sheath 58 generally includes an adapter or nose cone 62 and an elongated tubular member 64. The tubular member 64 is attached to and/or extends from the adapter 62 and has an opening extending longitudinally therethrough. In various aspects, the sheath 58 may be threaded or snapped onto the distal end of the housing 16. In at least one aspect, the ultrasonic transmission waveguide 46 extends through the opening of the tubular member 64 and the silicone rings 56 can contact the sidewalls of the opening and isolate the ultrasonic transmission waveguide 46 therein. In various aspects, the adapter 62 of the sheath 58 is preferably constructed from Ultem®, for example, and the tubular member 64 is fabricated from stainless steel, for example. In at least one aspect, the ultrasonic transmission waveguide 46 may have polymeric material, for example, surrounding it in order to isolate it from outside contact.

As described above, a voltage, or power source can be operably coupled with one or more of the piezoelectric elements of a transducer, wherein a voltage potential applied to each of the piezoelectric elements can cause the piezoelectric elements to expand and contract, or vibrate, in a longitudinal direction. As also described above, the voltage potential can be cyclical and, in various aspects, the voltage potential can be cycled at a frequency which is the same as, or nearly the same as, the resonant frequency of the system of components comprising transducer 14, wave guide 46, and end effector 50, for example. In various aspects, however, certain of the piezoelectric elements within the transducer may contribute more to the standing wave of longitudinal vibrations than other piezoelectric elements within the transducer. More particularly, a longitudinal strain profile may develop within a transducer wherein the strain profile may control, or limit, the longitudinal displacements that some of the piezoelectric elements can contribute to the standing wave of vibrations, especially when the system is being vibrated at or near its resonant frequency.

It may be recognized, in reference to the ultrasonic surgical instrument system 10 of FIG. 1, that multiple components may be required to couple the mechanical vibrations from the piezoelectric elements 32 through the wave guide 46 to the end effector 50. The additional elements comprising the acoustic assembly 24 may add additional manufacturing costs, fabrication steps, and complexity to the system. Disclosed below are aspects of an ultrasonic medical device that may require fewer components, manufacturing steps, and costs than the equivalent device illustrated in FIG. 1 and as disclosed above.

Again, referring to FIG. 1, the piezoelectric elements 32 are configured into a "Langevin" stack, in which the piezoelectric elements 32 and their activating electrodes 34 and 36 (together, transducer 14) are interleaved. The mechanical vibrations of the activated piezoelectric elements 32 propagate along the longitudinal axis of the transducer 14, and are coupled via the acoustic assembly 24 to the end of the waveguide 46. Such a mode of operation of a piezoelectric element is frequently described as the D33 mode of the element, especially for ceramic piezoelectric elements comprising, for example, lead zirconate-titanate, lead metaniobate, or lead titanate. The D33 mode of a ceramic piezoelectric element is illustrated in FIGS. 2A-2C.

Figure 2A:
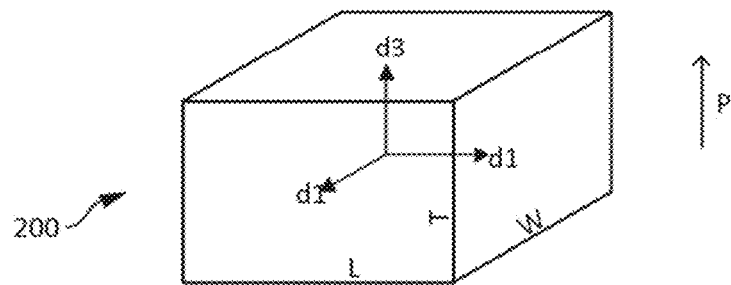
FIGS. 2A-2C illustrate a piezoelectric transducer, according to one aspect of this disclosure.

FIG. 2A depicts a piezoelectric element 200 fabricated from a ceramic piezoelectric material. A piezoelectric ceramic material is a polycrystalline material comprising a plurality of individual microcrystalline domains. Each microcrystalline domain possesses a polarization axis along which the domain may expand or contract in response to an imposed electric field. However, in a native ceramic, the polarization axes of the microcrystalline domains are arranged randomly, so there is no net piezoelectric effect in the bulk ceramic. A net re-orientation of the polarization axes may be induced by subjecting the ceramic to a temperature above the Curie temperature of the material and placing the material in a strong electrical field. Once the temperature of the sample is dropped below the Curie temperature, a majority of the individual polarization axes will be re-oriented and fixed in a bulk polarization direction. FIG. 2A illustrates such a piezoelectric element 200 after being polarized along the inducing electric field axis P. While the un-polarized piezoelectric element 200 lacks any net piezoelectric axis, the polarized element 200 can be described as possessing a polarization axis, d3, parallel to the inducing field axis P direction. For completeness, an axis orthogonal to the d3 axis may be termed a d1 axis. The dimensions of the piezoelectric element 200 are labeled as length (L), width (W), and thickness (T).

Figure 2B:
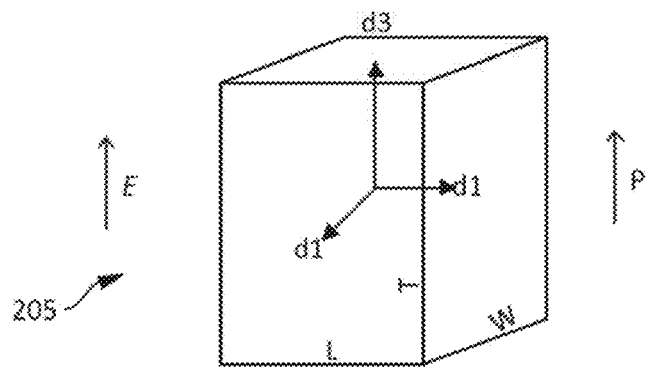
Figure 2C:
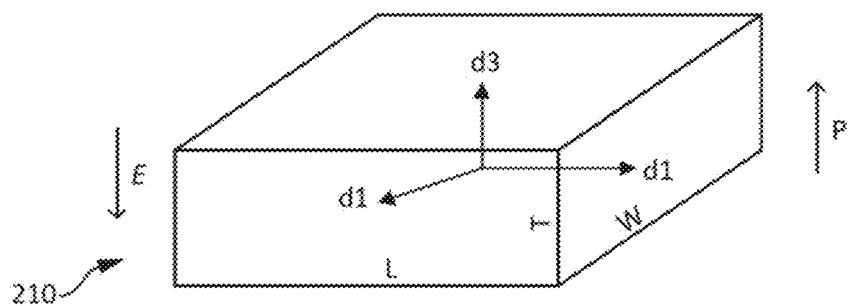

FIGS. 2B and 2C illustrate the mechanical deformations of a piezoelectric element 200 that may be induced by subjecting the piezoelectric element 200 to an actuating electrical field E oriented along the d3 (or P) axis. FIG. 2B illustrates the effect of an electric field E having the same direction as the polarization field P along the d3 axis on a piezoelectric element 205. As illustrated in FIG. 2B, the piezoelectric element 205 may deform by expanding along the d3 axis while compressing along the d1 axis. FIG. 2C illustrates the effect of an electric field E having the opposing direction to the polarization field P along the d3 axis on a piezoelectric element 210. As illustrated in FIG. 2C, the piezoelectric element 210 may deform by compressing along the d3 axis, while expanding along the d1 axis. Vibrational coupling along the d3 axis during the application of an electric field along the d3 axis may be termed D33 coupling or activation using a D33 mode of a piezoelectric element. The transducer 14 illustrated in FIG. 1 uses the D33 mode of the piezoelectric elements 32 for transmitting mechanical vibrations along the wave guide 46 to the end effector 50. Because the piezoelectric element also deforms along the d1 axis, vibrational coupling along the d1 axis during the application of an electric field along the d3 axis may also be an effective source of mechanical vibrations. Such coupling may be termed D31 coupling or activation using a D31 mode of a piezoelectric element.

As illustrated by FIGS. 2A-2C, during operation in the D31 mode, transverse expansion of piezoelectric elements 200, 205, 210 may be mathematically modeled by the following equation:

$$\frac{\Delta L}{L} = \frac{\Delta W}{W} = \frac{V_{d31}}{T}$$

In the equation, L, W, and T refer to the length, width and thickness dimensions of a piezoelectric element, respectively. $Vd_{31}$ denotes the voltage applied to a piezoelectric element operating in the D31 mode. The quantity of transverse expansion resulting from the D31 coupling described above is represented by ΔL (i.e. expansion of the piezoelectric element along the length dimension) and ΔW (i.e. expansion of the piezoelectric element along the width dimension). Additionally, the transverse expansion equation models the relationship between ΔL and ΔW and the applied voltage $Vd_{31}$. Disclosed below are aspects of ultrasonic medical devices based on D31 activation by a piezoelectric element.

In various aspects, as described below, a ultrasonic medical device can comprise a transducer configured to produce longitudinal vibrations, and a surgical tool having a transducer base plate (e.g., a transducer mounting portion) operably coupled to the transducer, an end effector, and wave guide therebetween. In certain aspects, as also described below, the transducer can produce vibrations which can be transmitted to the end effector, wherein the vibrations can drive the transducer base plate, the wave guide, the end effector, and/or the other various components of the ultrasonic medical device at, or near, a resonant frequency. In resonance, a longitudinal strain pattern, or longitudinal stress pattern, can develop within the transducer, the wave guide, and/or the end effector, for example. In various aspects, such a longitudinal strain pattern, or longitudinal stress pattern, can cause the longitudinal strain, or longitudinal stress, to vary along the length of the transducer base plate, wave guide, and/or end effector, in a sinusoidal, or at least substantially sinusoidal, manner. In at least one aspect, for example, the longitudinal strain pattern can have maximum peaks and zero points, wherein the strain values can vary in a non-linear manner between such peaks and zero points.

FIG. 3 illustrates an ultrasonic surgical instrument 250 that includes an ultrasonic waveguide 252 attached to an ultrasonic transducer 264 by a bonding material, where the ultrasonic surgical instrument 250 is configured to operate in a D31 mode, according to one aspect of the present disclosure. The ultrasonic transducer 264 includes first and second piezoelectric elements 254a, 254b attached to the ultrasonic waveguide 252 by a bonding material. The piezoelectric elements 254a, 254b include electrically conductive plates 256a, 256b to electrically couple one pole of a voltage source suitable to drive the piezoelectric elements 254a, 254b (e.g., usually a high voltage). The opposite pole of the voltage source is electrically coupled to the ultrasonic waveguide 252 by electrically conductive joints 258a, 258b. In one aspect, the electrically conductive plates 256a, 256b are coupled to a positive pole of the voltage source and the electrically conductive joints 258a, 258b are electrically coupled to ground potential through the metal ultrasonic waveguide 252. In one aspect, the ultrasonic waveguide 252 is made of titanium or titanium alloy (i.e., Ti6Al4V) and the piezoelectric elements 254a, 254b are made of a lead zirconate titanate intermetallic inorganic compound with the chemical formula $Pb[Zr_xTi_{1-x}]O_3$ (0≤x≤1). Also called PZT, it is a ceramic perovskite material that shows a marked piezoelectric effect, meaning that the compound changes shape when an electric field is applied. It is used in a number of practical applications such as ultrasonic transducers and piezoelectric resonators PZT. The poling axis (P) of the piezoelectric elements 254a, 254b is indicated by the direction arrow 260. The motion axis of the ultrasonic waveguide 252 in response to excitation of the piezoelectric elements 254a, 245b is shown by a motion arrow 262 at the distal end of the ultrasonic waveguide 252 generally referred to as the ultrasonic blade portion of the ultrasonic waveguide 252. The motion axis 262 is orthogonal to the poling axis (P) 260.

In conventional D33 ultrasonic transducer architectures as shown in FIG. 1, the bolted piezoelectric elements 32 utilize electrodes 34, 36 to create electrical contact to both sizes of each piezoelectric element 32. The D31 architecture 250 according to one aspect of the present disclosure, however, employs a different technique to create electrical contact to both sides of each piezoelectric element 254a, 254b. Various techniques for providing electrical contact to the piezoelectric elements 254a, 254b include bonding electrical conductive elements (e.g., wires) to the free surface of each piezoelectric element 254a, 254b for the high potential connection and bonding each piezoelectric element 254a, 254b the to the ultrasonic waveguide 252 for the ground connection using solder, conductive epoxy, or other techniques described herein. Compression can be used to maintain electrical contact to the acoustic train without making a permanent connection. This can cause an increase in device thickness and should be controlled to avoid damaging the piezoelectric elements 254a, 254b. Low compression can damage the piezoelectric element 254a, 254b by a spark gap and high compression can damage the piezoelectric elements 254a, 254b by local mechanical wear. In other techniques, metallic spring contacts may be employed to create electrical contact with the piezoelectric elements 254a, 254b. Other techniques may include foil-over-foam gaskets, conductive foam, solder. Electrical connection to both sides of the piezoelectric elements 254a, 254b the D31 acoustic train configuration. The electrical ground connection can be made to the metal ultrasonic waveguide 252, which is electrically conductive, if there is electrical contact between the piezoelectric elements 254a, 254b and the ultrasonic waveguide 252.

In various aspects, as described below, an ultrasonic medical device may comprise a transducer configured to produce longitudinal vibrations, and a surgical instrument having a transducer base plate operably coupled to the transducer, an end effector, and wave guide therebetween. In certain aspects, as also described below, the transducer can produce vibrations which can be transmitted to the end effector, wherein the vibrations can drive the transducer base plate, the wave guide, the end effector, and/or the other various components of the ultrasonic medical device at, or near, a resonant frequency. In resonance, a longitudinal strain pattern, or longitudinal stress pattern, can develop within the transducer, the wave guide, and/or the end effector, for example. In various aspects, such a longitudinal strain pattern, or longitudinal stress pattern, can cause the longitudinal strain, or longitudinal stress, to vary along the length of the transducer base plate, wave guide, and/or end effector, in a sinusoidal, or at least substantially sinusoidal, manner. In at least one aspect, for example, the longitudinal strain pattern can have maximum peaks and zero points, wherein the strain values can vary in a non-linear manner between such peaks and zero points.

In conventional D33 ultrasonic transducer architectures as shown in FIG. 1, a bolt provides compression that acoustically couples the piezoelectric elements rings to the ultrasonic waveguide. The D31 architecture 250 according to one aspect of the present disclosure employs a variety of different techniques to acoustically couple the piezoelectric elements 254a, 254b to the ultrasonic waveguide 252. These techniques are disclosed hereinbelow.

Figure 4A:
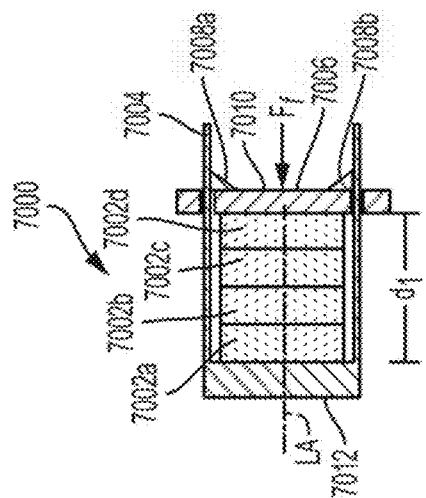
FIGS. 4A-4C illustrate a compressed ultrasonic transducer assembly in a D33 configuration with tuned compression, according to one aspect of this disclosure.
Figure 4B:
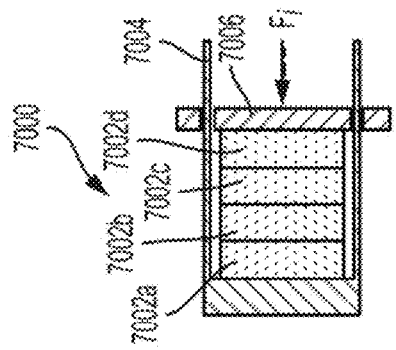
Figure 4C:
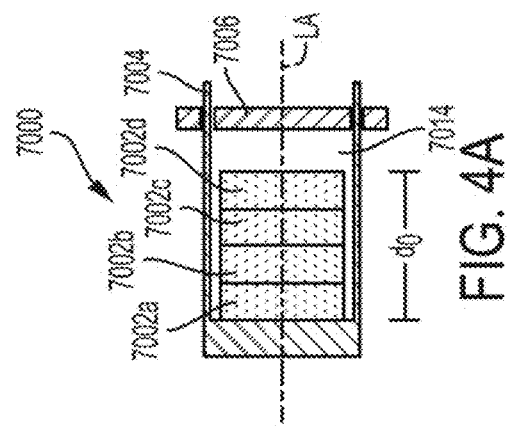

FIGS. 4A-4C illustrate a compressed ultrasonic transducer assembly 7000 in a D33 configuration with tuned compression, according to one aspect of this disclosure. In one aspect, the ultrasonic transducer assembly 7000 includes one or more piezoelectric elements 7002a, 7002b, 7002c, 7002d (e.g., PZT) compressed in an opening 7014 defined by a housing 7004 or shell. Once the ultrasonic transducer assembly 7000 is fully compressed, it is provided to a further assembly process, where, for example, a surface of one of the piezoelectric elements 7002a-d in the assembly 7000 is attached to a metal ultrasonic waveguide or waveguide. Applying compression on the piezoelectric elements 7002a-d (especially in the direction of coupled strain) provides higher efficiency and increased ability to drive larger loads. Because the compressed ultrasonic transducer assembly 7000 does not include an axially compressed element, the piezoelectric elements 7002a-d are compressed along the axis of vibration LA and then anchored in place. The shell 7004 or a band disposed about the piezoelectric elements 7002a-d is compressed and the assembly is anchored in place as described below.

FIG. 4A illustrates an installation phase of the ultrasonic transducer assembly 7000 in a pre-compression state. One or more piezoelectric elements 7002a-d are stacked inside the housing 7004. A plug 7006 is aligned with the piezoelectric elements 7002a-d stack. The housing 7004 and plug 7006 elements are made of a metal material. The plug 7006 and the stack of piezoelectric elements 7002a-d are aligned with the axis of vibration LA. The length of the stack of piezoelectric elements 7002a-d prior to compression is labeled as $d_0$.

FIG. 4B illustrates an initial compression state of the compressed ultrasonic transducer assembly 7000. A targeted initial force $F_i$ is applied to the plug 7006 to compress the plug 7006 onto the stack of piezoelectric elements 7002a-d.

FIG. 4C illustrates a final compression state of the compressed ultrasonic transducer assembly 7000. As shown in FIG. 4C, after a final compression force $F_f$ is applied to the stack of piezoelectric elements 7002a-d, the housing 7004 and the plug are anchored together with anchors 7008a, 7008b while the stack of piezoelectric elements 7002a-d is in the compressed state. The compressed length of the stack of piezoelectric elements 7002a-d is labeled as $d_1$, where $d_1 < d_0$. The anchors 7008a, 7008b may be any suitable element that serves to join the plug 7006 to the housing 7004 firmly in place against the piezoelectric elements 7002a-d to maintain the stack of piezoelectric elements 7002a-d under compression. Accordingly, the anchor 7008a, 7008b may be attached or secured by a joint that is formed by welding, soldering, brazing, epoxy, swaging, or any combination thereof.

In another aspect, the anchor 7008a, 7008b may be attached to the metal housing 7004 by threaded connection. In a threaded connection configuration, the metal housing 7004 and the metal plug 7006 each include a threaded end and the components are threadingly coupled. In one aspect, the metal plug 7006 includes external male threads and the housing 7004 includes internal female threads to threadingly engage the male threads of the plug 7006 and the plug 7006 is screwed into the internal portion of the housing 7004. In another aspect, the plug 7006 includes internal female threads and the housing 7004 includes external male threads to threadingly engage the female threads of the plug 7006 and the plug 7006 is screwed onto the external portion of the housing 7004. In the latter configuration, the inside of the plug 7006 includes a boss or other protruding feature inside the plug 7006 to contact and compress the stack of piezoelectric elements 7002a-c. In the threaded anchor configuration, a rotational force is applied to the plug 7006, which applies a compressed force to the stack of piezoelectric elements 7002a-d as the plug 7006 is threadingly engaged with the housing 7004.

Once the transducer assembly 7000 is fully compressed and the anchors 7008a, 7008b are applied, the transducer assembly 7000 is ready to be assembled. In one aspect, an ultrasonic waveguide is acoustically coupled to a first surface 7010 of the transducer assembly 7000 and in another aspect, the ultrasonic waveguide is acoustically couple to a first surface 7010 of the transducer assembly 7000. In other aspects, the plug 7006 may be a component of an ultrasonic waveguide.

The description now turns to techniques for acoustic coupling ceramic piezoelectric elements to ultrasonic waveguides made of titanium or titanium alloys (i.e., Ti6Al4V) in D31 configurations. Advantages of D31 acoustic coupling techniques described herein include low cost, low profile, ease of manufacture and assembly. Additional advantages include the ability to compress the piezoelectric elements (especially in direction of coupled strain) to provide higher efficiency and drive large loads. In a D31 acoustic train configuration, electrical contacts for electrical connection are provided on both sides of the ceramic piezoelectric elements. An electrical ground connection can applied to the ultrasonic waveguide if there is electrical contact from the ceramic piezoelectric elements to the ultrasonic waveguide. In one aspect, low temperature acoustic coupling techniques are employed to minimize or prevent no damage to the ceramic piezoelectric elements (<150° C.). Electrical connections also may be used as a heat sink. Several techniques for acoustic coupling ceramic piezoelectric elements in D31 configurations to titanium/titanium alloy ultrasonic waveguides are described hereinbelow in connection with FIGS. 5-11.

FIG. 5 is a perspective view of an ultrasonic surgical instrument 7100, according to one aspect of this disclosure. The ultrasonic surgical instrument 7100 includes an ultrasonic transducer 7118 attached to an ultrasonic waveguide 7102 by a bonding material, where the ultrasonic surgical instrument 7100 is configured to operate in a D31 mode. FIG. 6 is perspective view of a piezoelectric element 7104 for use with the ultrasonic surgical instrument 7100 shown in FIG. 5, according to one aspect of this disclosure. The ultrasonic transducer 7118 includes first and second piezoelectric elements 7104a, 7104b attached to opposite sides of the ultrasonic waveguide 7102 by a bonding material. The piezoelectric elements 7104a-b may be PZT ceramic elements attached to a metal ultrasonic waveguide 7102 using a ceramic to metal bonding technique described hereinbelow.

FIG. 7 is section view of the ultrasonic surgical instrument 7100 shown in FIG. 5, according to one aspect of this disclosure. The ultrasonic surgical instrument 7100 includes an ultrasonic transducer attached to an ultrasonic waveguide 7102 by a bonding material, where the ultrasonic surgical instrument 7100 is configured to operate in a D31 mode. The ultrasonic transducer includes a first ceramic piezoelectric element 7104a and a second ceramic piezoelectric element 7104b attached to opposite sides of the ultrasonic waveguide 7102 by a bonding material. The bonding material is used to attach the ceramic to metal connections to bond the ceramic piezoelectric elements 7104a, 7104b to the metal ultrasonic waveguide 7102. In the Example illustrated in FIG. 7, a bottom surface of the top piezoelectric element 7104a is attached to one side of the ultrasonic waveguide 7102 by a metal bonding material such as a metal alloy solder 7106a. Similarly, a bottom surface of the bottom piezoelectric element 7104b is attached to the opposite side of the ultrasonic waveguide 7102 by a metal bonding material such as a metal alloy solder 7106b. The metal alloy solder 7106a, 7106b may be utilized to bond the ceramic piezoelectric elements 7104a, 7104b, which are made of a PZT material (i.e., Pb[Zr$_x$Ti$_{1-x}$]O$_3$), to the metal ultrasonic waveguide 7102, which is made of titanium or titanium alloys (i.e., Ti6Al4V), without using flux or pre-coating the piezoelectric elements 7104a, 7104b. The metal alloy solder may be applied at temperatures below the Curie temperature of the ceramic. The metal alloy solder 7106a, 7106b joint is thermally and electrically conductive, provides a hermetic seal, and has high shear strength. Depending on the joining process, the metal alloy solder 7106a, 7106b, may develop a chemical bond between the surfaces of the piezoelectric elements 7104a, 7104b and the ultrasonic waveguide 7102.

In addition, a metal bonding material such as a metal alloy solder 7108a also may be utilized to bond a thin conductive metal element 7110a to a top surface of the top piezoelectric element 7104a. Similarly, a metal bonding material such as a metal alloy solder 7108b can be utilized to bond a thin conductive metal element 7110b to a top surface of the bottom piezoelectric element 7104b. The conductive metal elements 7110a, 7110b are suitable for making positive electrical connections via soldered wire, crimp connection, or spade connection to the piezoelectric elements 7104a, 7104b. At temperatures below the Curie temperature of the piezoelectric elements 7104a, 7104b, bonding may be performed after poling the piezoelectric elements 7104a, 7104b. At temperatures at or above the Curie temperature of the piezoelectric elements 7104a, 7104b, the piezoelectric elements 7104a, 7104b may be poled after bonding the components of the ultrasonic surgical instrument 7100 as an assembly.

In one aspect, a metal bonding material such as a metal alloy solder 7106a, 7106b, 7108a, 7108b suitable for ceramic to metal bonding may be obtained from S-Bond Technologies, for example. Active metal alloy solders are useful for ceramic to metal bonding. Such solder alloys include active elements such as titanium and cerium added to SnAg, SnInAg, and SnBi alloys to create a solder alloy that can be reacted directly with the ceramic surfaces prior to bonding. Solder alloys produce reliable, hermetic joints with all metals, including steel, stainless steels, titanium, nickel alloys, copper and aluminum alloys, for example. Ceramics are generally not compatible with direct wetting processes (molten metal layers adhering) and ceramics and metals have largely different coefficients of thermal expansion (CTE). Solder alloys, by definition melt and thus join at temperatures below 840° F. and normally closer to 480° F. (250° C.). As such, soldered joints are much better at joining ceramics to metals because the joining stresses are much lower due to solidifying from much lower temperatures than brazed joints. The caveat with conventional solders remains that an adherent metal layer must first be placed on the ceramic surface then followed by a solder flux process to disrupt the oxides that form on the metal and metal coating on the ceramic as they are heated on the solder joining process. The metal alloy solder known under the trade name S-BOND is an active solder suitable for joining metal alloys to ceramics by directly bonding ceramic to metal, forming joints without the use flux and without precoating ceramic steps. This process eliminates multiple step coating processes and can be applied at temperatures below 400° F., preventing distortion and softening of metals and preventing ceramic fracture. The joints produced are hermetic, passing <10$^{-9}$ atm-cc/sec, strong (>5,000 psi shear), ductile, based on SnAg or SnIn alloys and thermally conductive.

The poling axis (P) of the piezoelectric elements 7104a, 7104b is indicated by the direction arrows 7114a, 7114b, respectively. The motion axis of the ultrasonic waveguide 7102 in response to excitation of the piezoelectric elements 7104a, 7104b is shown by the motion arrow 7116 at the distal end of the ultrasonic waveguide 7102 generally referred to as the ultrasonic blade portion of the ultrasonic waveguide 7102. The motion axis 7116 is orthogonal to the poling axis (P) 7114a, 7114b.

FIGS. 8-11 illustrate section views of Example metal alloy solder joints 7106a, 7106b, 7108a, 7108b suitable for ceramic to metal bonding as shown in FIG. 7, according to one aspect of this disclosure. Two different processes can be used in ceramic to metal bonding. A "mechanically activated" joining process shown in FIGS. 8 and 9 can be carried out at or near the metal alloy solder melting temperature, (e.g., 250° C. for S-Bond 220).

Figure 8:
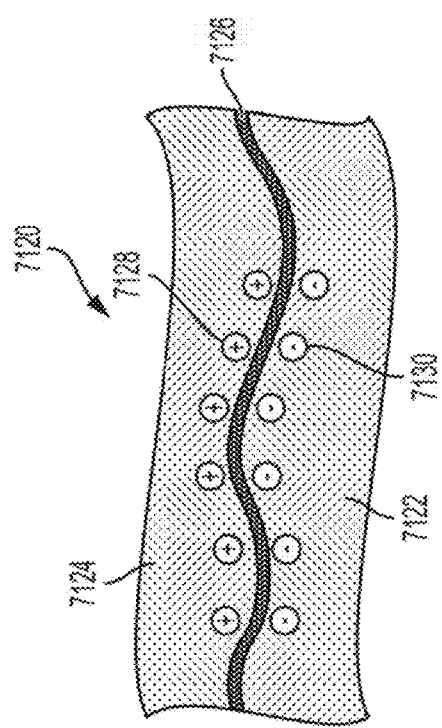
FIG. 8 illustrates an Example of an adhesive bond between a metal and a metal alloy solder, according to one aspect of this disclosure.

FIG. 8 illustrates an Example of an adhesive bond 7120 formed between a metal alloy solder 7122 and a metal 7124, according to one aspect of this disclosure. The bond 7120 can be made by spreading, rubbing, or brushing the molten alloys onto heated surfaces and assembling "hot" in a manner such that the metal alloy solder 7122 surfaces are agitated sufficiently to break the thin oxide skins that form while molten. As shown in FIG. 8, Al, Cr, or Ti atoms 7128 in the metal 7124 and Ti or Ce atoms 7130 in the metal alloy solder 7122 form an adhesive bond at the interface 7126.

Figure 9:
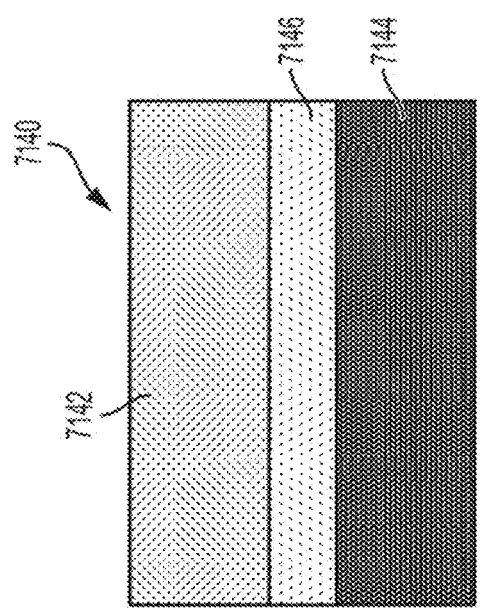
FIG. 9 illustrates an adhesive bond between a ceramic and a metal formed by a metal alloy solder, according to one aspect of this disclosure.

FIG. 9 illustrates an Example of adhesive bond 7140 between a ceramic 7142 (e.g., PZT) and a metal 7144 (e.g., titanium alloy steel) formed by a metal alloy solder 7146. Metal alloy solder 7146 alloys do bond, but the joint strengths are nominally below 3,000 psi in shear. Such joints on ceramics 7142 and many metals 7144 are adhesive, but have no chemical bond.

Figure 10:
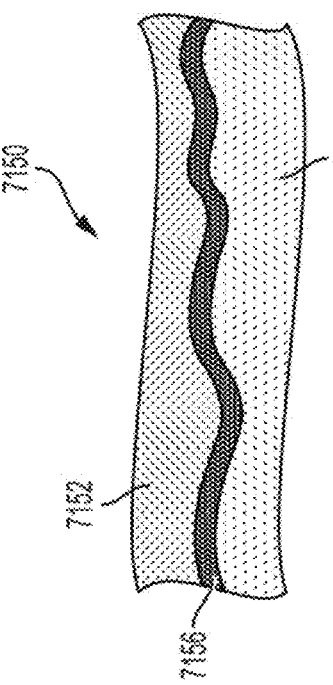
FIG. 10 illustrates an Example of a metallurgical/chemical bond, according to one aspect of this disclosure.

FIG. 10 illustrates an Example of a metallurgical/chemical bond 7150, according to one aspect of this disclosure. Another metal alloy solder 7154 joining process employs a thermally activated process, which prepares the ceramic 7152 surfaces and develops a chemical bond to the surface through reactions of the active elements in the metal alloy solder 7154. These joints start with an elevated temperature treatment in a protective atmosphere furnace with the metal alloy solder 7154 placed on the surfaces of the ceramic 7152 to be joined. At the elevated temperatures, the active elements in the metal alloy solder 7154 react with the ceramic 7152 to develop a chemical bond (e.g., Al(Ti)—Ag phases or Cu—Sn phases) at the interface 7156 between the ceramic 7152 and the metal alloy solder 7154. A chemical bond and a metal alloy solder 7154 layer in a subsequent joining step provides a much higher level of joint strength and creates high performance ceramic metal joints that are better than most brazed sapphire and ceramic to metal joints made by the multistep MoMn and plating processes.

Figure 11:
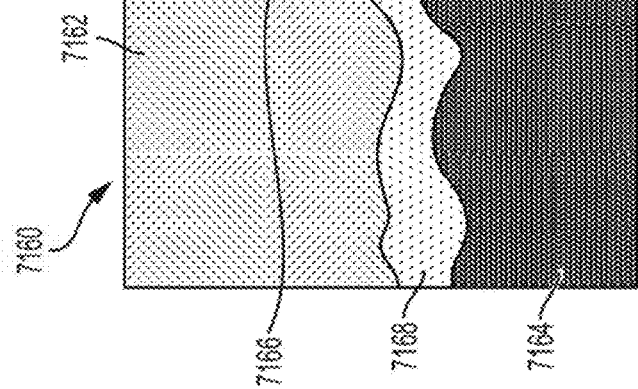
FIG. 11 is a microstructure illustration of a ceramic and metal alloy solder chemical bond, according to one aspect of this disclosure.

FIG. 11 is a microstructure illustration of a ceramic 7164 (e.g., PZT) and metal alloy solder 7162 chemical bond 7160, according to one aspect of this disclosure. A reaction zone 7166 is formed at the ceramic 7164 to metal alloy solder 7162 interface 7168. The S-Bond metal alloy solder provides high joint shear strengths. For example, using elevated temperature S-Bond metal alloy solder metallization procedures, the shear strengths of the chemical bond 7160 at the interface 7168 can exceed 7,000 psi and are resistant to thermal cycling from 50-150° C. The S-Bond metal alloy solder is suitable for joining ceramic and metal surfaces without flux or plating and the process is much more tolerant of joint variations due to the high surface tension of the S-Bond metal alloy solder. The S-Bond metal alloy solder joining process does not use chemical fluxes that must be cleaned up or could etch metallic components, leaving cosmetic defects.

In one aspect, the present disclosure provides a process of acoustic coupling of ceramic piezoelectric elements (e.g., PZT) to a metal (e.g., titanium/titanium alloy) ultrasonic waveguide for use in a D31 configuration. The process further includes making electrical connections to both sides of both piezoelectric elements in the D31 acoustic train configuration. Generally, the process includes soldering ceramic piezoelectric elements to a metal ultrasonic waveguide prior to poling the piezoelectric elements and then poling the assembly. Techniques for bonding ceramic to metal are described above in connection with FIGS. 8-11. In one aspect, the process includes securing ceramic piezoelectric elements (e.g., PZT) to a metal (e.g., titanium/titanium alloy) ultrasonic waveguide via solder paste, reflowing the solder paste to bond the piezoelectric elements to the ultrasonic waveguide, and poling the piezoelectric elements as part of the ultrasonic waveguide/piezoelectric elements assembly. One aspect of this process is described hereinbelow in connection with FIGS. 12A-12C.

Figure 12A:
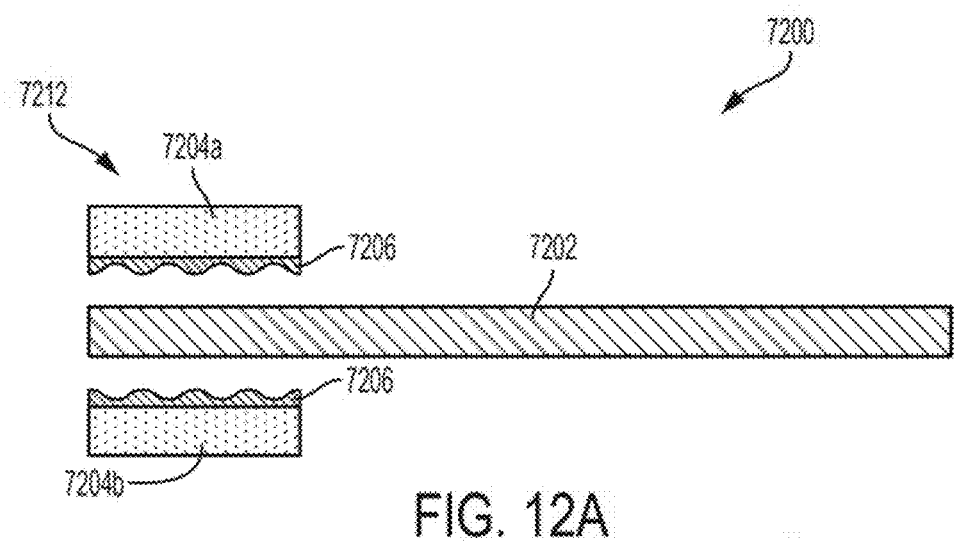
FIG. 12A illustrates an ultrasonic surgical instrument prior to assembly and poling, according to one aspect of this disclosure.
Figure 12B:
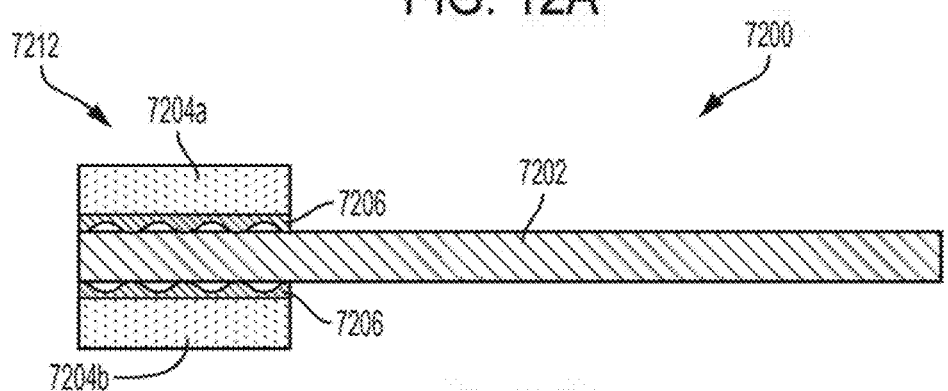
FIG. 12B illustrates the ultrasonic surgical instrument of FIG. 12A prior to poling and the first and second unpoled piezoelectric elements secured to the ultrasonic waveguide in a D31 configuration, according to one aspect of this disclosure.
Figure 12C:
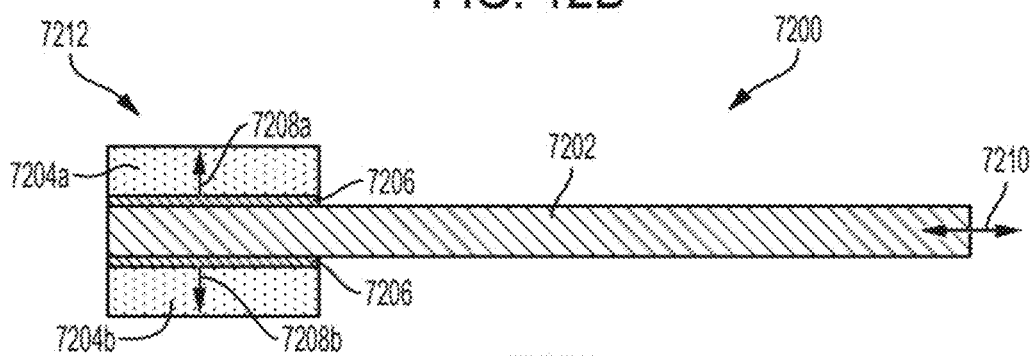
FIG. 12C illustrates the ultrasonic instrument of FIG. 12B prior to poling and the first and second unpoled piezoelectric elements secured to the ultrasonic waveguide in a D31 configuration, according to one aspect of this disclosure.

FIGS. 12A-12C illustrate an ultrasonic surgical instrument 7200 that includes an ultrasonic waveguide 7202 attached to an ultrasonic transducer 7212 by a bonding material, where the ultrasonic surgical instrument 7100 is configured to operate in a D31 mode. The ultrasonic transducer 7212 includes first and second unpoled piezoelectric elements 7204a, 7204b attached to opposite sides of the ultrasonic waveguide 7202 by a bonding material. FIG. 12A illustrates an ultrasonic surgical instrument 7200 prior to assembly and poling, according to one aspect of this disclosure. The ultrasonic surgical instrument 7200 includes a metal ultrasonic waveguide 7202 (e.g., titanium/titanium alloy). A bonding material such as solder paste 7206 is applied to one surface of a first unpoled piezoelectric element 7204a and a second unpoled piezoelectric element 7204b. The solder paste 7206 is a sticky mixture of flux and tiny solder particles, and may be applied to piezoelectric elements 7204a, 7204b with a stainless steel or nickel stencil using a screen printing process. The solder paste 7206 also can be applied to the piezoelectric elements 7204a, 7204b by a jet-printing mechanism, similar to an inkjet printer. After pasting, the piezoelectric elements 7204a, 7204b proceed to a pick-and-place machine or a manual placing process for securing the piezoelectric elements 7204a, 7204b to the ultrasonic waveguide 7202.

FIG. 12B illustrates the ultrasonic surgical instrument 7200 of FIG. 12A prior to poling with the first and second unpoled piezoelectric elements 7204a, 7204b secured to the ultrasonic waveguide 7202 in a D31 configuration, according to one aspect of this disclosure. After pasting, the piezoelectric elements 7204a, 7204b are secured to the ultrasonic waveguide 7202 using an automated or manual process. An insulating clamp may be employed to secure the first and second unpoled piezoelectric elements 7204a, 7204b prior to conveying the secured piezoelectric elements 7204a, 7204b and ultrasonic waveguide 7202 assembly to a reflow soldering oven. Once in the oven, the solder paste 7206 is reflowed to bond the first and second unpoled piezoelectric elements 7204a, 7204b to the ultrasonic waveguide 7202.

FIG. 12C illustrates the ultrasonic instrument 7200 of FIG. 12B after reflow soldering and prior to poling the first and second unpoled piezoelectric elements 7204a, 7204b attached to the ultrasonic waveguide 7202 in a D31 configuration, according to one aspect of this disclosure. Once the secured piezoelectric elements 7204a, 7204b and ultrasonic waveguide 7202 assembly is conveyed to a reflow soldering oven, the solder paste 7206 is reflowed to establish a bond between the first and second unpoled piezoelectric elements 7204a, 7204b and the ultrasonic waveguide 7202. The solder paste 7206 may be reflowed using standard surface mount technology. There are a number of techniques for reflowing the solder 7206. One technique employs infrared lamps and is called infrared reflow. Another technique employs hot gas convection using either standard air or nitrogen gas. Another surface mount technology employs special fluorocarbon liquids with high boiling points which use a method called vapor phase reflow. Each method has its advantages and disadvantages.

After the first and second unpoled piezoelectric elements 7204a, 7204b are attached to the ultrasonic waveguide 7202 using a reflow solder technique, the entire ultrasonic instrument 7200 assembly is poled. A poling process may be carried out in an oil bath with special fixturing. The nature of the piezoelectric effect is closely related to the occurrence of electric dipole moments in solids. The latter may be induced for ions on crystal lattice sites with asymmetric charge surroundings as in piezoelectric elements. The dipole density or polarization (dimensionality $C \cdot m/m^3$) may be calculated for crystals by summing up the dipole moments per volume of the crystallographic unit cell. As every dipole is a vector, the dipole density P is a vector field. Dipoles near each other tend to be aligned in regions called Weiss domains. The domains are usually randomly oriented, but can be aligned using the process of poling (not the same as magnetic poling), a process by which a strong electric field is applied across the material, usually at elevated temperatures. Not all piezoelectric materials can be poled. The poling axis (P) of the piezoelectric elements 7204a, 7204b is indicated by the direction arrows 7208a, 7208b, respectively. The motion axis of the ultrasonic waveguide 7202 in response to excitation of the piezoelectric elements 7204a, 7204b is shown by the motion arrow 7210 at the distal end of the ultrasonic waveguide 7202 generally referred to as the ultrasonic blade portion of the ultrasonic waveguide 7202. The motion axis 7210 is orthogonal to the poling axis (P) 7208a, 7208b.

The piezoelectric effect is the change of polarization P under the application of a mechanical stress. This might either be caused by a reconfiguration of the dipole-inducing surrounding or by re-orientation of molecular dipole moments under the influence of the external stress. Piezoelectricity may manifest in a variation of the polarization strength, its direction or both, with the details depending on: the orientation of P within the crystal; crystal symmetry; and the applied mechanical stress. The change in P appears as a variation of surface charge density upon the crystal faces, i.e., as a variation of the electric field extending between the faces caused by a change in dipole density in the bulk. For example, a 1 $cm^3$ cube of quartz with 2 kN (500 lbf) of correctly applied force can produce a voltage of 12500 V.

Figure 13A:
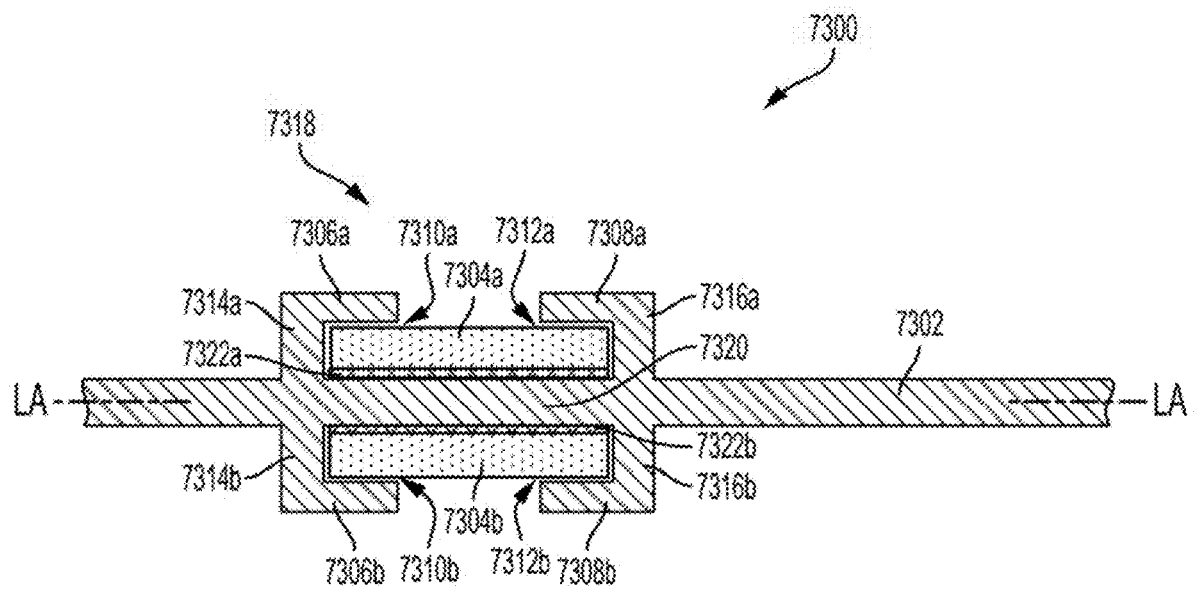
FIG. 13A illustrates an ultrasonic surgical instrument that includes an ultrasonic waveguide configured to hold piezoelectric elements using a bonding material, according to one aspect of this disclosure.

Another technique for acoustic coupling ceramic piezoelectric elements (e.g., PZT) to a metal ultrasonic waveguide (e.g., titanium/titanium alloy) for use in a D31 configuration is described hereinbelow in connection with FIGS. 13A-13C. FIG. 13A illustrates an ultrasonic surgical instrument 7300 that includes an ultrasonic transducer 7318 attached to an ultrasonic waveguide 7302 by a bonding material, where the ultrasonic surgical instrument 7300 is configured to operate in a D31 mode. As shown in FIG. 13A, the ultrasonic surgical instrument 7300 includes an ultrasonic waveguide 7302 configured to hold piezoelectric elements 7304a, 7304b, according to one aspect of this disclosure. The ultrasonic waveguide 7302 includes geometric features to hold the piezoelectric elements 7304a, 7304b. The ultrasonic waveguide 7302 includes a base portion 7320 and a first set of walls 7314a, 7316a extending from one side of the base portion 7320 substantially perpendicular to the longitudinal axis LA. A second set of walls 7314b, 7316b extend from an opposite side of the base portion 7320 substantially perpendicular to the longitudinal axis LA. Ledges 7306a, 7308a project from corresponding walls 7314a, 7316a along the longitudinal axis LA. Ledges 7306b, 7308b project from corresponding walls 7314b, 7316b along the longitudinal axis LA. The ledges 7306a, 7306b, 7308a, 7308b extend over a base portion 7320 of the ultrasonic waveguide 7302 and are substantially parallel to the base portion 7320. In one aspect, the first set of ledges 7306a, 7306b and one side of the base portion 7320 define spaces 7310a, 7310b to receive one end of the piezoelectric elements 7304a, 7304b. The second set of ledges 7308a, 7308b and an opposite side of the base portion 7320 define spaces 7312a, 7312b to receive the other end of the piezoelectric elements 7304a, 7304b.

The ultrasonic transducer 7318 includes first and second piezoelectric elements 7304a, 7304b attached to opposite sides of the base portion 7320 of the ultrasonic waveguide 7302 by a bonding material 7322a, 7322b such as a conductive epoxy, solder, or metal solder alloy. The first piezoelectric element 7304a is slidably received in the first set of spaces 7310a, 7312a. The second piezoelectric element 7304b is slidably received in the second set of spaces 7310b, 7312b.

Once the piezoelectric elements 7304a, 7304b are slidably received in the spaces 7310a, 7310b, 7312a, 7312b, the piezoelectric elements 7304a, 7304b may be attached to the base portion 7320 of the ultrasonic waveguide 7302 using a variety of bonding techniques and bonding materials described above in connection with FIGS. 8-11 or FIGS. 12A-12C.

Figure 13B:
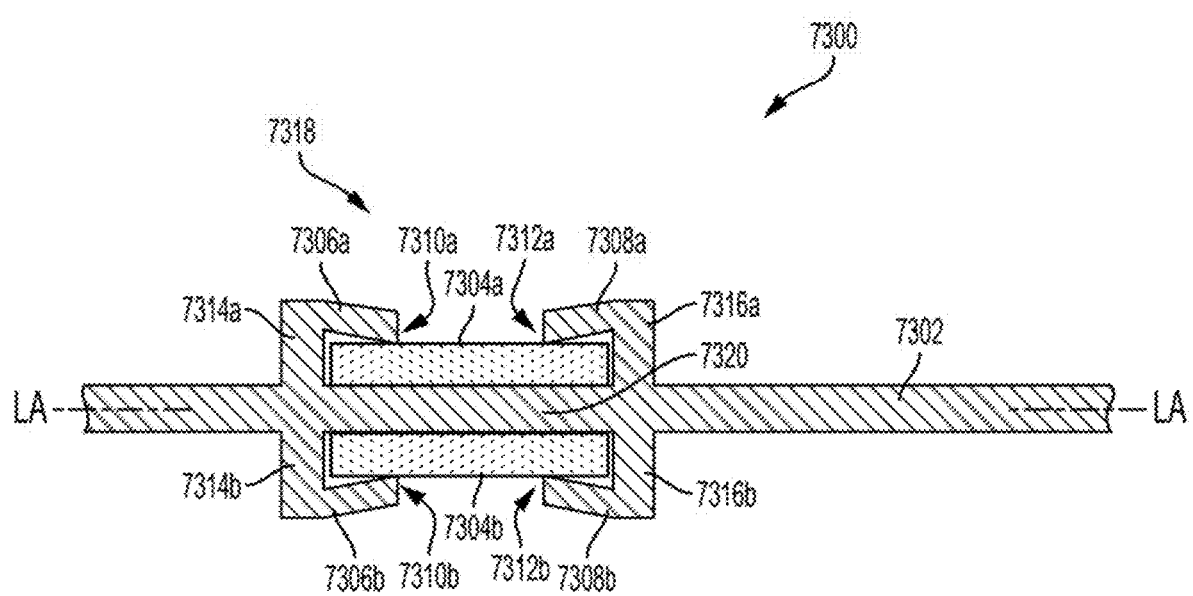
FIG. 13B illustrates an ultrasonic surgical instrument that includes an ultrasonic waveguide configured to hold piezoelectric elements using a biasing force, according to one aspect of this disclosure.

FIG. 13B illustrates an ultrasonic surgical instrument 7330 similar to the ultrasonic surgical instrument 7300 shown in FIG. 13A where the ledges 7306a, 7306b, 7308a, 7308b of the ultrasonic waveguide 7302 are biased, or bent slightly, towards the base portion 7320 of the ultrasonic waveguide 7302 to apply a holding force the piezoelectric elements 7304a, 7304b against the base portion 7320 of the ultrasonic waveguide 7302. The ledges 7306a, 7306b, 7308a, 7308b may be bent before or after the piezoelectric elements 7304a, 7304b are slidably inserted in the spaces 7310a, 7310b, 7312a, 7312b.

Figure 13C:
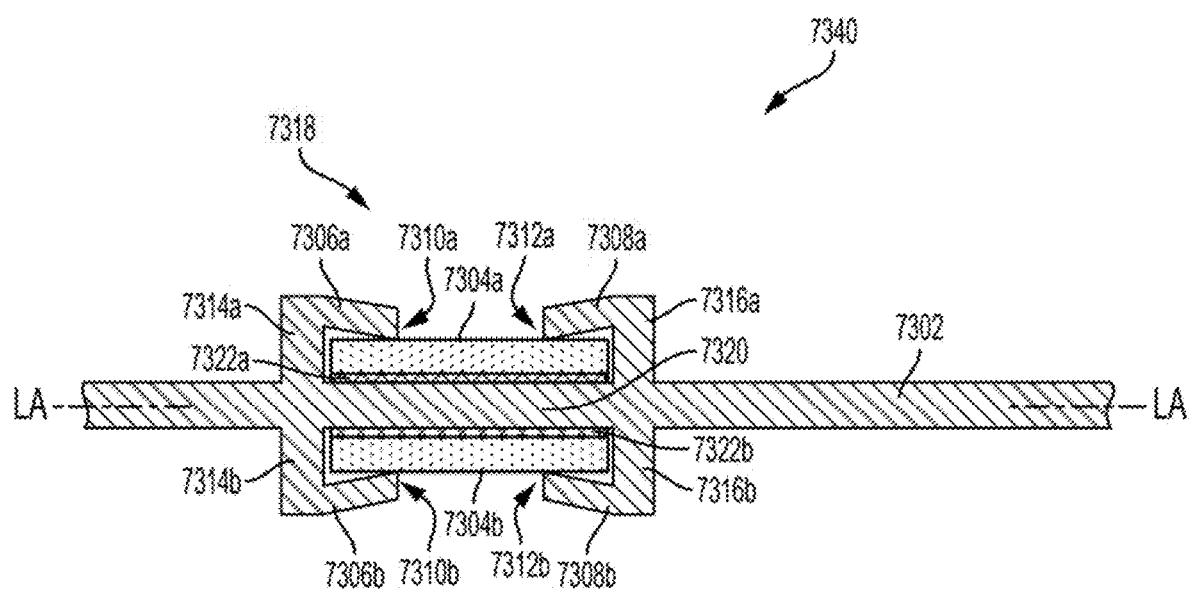
FIG. 13C illustrates an ultrasonic surgical instrument that includes an ultrasonic waveguide configured to hold piezoelectric elements using a combination of a bonding material and a biasing force, according to one aspect of this disclosure.

FIG. 13C illustrates an ultrasonic surgical instrument 7340 similar to the ultrasonic surgical instruments 7300, 7330 shown in FIGS. 13A and 13B, according to one aspect of this disclosure. As shown in FIG. 13C, the piezoelectric elements 7304a, 7304b can be attached to the ultrasonic waveguide 7302 by a combination of applying a bonding material described in connection with FIG. 13A and biasing the ledges 7306a, 7306b, 7308a, 7308b toward the base portion 7320 of the ultrasonic waveguide 7302 to apply a biasing force to the piezoelectric elements 7304a, 7304b as described in connection with FIG. 13B.

Figure 14:
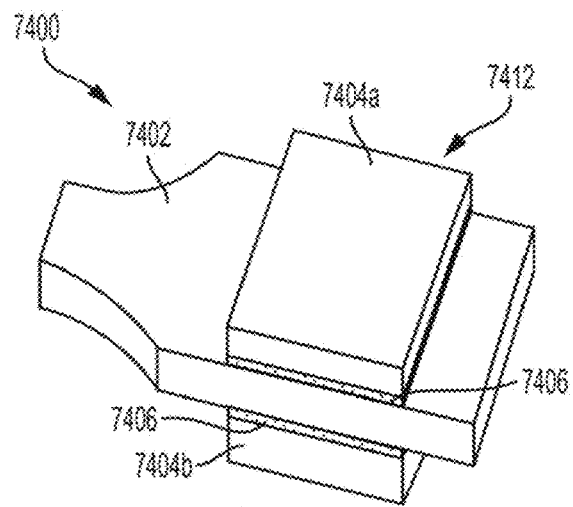
FIG. 14 illustrates an ultrasonic surgical instrument comprising an ultrasonic waveguide fixed to piezoelectric elements arranged in a D31,according to one aspect of this disclosure.
Figure 15:
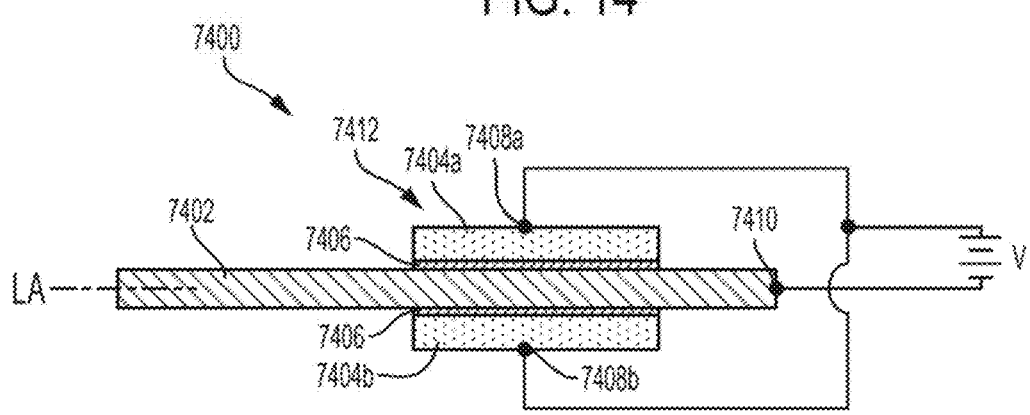
FIG. 15 illustrates the ultrasonic surgical instrument shown in FIG. 14 with a voltage V applied to the piezoelectric elements during a bonding phase, according to one aspect of this disclosure.

In a conventional D33 ultrasonic transducer architecture, the piezoelectric elements (e.g., PZT plates) of an ultrasonic transducer are assembled in a pre-compressed state to ensure that the piezoelectric elements do not operate in tension mode. In a D31 architecture configuration, however, it may be desired to have some pre-compression between each piezoelectric element and the ultrasonic waveguide. FIGS. 14 and 15 illustrate a technique for pre-compressing the piezoelectric elements during a bonding phase of the piezoelectric elements to the ultrasonic waveguide as discussed hereinbelow.

FIG. 14 illustrates an ultrasonic surgical instrument 7400 including an ultrasonic transducer 7412 attached to an ultrasonic waveguide 7402 by a bonding material, where the ultrasonic instrument is configure to operate in a D31 mode, according to one aspect of this disclosure. The ultrasonic transducer 7412 includes first and second piezoelectric elements 7404a, 7404b. FIG. 15 illustrates the ultrasonic surgical instrument 7400 shown in FIG. 14 with a voltage V applied to the piezoelectric elements 7404a, 7404b during a bonding phase, according to one aspect of this disclosure. As shown in FIG. 14, the piezoelectric elements 7404a, 7404b are attached to the ultrasonic waveguide 7402 using a bonding material such as an epoxy adhesive 7406 to bond the piezoelectric elements 7404a, 7404b to the ultrasonic waveguide 7402. In one aspect, pre-compression of the piezoelectric elements 7404a, 7404b may be achieved by applying a voltage to the piezoelectric elements 7404a, 7404b while the epoxy 7406 is curing.

With reference now to FIGS. 14 and 15, accordingly, in a D31 architecture configuration, pre-compression can be obtained between each piezoelectric element 7404a, 7404b and the ultrasonic waveguide 7402 by applying a voltage V to each piezoelectric element 7404a, 7404b during the epoxy 7406 curing process. A positive potential may be applied to electrical connections 7408a, 7408b formed on the free end of each piezoelectric element 7404a, 7404b and a ground potential may be applied to an electrical connection 7410 to the ultrasonic waveguide 7402, for example. As shown in FIG. 15, the voltage V is applied to contract the piezoelectric elements 7404a, 7404b in the direction of the longitudinal axis LA of vibration as described in connection with FIG. 2B, for example. The electrical connections between the ultrasonic waveguide 7402 and the fixed end of the piezoelectric elements 7404a, 7404b may be provided by a conductive epoxy 7406. The piezoelectric elements 7404a, 7404b may be attached to the ultrasonic waveguide 7402 using a variety of bonding materials such as the bonding materials described in connection with FIGS. 8-11 or FIGS. 12A-12C.

In other aspects, in a D31 ultrasonic transducer architecture configuration, the present disclosure provides a method for electrically connecting an energy source to the D31 electrical contacts on both sides of each piezoelectric elements (e.g., PZT plates). The ground connection can be to the ultrasonic waveguide if there is an electrical contact from the piezoelectric elements to the ultrasonic waveguide. In one aspect, the methods are carried out at low temperature to prevent or minimize damage occurs to the piezoelectric elements (<150° C.). The electrical connection may be employed as heat sink. These techniques are described below in connection with FIG. 16.

Figure 16:
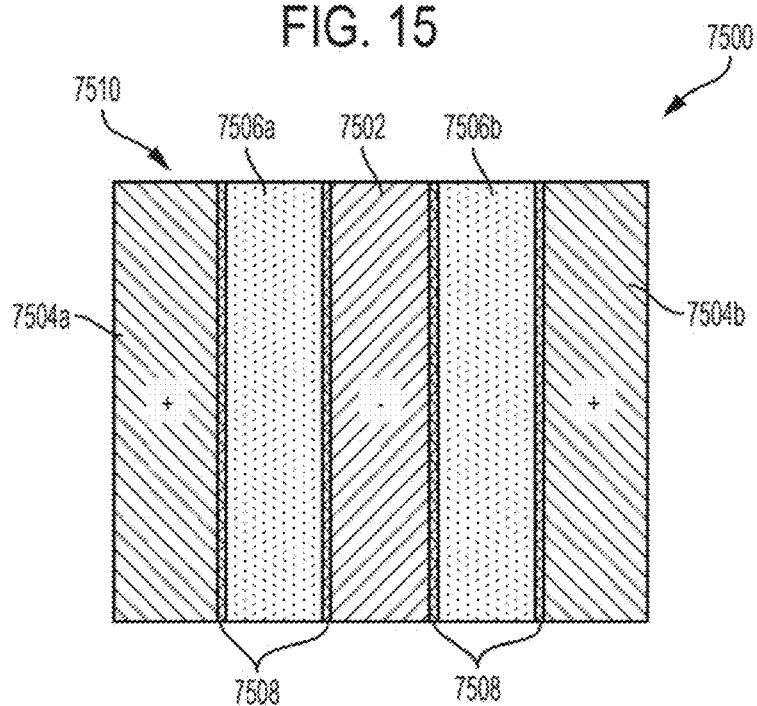
FIG. 16 illustrates a D31 ultrasonic surgical instrument that includes piezoelectric elements attached on one side to an ultrasonic waveguide by a conductive adhesive and attached on another side to electrically conductive plates by a conductive adhesive, according to one aspect of this disclosure.

FIG. 16 illustrates an ultrasonic surgical instrument 7500 including an ultrasonic transducer 7510 attached to an ultrasonic waveguide 7502, by a bonding material, where the ultrasonic surgical instrument 7500 is configured to operate in a D31 mode, according to one aspect of this disclosure. The ultrasonic transducer 7510 includes piezoelectric elements 7506a, 7506b attached on opposite sides of the ultrasonic waveguide 7502 by a bonding material. In one aspect, the bonding material is a conductive adhesive 7508.

Conductive plates 7504a, 7504b are attached to the piezoelectric elements 7506a, 7506b, respectively, by a bonding material such as a conductive adhesive 7508, according to one aspect of this disclosure. An electrical connection method includes soldering the piezoelectric elements 7506a, 7506b on side directly to the inside surfaces of the electrically conductive plates 7504a, 7504b (e.g., copper plates or sheets) and on the other side to the ultrasonic waveguide 7502. A conductive epoxy 7508 is applied between the electrically conductive plates 7504a, 7504b and the free ends of the piezoelectric elements 7506a, 7506b. A conductive epoxy 7508 also is applied between the fixed ends of the piezoelectric elements 7506a, 7506b and the ultrasonic waveguide 7502. Electrically conductive elements such as wires may be connected to the electrically conductive plates 7504a, 7504b and to the ultrasonic waveguide 7502. In one aspect, the ultrasonic waveguide 7502 may be formed by stamping and electrical connection features may be added to the ultrasonic waveguide 7502. The electrically conductive plates 7504a, 7504b may be formed of copper sheets and assembled to female electrical connectors on a cable. Crimp connections may be stamped or formed on the ultrasonic waveguide 7502 and the electrically conductive plates 7504a, 7504b (e.g., copper sheets). The connections to wires may be crimped during assembly. In various aspects, the electrical connection process may include any combination of the above.

Figure 17:
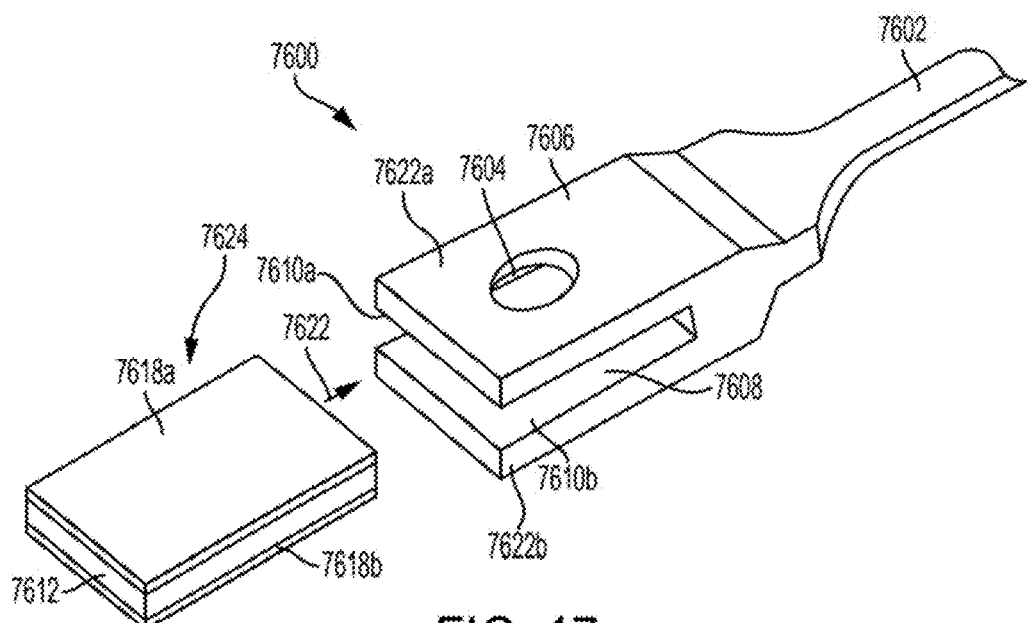
FIG. 17 illustrates an ultrasonic surgical instrument includes a single mid-plane ultrasonic transducer and an ultrasonic waveguide with a tuning-fork-like frame according to one aspect of the present disclosure.
Figure 18:
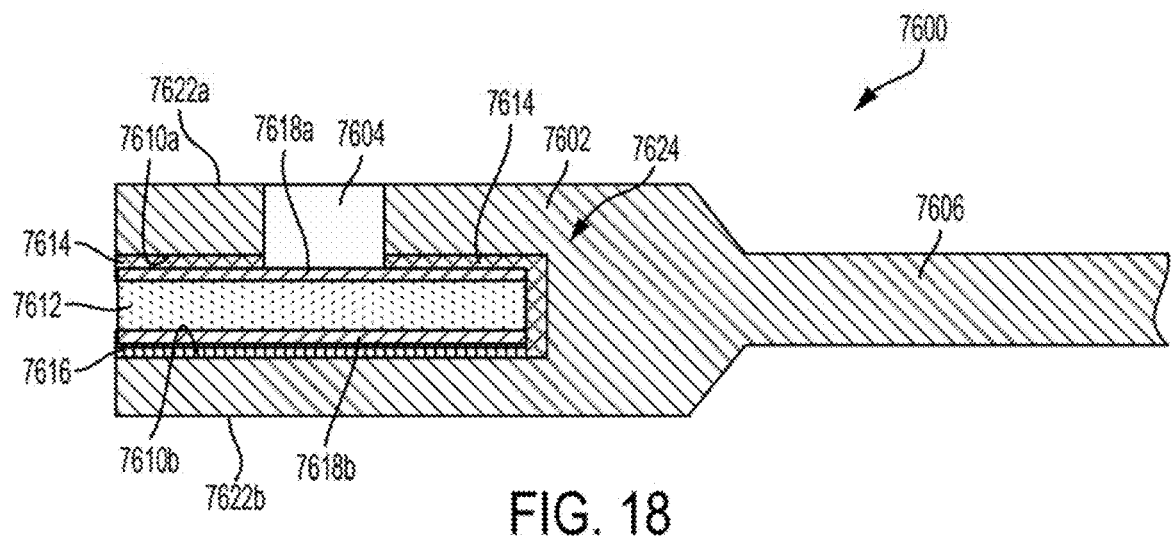
FIG. 18 is a sectional view of the ultrasonic surgical instrument shown in FIG. 17 with the ultrasonic transducer inserted in to the tuning-fork-like frame of the ultrasonic waveguide, according to one aspect of this disclosure.

FIGS. 17 and 18 illustrate an ultrasonic surgical instrument 7600 including an ultrasonic transducer 7624 attached to an ultrasonic waveguide 7602 by a bonding material, where the ultrasonic surgical instrument 7600 is configured to operate in a D31 mode. As shown in FIGS. 17 and 18 the ultrasonic surgical instrument 7600 includes a single midplane ultrasonic transducer 7624 acoustically coupled to an ultrasonic waveguide 7602 includes a tuning-fork-like frame 7606, according to one aspect of the present disclosure. The ultrasonic waveguide 7602 and the tuning-fork-like frame 7606 are made of metal such as titanium or titanium alloys as described throughout this disclosure. The tuning-fork-like frame 7606 includes an upper prong 7622a and a lower prong 7622b defining a U-shaped aperture 7608 therebetween to receive the ultrasonic transducer 7624 therein. In one aspect, the tuning-fork-like frame 7606 configuration constrains top and bottom sides of the ultrasonic transducer 7624 to couple more vibratory energy into the ultrasonic waveguide 7602. The single mid-plane ultrasonic transducer 7624 includes a single piezoelectric element 7612 (e.g., PZT) and electrically conductive plates 7618a, 7618b attached to top and bottom sides of the piezoelectric element 7612 by an electrically conductive bonding material such as a conductive epoxy, solder, or metal solder alloy, for example. The upper prong 7622a of the tuning-fork-like frame 7606 defines an aperture 7604 to provide access for an electrical connection to the top electrically conductive plate 7618a. The ultrasonic transducer 7624 is slidably inserted into the U-shaped aperture 7608 in the direction of arrow 7622 and then fixed therein as shown in FIG. 18.

FIG. 18 is a sectional view of the ultrasonic surgical instrument 7600 shown in FIG. 17 with the ultrasonic transducer 7624 inserted in to the U-shaped aperture 7608 defined by the tuning-fork-like frame 7606 of the ultrasonic waveguide 7602, according to one aspect of this disclosure. Prior to inserting the ultrasonic transducer 7624 into the U-shaped aperture 7608, a first bonding material such as an electrically insulative adhesive 7614 (e.g., electrically insulative conductive epoxy) is applied either to an internal surface 7610a of the upper prong 7622a of the tuning-fork-like frame 7606 or the upper electrically conductive plate 7618a, or both. The electrically insulative adhesive 7614 electrically isolates the tuning-fork-like frame 7606 and the ultrasonic waveguide 7602 from the upper electrically conductive element 7618a. Also, prior to inserting the ultrasonic transducer 7624 into the U-shaped aperture 7608, a second bonding material such as an electrically conductive adhesive 7616 (e.g., electrically conductive epoxy) is applied either to an internal surface 7610b of a lower prong 7622b the tuning-fork-like frame 7606 or the lower electrically conductive plate 7618b, or both. The electrically conductive adhesive 7616 electrically couples the lower electrically conductive plate 7618b to the tuning-fork-like frame 7606 and the ultrasonic waveguide 7602.

Once the ultrasonic transducer 7624 is inserted into the U-shaped aperture 7608, the electrically insulative adhesive 7614 and the electrically conductive adhesive 7616 are cured to bond the ultrasonic transducer 7624 to the tuning-fork-like frame 7606 of the ultrasonic waveguide 7602. One pole of an energy source (e.g., positive) is electrically connected to the upper electrically conductive plate 7618a through the aperture 7604. Another pole of the energy source (e.g., negative or ground) is electrically connected to the ultrasonic waveguide 7602 and the tuning-fork-like frame 7606 and to the lower electrically conductive plate 7618b through the electrically conductive adhesive 7616. In general, the positive pole of the energy source is connected to the upper electrically conductive plate 7618a and the negative pole of the energy source or ground is connected to the ultrasonic waveguide 7602 or tuning-fork-like frame 7606. Nevertheless, configurations where the negative or ground pole of the energy source is connected to the upper electrically conductive plate 7618a and the positive pole of the energy source is connected to the ultrasonic waveguide 7602 or tuning-fork-like frame 7606 are contemplated by this disclosure.

In one aspect, the present disclosure provides a D33 ultrasonic transducer configuration where the metal components are joined by a swaging process. D33 piezoelectric elements are located in a tuning-fork-like metal frame and compressed by a metal plug inserted in the proximal end of the frame. The metal plug is joined to the metal frame by a swaging process. Swaging is a forging process in which the dimensions of an item are altered using dies into which the item is forced. Swaging is usually a cold working process, but also may be hot worked. An assembly fixture applies a compressive force during the swaging process to leave a compressed stress in the stack. The compressive force can be measured by measuring the piezoelectric stack voltage. Another configuration includes a U-frame with an opening provided on a distal end of the U-frame. The piezoelectric stack compression is achieved by inserting the ultrasonic horn/waveguide (e.g., titanium or titanium alloy) into the opening and either swaging or threading the components while the piezoelectric stack is under compression. The frame can be made of a different material than the ultrasonic horn/waveguide, e.g., aluminum. These aspects are described hereinbelow in connection with FIGS. 19-21.

FIGS. 19A and 19B illustrate a D33 ultrasonic transducer 7700 configuration, according to one aspect of this disclosure. In FIG. 19A, a tuning fork-like metal frame 7708 defining a U-shaped aperture 7702 in a proximal end of the metal frame 7708 is provided. The tuning fork-like metal frame 7708 is made of a metal such as titanium or titanium alloy as described herein. As shown in FIG. 19B, a plurality of piezoelectric elements 7706a, 7706b, 7706c, 7706d are inserted into the U-shaped aperture 7702 to form a piezoelectric Langevin stack. A metal plug 7704 is inserted in the proximal end of the tuning fork-like metal frame 7708 until the plug 7704 contacts the piezoelectric stack. An assembly fixture applies compressive forces $FA_1$ from a distal end and a compressive force $FA_2$ from a proximal end to compress the stack of piezoelectric elements 7706a-7706d in the housing 7708. A swaging force FS is applied to the metal plug 7704 to join the metal plug 7704 with the tuning fork-like metal frame 7708 to maintain the piezoelectric elements 7706a-7706d stack under compression.

FIG. 20 illustrates a D33 ultrasonic transducer 7800 configuration, according to one aspect of this disclosure. The ultrasonic transducer 7800 includes a U-shaped metal housing 7802 defining an U-shaped aperture where a plurality of piezoelectric elements 7804a, 7804b, 7804c, 7804d are positioned to form a Langevin stack. An ultrasonic horn/waveguide 7806 is inserted in a distal end of the U-shaped metal housing 7802 until the plug 7806 contacts the piezoelectric elements 7804a-7804d stack. An assembly fixture applies compressive forces $FA_1$ from a distal end and a compressive force $FA_2$ from a proximal end to compress the piezoelectric elements 7804a-7804d in the metal housing 7802 (e.g., aluminum). A swaging force FS is applied to the ultrasonic horn/waveguide 7806 to join the ultrasonic horn/waveguide 7806 to the metal housing 7802 to maintain the piezoelectric elements 7804a-7804d stack under compression.

FIG. 21 illustrates a D33 ultrasonic transducer 7900 configuration, according to one aspect of this disclosure. The ultrasonic transducer 7900 includes a U-shaped metal housing 7902 defining a U-shaped aperture to receive a plurality of piezoelectric elements 7904a, 7904b, 7904c, 7904d in the form of a Langevin stack. The distal end of the U-shaped metal housing 7902 includes female threads 7906 and an ultrasonic horn/waveguide 7910 includes male threads 7908. The ultrasonic horn/waveguide 7910 is threadingly engaged to the U-shaped metal housing 7902. An assembly fixture applies compressive forces $FA_1$ from a distal end a compressive force $FA_2$ from a proximal end to compress the piezoelectric elements 7904a-7904d stack in the housing 7902. A threading FT is applied to the ultrasonic horn/waveguide 7910 to threadingly join the ultrasonic horn/waveguide 7910 to the housing 7902 while the piezoelectric elements 7904a-7904d stack is under compression.

Figure 22A:
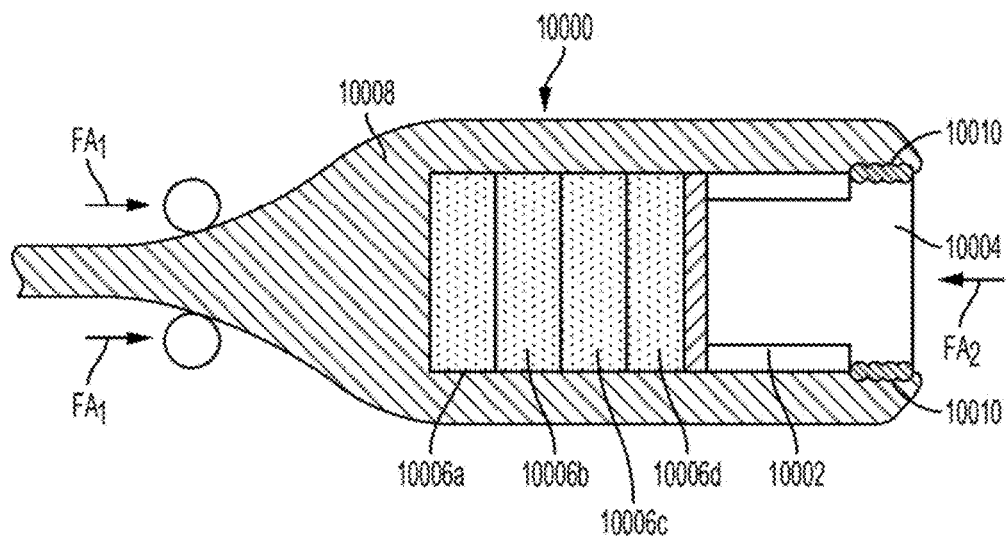
Figure 22B:
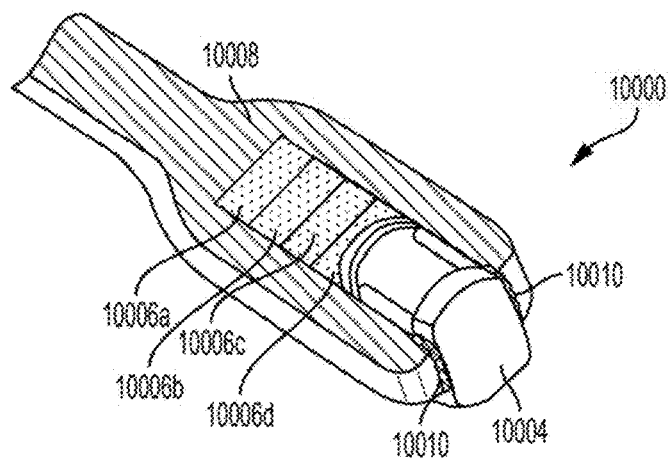
Figure 22C:
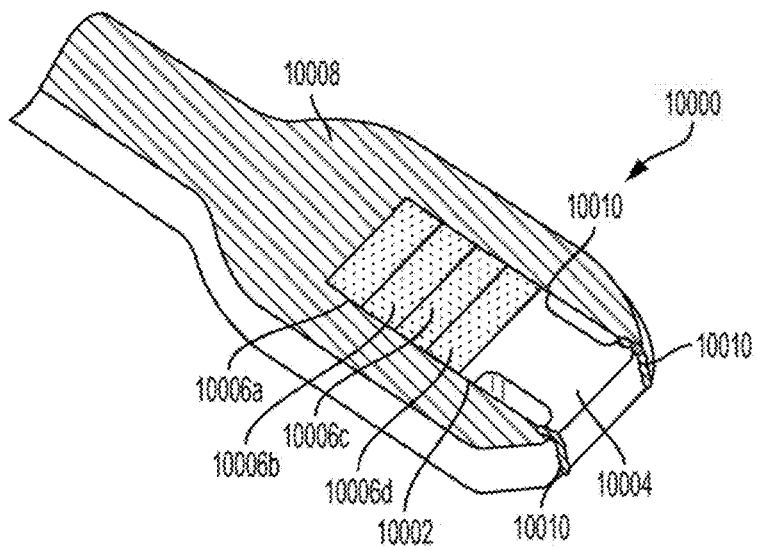
Figure 22D:
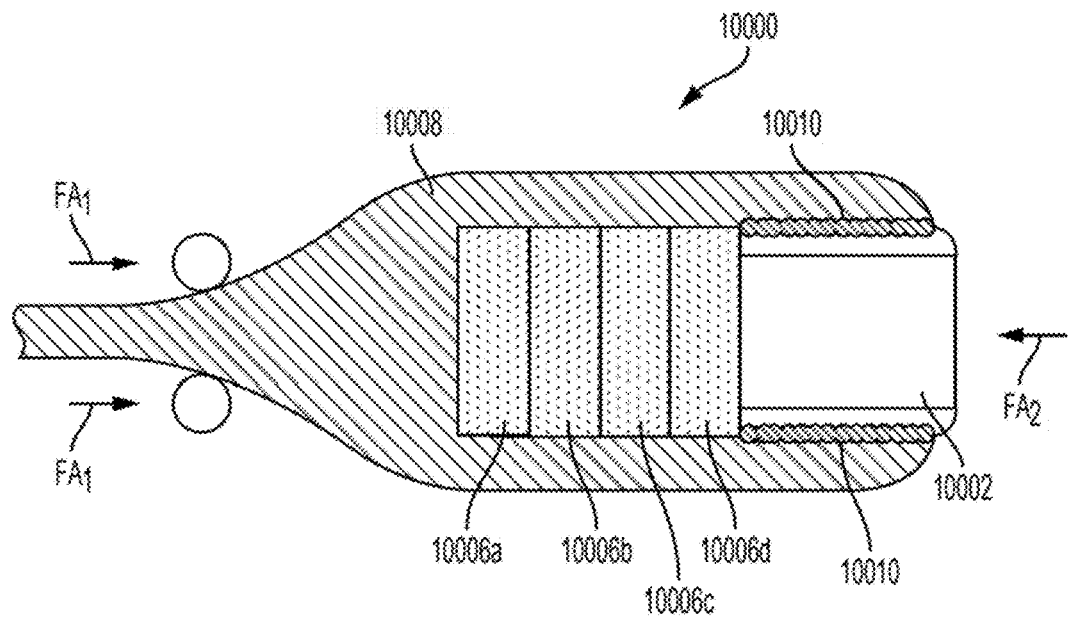

FIGS. 22A-D illustrates a D33 ultrasonic transducer 10000 configuration, according to one aspect of this disclosure. The ultrasonic transducer 10000 includes a U-shaped metal housing 10008 defining an aperture 10002 at the proximal end thereof that is configured to receive a plurality of piezoelectric elements 10006a-d in the form of a Langevin stack. A plug 10004 is inserted in the proximal end of the U-shaped metal housing 10008 until it contacts the stack of piezoelectric elements 10006a-d. The plug 10004 can have a T-shaped configuration as depicted in FIG. 22A, rounded edges as depicted in FIG. 22B, an I-shaped configuration as depicted in FIGS. 22B-C, a rectangular configuration as depicted in FIG. 22D, or any other such suitable configuration. An assembly fixture applies compressive forces $FA_1$ from a distal end and $FA_2$ from a proximal end to compress the piezoelectric elements 10006a-d stack in the housing 10008. Once a desired compressive force is achieved (measured by, e.g., the voltage of the stack of piezoelectric elements 10006a-d), a bond 10010 is applied at the interaction points between the plug 10004 and the housing 10008 while the piezoelectric elements 10006a-d stack is under compression. The assembly fixture can maintain the compressive forces $FA_1$, $FA_2$ until the bond 10010 is sufficiently strong to independently maintain the desired compressive force on the piezoelectric elements 10006a-d stack. The bond 10010 can include, e.g., an adhesive resin or complementary threading, such as is described above with respect to FIG. 21. The bond 10010 can also be achieved through fabrication processes, including, e.g., welding or brazing. If the process for establishing or fabricating the bond 10010 requires a temperature high enough to produce depoling in the piezoelectric elements 10006a-d, then the ultrasonic transducer 10000 can be poled or re-poled after assembly.

FIG. 23 illustrates a D33 ultrasonic transducer 10100 configuration, according to one aspect of this disclosure. The ultrasonic transducer 10100 includes a U-shaped metal housing 10108 defining an aperture at the distal end thereof that is configured to receive a plurality of piezoelectric elements 10106a-d in the form of a Langevin stack. The proximal end 10103 of the ultrasonic waveguide 10102, which defines a plug, is inserted in the distal end of the U-shaped metal housing 10108 until it contacts the stack of piezoelectric elements 10106a-d. An assembly fixture applies compressive forces $FA_1$ from a distal end and $FA_2$ from a proximal end to compress the piezoelectric elements 10106a-d stack in the housing 10108. Once a desired compressive force is achieved (measured by, e.g., the voltage of the stack of piezoelectric elements 10106a-d), a bond 10104 is applied at the interaction points between the ultrasonic waveguide 10102 and the housing 10108 while the piezoelectric elements 10006a-d stack is under compression. The assembly fixture can maintain the compressive forces $FA_1$, $FA_2$ until the bond 10104 is sufficiently strong to independently maintain the desired compressive force on the piezoelectric elements 10106a-d stack. The bond 10104 can include, e.g., an adhesive resin or complementary threading, such as is described above with respect to FIG. 21. The bond 10104 can also be achieved through fabrication processes, including, e.g., welding or brazing. If the process for establishing or fabricating the bond 10104 requires a temperature high enough to produce depoling in the piezoelectric elements 10106a-d, then the ultrasonic transducer 10100 can be poled or re-poled after assembly. The ultrasonic waveguide 10102 can be constructed from the same metal material as the housing 10108 or a different metal material, e.g., aluminum.

FIGS. 24A-C illustrate a D31 ultrasonic transducer 10200 configuration, according to one aspect of this disclosure. The ultrasonic transducer 10200 includes a housing 10202 constructed from a shape-memory alloy, a transducer base plate 10208 (e.g., transducer mounting portion) disposed within the interior of the housing 10202, and an ultrasonic waveguide 10206 extending through a proximal aperture 10210 of the housing 10202. The transducer base plate 10208 comprises flat faces on opposite sides to receive piezoelectric elements. The shape-memory alloy from which the housing 10202 is constructed can include, e.g., CuAlTi and NiTi alloys. In various aspects, the shape-memory alloy of the housing 10202 has a default shape 10212 (i.e., a shape to which the housing 10202 returns when heated) that is smaller than the working shape of the housing 10202 (i.e., the shape at which the housing 10202 is utilized to begin assembly of the ultrasonic transducer 10200), as depicted in FIG. 24C. In one aspect, the default shape 10212 of the housing 10202 is smaller both axially and radially from the working shape of the housing 10202. In alternative aspects, the default shape 10212 can be smaller in any number of dimensions as compared to the working shape of the housing 10202. The dimensions of the default shape 10212 are calculated to correspond to the final desired dimensions of the ultrasonic transducer 10200 wherein all of the components of the ultrasonic transducer 10200 are operably coupled. The housing 10202 can have a variety of shapes such as, e.g., a cylindrical shape.

The housing 10202 includes a plurality of slots 10204*a*, 10204*b* that are configured to receive piezoelectric elements therethrough. In the depicted aspect, the slots 10204*a*, 10204*b* are arranged longitudinally on the housing 10202 and each slot 10204*a*, 10204*b* extends along one side of the transducer base plate 10208 within the housing 10202. A piezoelectric element can be inserted through each of the slots 10204*a*, 10204*b* such that each piezoelectric element is positioned on an opposing side of the transducer base plate in a D31 configuration. In alternative aspects, the slots can vary in number and orientation so that the piezoelectric elements can be placed in alternative configurations within the housing 10202, such as a D33 configuration. Once the piezoelectric elements are situated within the slots 10204*a*, 10204*b*, the ultrasonic transducer 10200 is heated to a temperature that causes the shape-memory alloy of the housing 10202 to return to the default shape 10212, as depicted in FIG. 24C. As the housing 10202 returns to its default shape 10212, it exerts an axial compression force $F_A$ and a radial compression force $F_R$ on the components therein. One effect of the compressive forces $F_A$, $F_R$ is that the piezoelectric elements are brought securely into contact with the transducer base plate 10208 and held in place in a D31 configuration. The piezoelectric elements can thereafter be electrically excited to induce ultrasonic vibrations, as described above. A second effect is that the compressive forces $F_A$, $F_R$ join the ultrasonic waveguide 10206 to the transducer base plate 10208 and securely hold these components in place such that ultrasonic vibrations can be transmitted through the transducer base plate 10208 to the ultrasonic waveguide 10206. Once assembled, this aspect of the D31 ultrasonic transducer 10200 can be utilized in association with, e.g., a surgical instrument. If the process for heating the shape-memory alloy of the housing 10202 requires a temperature high enough to produce depoling in the piezoelectric elements, then the ultrasonic transducer 10200 can be poled or re-poled after assembly.

FIGS. 25A-C illustrate a D33 ultrasonic transducer 10300 configuration, according to one aspect of this disclosure. The ultrasonic transducer 10300 includes a U-shaped metal housing 10308 defining an aperture 10302 at the proximal end thereof that is configured to receive a plurality of piezoelectric elements 10306*a-d* in the form of a Langevin stack. A plug 10304*a* is inserted in the proximal end of the U-shaped metal housing 10308 until it contacts the stack of piezoelectric elements 10306*a-d*. As the plug 10304*a* is inserted into the housing 10308, threading 10312 disposed on the plug 10304*a* engages complementary threading 10310 disposed on the interior surface of the housing 10308, allowing the plug 10304*a* to be securely tightened against the stack of piezoelectric elements 10306*a-d* to exert a compressive force thereagainst. Once a desired compressive force is achieved (measured by, e.g., the voltage of the stack of piezoelectric elements 10306*a-d*), tightening of the plug 10304*a* can be ceased. Once tightened, the engaged threading 10310, 10312 will maintain the plug 10304*a* in position. The piezoelectric elements 10306*a-d* can either be poled prior to assembly of the ultrasonic transducer 10300, or the ultrasonic transducer 10300 can be poled or re-poled after assembly.

FIG. 25D illustrates a D33 ultrasonic transducer 10300 configuration, according to one aspect of this disclosure. In this aspect, the plug 10304*b* includes threading 10316 that engages with complementary threading 10318 of a nut 10314. When the nut 10314 is threadably engaged with the plug 10304*b*, tightening the nut 10304*b* causes the plug 10304*b* to be driven into the interior of the housing 10308 and contact the stack of piezoelectric elements 10306*a-d*, exerting a compressive force thereagainst, as described above. In the depicted aspect, the plug 10304*b* lacks threading that engages with internal threading of the housing 10308. In an alternative aspect, the ultrasonic transducer 10300 can include a combination of the nut 10314 that threadably engages the plug 10304*b* and the plug threading 10312 that engages with internal threading 13310 of the housing 10308, as described above with respect to FIGS. 25A-C.

FIG. 25E illustrates a D33 ultrasonic transducer configuration, according to one aspect of this disclosure. In this aspect, the ultrasonic transducer 10300 includes one or more fasteners 10322*a*, 10322*b* that are configured to extend through the housing 10308 and engage the plug 10304*c* in order to maintain the plug 10304*c* in position. The fasteners 10322*a*, 10322*b* can include, e.g., screws that are configured to threadably engage the plug 10304*c*. The fasteners 10322*a*, 10322*b* can be configured to, e.g., extend longitudinally through from the distal end of the housing 10308 to the proximal end to engage the plug 10304*c*. When the fasteners 10322*a*, 10322*b* are engaged with the plug 10304*c*, tightening the fasteners 10322*a*, 10322*b* causes the plug 10304*c* to contact the stack of piezoelectric elements 10306*a-d* and exert a compressive force thereagainst, as described above. In the depicted aspect, the plug 10304*c* lacks threading that engages with internal threading of the housing 10308. In an alternative aspect, the ultrasonic transducer 10300 can include a combination of the fasteners 10322*a*, 10322*b* engaging the plug 10304*c* and the plug threading 10312 that engages with internal threading 13310 of the housing 10308, as described above with respect to FIGS. 25A-C.

FIGS. 26A-D illustrate a D33 ultrasonic transducer configuration and an assembly process thereof, according to one aspect of this disclosure. The ultrasonic transducer 10400 includes a U-shaped metal housing 10408 defining an aperture 10402 at the proximal end thereof that is configured to receive a plurality of piezoelectric elements 10406*a-d* in the form of a Langevin stack. The housing 10408 further includes a channel 10410 extending longitudinally along each of the opposing surfaces defining the aperture 10402. A plug 10404 includes a pair of tabs 10412*a*, 10412*b* that are configured to slidably engage the channels 10410 extending along the opposing interior sides of the housing 10408. As depicted in FIG. 26A, the plug 10404 is inserted in the proximal end of the U-shaped metal housing 10408, along the channels 10410, until it contacts the stack of piezoelectric elements 10406*a-d*. As depicted in FIG. 26C, an assembly fixture then applies a compressive force $F_1$ to the plug 10404 to compress the piezoelectric elements 10406*a-d* stack in the housing 10008. Once a desired compressive force is achieved (measured by, e.g., the voltage of the stack of piezoelectric elements 10406*a-d*), a second compressive force $F_2$ is applied to the housing 10408 while the piezoelectric elements 10406*a-d* stack is under compression, as depicted in FIG. 26D. The compressive force $F_2$ deforms the channels 10410 (and the tabs 10412*a*, 10412*b* situated therein), locking the plug 10404 in place. The compressive force $F_2$ can be applied by, e.g., a punch press. The piezoelectric elements 10406*a-d* can either be poled prior to assembly of the ultrasonic transducer 10400, or the ultrasonic transducer 10400 can be poled or re-poled after assembly.

FIG. 27 illustrates a D31 ultrasonic transducer 10500 configuration, according to one aspect of this disclosure. The ultrasonic transducer 10500 includes a U-shaped metal housing 10508 defining an aperture 10502 at the proximal end thereof that is configured to receive a transducer base plate 10504 (e.g., a transducer mounting portion) that comprises flat faces on opposite sides to receive the piezoelectric elements 10506*a-b*. The piezoelectric elements 10506*a-b* can be affixed on the transducer base plate 10504 via, e.g., epoxy layer 10518*a-b*. The transducer base plate 10504 has a generally T-shaped configuration, including a longitudinal or axial portion 10512 that terminates at a distal end 10514 and a transverse portion 10510 attached to a proximal end of the axial portion 10512. In one aspect, the piezoelectric elements 10506*a-b* and the axial portion 10512 are dimensioned such that they form a press or interference fit with the interior surface(s) 10524 defining the aperture 10502 when the transducer base plate 10504 is inserted into the aperture 10502. The interference fit compresses the piezoelectric elements 10506*a-b* in an axial and/or radial direction. This pre-compression of the piezoelectric elements 10506*a-b* improves the performance of the ultrasonic transducer 10500. The housing 10508 further includes a slot 10516 that is configured to receive the distal end 10514 of the transducer base plate 10504. In one aspect, the distal end 10514 and the slot 10516 are configured to engage in a press or interference fit. In another aspect, the distal end 10514 is bonded to the slot 10516 via an adhesive resin, fasteners, welding, brazing, a physical deformation joint, or another such securement method. When the transducer base plate 10504 is secured to the housing 10508 in the described manner, ultrasonic vibrations generated by the piezoelectric elements 10506*a-b* are transmitted through the transducer base plate 10504 to the ultrasonic waveguide. The transverse portion 10510 of the transducer base plate 10504 is configured to seal or plug the aperture 10502. In one aspect, one or more surfaces 10520*a-b* of the transverse portion 10510 are fixed to the opposing surfaces 10522*a-b* of the housing 10508 via an adhesive resin, fasteners, welding, brazing, a physical deformation joint, or another such securement method. The piezoelectric elements 10506*a-b* can either be poled prior to assembly of the ultrasonic transducer 10500, or the ultrasonic transducer 10500 can be poled or re-poled after assembly.

FIG. 28 illustrates a D31 ultrasonic transducer 10600 configuration, according to one aspect of this disclosure. The ultrasonic transducer 10600 includes a metal housing 10608 defining one or more recesses 10602 that are each configured to receive a piezoelectric element 10606*a-b* (i.e., piezoelectric element 10606*a* and piezoelectric element 10606*b*) therein. The dimensions of the recesses 10602 are equal to a close tolerance to the dimensions of the piezoelectric elements 10606*a-b*, such that the recesses 10602 hold the piezoelectric elements 10606*a-b* fixed in place when the piezoelectric elements 10606*a-b* are inserted therein. In the depicted aspect, the metal housing 10608 includes a first recess 10602 and a second recess (not shown) disposed on an opposing side from the first recess 10602. Each recess 10602 includes a plurality of 10610 cavities disposed along the sides thereof. Each cavity 10610 is sized and shaped to securely receive a corresponding tab 10604 disposed along the edges of the piezoelectric elements 10606*a-b*. The housing 10608 with the recesses 10602 can be fabricated via, e.g., metal injection molding.

As the dimensions of the recesses 10602 are substantially equal to the dimensions of the piezoelectric elements 10606*a-b* and the tabs 10604 extend beyond the perimeter of the piezoelectric elements 10606*a-b*, the piezoelectric elements 10606*a-b* cannot be inserted into the recesses 10602 under standard conditions. In one aspect of assembling the ultrasonic transducer 10600, the housing 10608 is heated to a temperature that causes the material from which the housing 10608 is constructed to expand and/or be rendered malleable. After the housing 10608 is heated to the appropriate temperature, the piezoelectric elements 10606*a-b* are then inserted into the recesses 10602 so that the tabs 10604 each engage a corresponding cavity 10610. The assembled ultrasonic transducer 10600 is then cooled. In some aspects, the ultrasonic transducer 10600 is additionally compressed as it cools. As the ultrasonic transducer 10600 cools (and optionally undergoes external compression), the recesses 10602 compress around the piezoelectric elements 10606*a-b* therein, causing the tabs 10604 to become secured within the cavities 10610 and thereby fixing the piezoelectric elements 10606*a-b* in place. In aspects wherein the housing 10608 is fabricated utilizing metal injection molding, the piezoelectric elements 10606*a-b* can be inserted into the recesses 10602 prior to the housing 10608 being sintered because the housing 10608 shrinks during the sintering process. Alternatively, the piezoelectric elements 10606*a-b* can be inserted into the recesses 10602 after the housing 10608 has been sintered, but prior to the hot isostatic press step in the metal injection molding process as the housing 10608 shrinks during the hot isostatic press step as well. In an alternative aspect, the piezoelectric elements 10606*a-b*, rather than the housing 10608, is heated to a temperature that renders the piezoelectric elements 10606*a-b* able to be inserted into the recesses 10602. Once the heated piezoelectric elements 10606*a-b* are placed within the recesses 10602, the ultrasonic transducer 10600 is then cooled as described above, with or without external compression. If the process for heating the ultrasonic transducer 10600 requires a temperature high enough to produce depoling in the piezoelectric elements 10606*a-b*, then the ultrasonic transducer 10600 can be poled or re-poled after assembly.

FIGS. 29A-B illustrate a D31 ultrasonic transducer 10700 configuration, according to one aspect of this disclosure. The ultrasonic transducer 10700 includes a metal housing 10708 defining one or more apertures 10702 extending therethrough. In one aspect, the aperture 10702 is extruded through-holes extending across the housing 10708. The aperture 10702 is configured to receive a piezoelectric element 10706 therein. In the depicted aspect, the ultrasonic transducer 10700 comprises a single aperture 10702; however, the ultrasonic transducer 10700 can include any number of apertures 10702 and corresponding piezoelectric elements 10706. The dimensions of the aperture 10702 are equal to a close tolerance to the dimensions of the piezoelectric element 10706, such that the aperture 10702 holds the piezoelectric element 10706 fixed in place when the piezoelectric elements 10706 when inserted therein. The housing 10708 with the aperture(s) 10702 can be fabricated via, e.g., metal injection molding.

In one aspect of assembly the ultrasonic transducer 10700, the housing 10708 is heated to a temperature that causes the material from which the housing 10708 is constructed to expand and/or be rendered malleable. After the housing 10708 is heated to the appropriate temperature, the piezoelectric element 10706 is then inserted into the aperture 10702. The assembled ultrasonic transducer 10700 is then cooled. In some aspects, the ultrasonic transducer 10700 is additionally compressed as it cools. As the ultrasonic transducer 10700 cools (and optionally undergoes external compression), the recesses 10702 compress around the piezoelectric element 10706 therein, fixing the piezoelectric element 10706 in place due to frictional engagements between the surface of the piezoelectric element 10706 and the surface of the aperture 1702. In aspects wherein the housing 10708 is fabricated utilizing metal injection molding, the piezoelectric element 10706 can be inserted into the aperture 10702 prior to the housing 10708 being sintered because the housing 10708 shrinks during the sintering process. Alternatively, the piezoelectric element 10706 can be inserted into the aperture 10702 after the housing 10708 has been sintered, but prior to the hot isostatic press step in the metal injection molding process as the housing 10708 shrinks during the hot isostatic press step as well. In an alternative aspect, the piezoelectric element 10706, rather than the housing 10708, is heated to a temperature that renders the piezoelectric element 10706 able to be inserted into the aperture 10702. Once the heated piezoelectric element 10706 is placed within the aperture 10702, the process of assembling the ultrasonic transducer 10700 is the same as with the aforementioned aspect. If the process for heating the ultrasonic transducer 10700 requires a temperature high enough to produce depoling in the piezoelectric elements 10706, then the ultrasonic transducer 10700 can be poled or re-poled after assembly.

FIGS. 30A-D illustrate D31 ultrasonic transducer 10800 configurations, according to one aspect of this disclosure. The ultrasonic transducer 10800 includes a transducer base plate 10802, a plurality of piezoelectric elements 1806*a-b* bonded to opposing surfaces of the transducer base plate 10802 (e.g., a transducer mounting portion) in a D31 configuration, and a compression plate 10808*a-b* bonded to the exterior surface of each of the piezoelectric elements 1806*a-b*. The various components of the ultrasonic transducer 10800 can be bonded to each other by, e.g., an electrically conductive epoxy adhesive. In the aspect depicted in FIGS. 30A-B, the transducer base plate 10802, piezoelectric elements 1806*a-b*, and compression plates 10808*a-b* include a series of apertures that are configured to align with each other such that a fastener 10804 can be received therethrough when the components are secured together. The fastener 10804 includes, e.g., a screw having a complementary nut 10810. In an alternative aspect depicted in FIGS. 30C-D, only the compression plates 10808*a-b* include a series of apertures that are configured to align with each other such that fasteners 10804*a-b* can be received therethrough when the components are secured together. These fasteners 10804*a-b* can likewise include, e.g., screws having complementary nuts 10810*a-b*. Tightening the fastener(s) 10804 applies additional compressive force to the ultrasonic transducer 10800, which can improve the performance of the ultrasonic transducer 10800. In some aspects, the compression plates 10808*a-b* are constructed from a metal material, which can aid in heat dissipation of the ultrasonic transducer 10800.

FIG. 31 illustrates a D33 ultrasonic transducer 10900 configuration, according to one aspect of this disclosure. The ultrasonic transducer 10900 includes a metal housing 10908 defining an open interior 10902 that is configured to receive a plurality of piezoelectric elements 10906*a-d* (i.e., piezoelectric elements 10906*a*, 10906*b*, 10906*c*, and 10906*d*) in the form of a Langevin stack. The ultrasonic transducer 10900 further includes a threaded plug or threaded rod 10904 extending through a threaded aperture 10912 disposed at the proximal end of the housing 10908 into the housing interior 10902. As the threaded rod 10904 is tightened, the distal end 10910 thereof contacts the stack of the piezoelectric elements 10906*a-d* and applies a compressive force to compress the piezoelectric elements 10906*a-d* stack in the housing 10908. Once a desired compressive force is achieved, the threaded rod 10904 will be maintained in the particular tightened position due to its engagement with the threaded aperture 10912. The degree of compressive force applied by the threaded rod 10904 can be adjusted by loosening or tightening the threaded rod 10904 in order to tune the frequency of the stack of piezoelectric elements 10906*a-d*, without the need to disassemble the ultrasonic transducer 10900. In some aspects, the ultrasonic transducer 10900 can switch between operating frequencies according to the degree of applied compressive force on the stack of piezoelectric elements 10906*a-d*. When the ultrasonic transducer 10900 is utilized in conjunction with a surgical instrument, being able to switch between operating frequencies in the field can allow for the ultrasonic transducer 10900 to adjust to tissue effects encountered by the surgical instrument or to different end effector types.

FIGS. 32A-B illustrate D31 ultrasonic transducer 11000 configurations having multiple pairs of piezoelectric elements, according to one aspect of this disclosure. The ultrasonic transducer 11000 includes a first transducer array 11002*a* disposed on a first face of the transducer base plate 11008 (e.g., a transducer mounting portion) and a second transducer array 11002*b* disposed on a second face, which opposes the first face, of the transducer base plate 11008. In the aspect depicted in FIG. 32A, the transducer arrays 11002*a-b* are arranged in a D31 configuration. Each of the transducer arrays 11002*a-b* includes a first piezoelectric element 11006*a* and a second piezoelectric element 11006*b* arranged adjacently to each other. In the depicted aspect, the piezoelectric elements 11006*a-b* are arranged longitudinally with respect to the longitudinal axis of the transducer base plate 11008. In other aspects, the piezoelectric elements 11006*a-b* are arranged in other orientations, such as orthogonally, relative to the transducer base plate 10008. In some aspects, the piezoelectric elements 11006*a-b* of the opposing transducer arrays 11002*a-b* are arranged in matching pairs. In other words, each of the piezoelectric elements 11006*a-b* of the first transducer array 10002*a* is aligned with a corresponding piezoelectric element of the second transducer array 11002*b*. In the depicted aspect, the piezoelectric elements 11006*a-b* are rectangular in shape and the transducer array 11002*a* is square in shape.

In the aspect depicted in FIG. 32B, the transducer array 11002*c* includes a first piezoelectric element 11006*c*, a second piezoelectric element 11006*d*, a third piezoelectric element 11006*e*, and a fourth piezoelectric element 11006*f* arranged adjacently to each other. In one aspect, the piezoelectric elements 11006*c-f* are arranged symmetrically along both the x and y axes of the planar transducer array 11002*c*. In the depicted aspect, the piezoelectric elements 11006*c-f* are square in shape and the transducer array 11002*c* is likewise square in shape.

In various aspects, the transducer arrays 11002*a-c* depicted in FIGS. 32A-B can be utilized in combination with or in lieu of each other, or other arrays of piezoelectric elements. The piezoelectric elements 11006*a-f* in the segmented transducer arrays 11002*a-c* can each be driven individually, thereby allowing the transducer arrays 11002*a-c* to produce unbalanced vibrations. In previously discussed aspects where the piezoelectric elements on the opposing faces of the transducer base plate 11008 are balanced with respect to each other, non-longitudinal motion of the waveguide and/or end effector is undesired. However, segmented transducer arrays 11002a-c that can be selectively activated in an asymmetric or non-balanced manner can produce two desirable effects. First, if there is unwanted vibration or flexure in the surgical system, then the segmented transducer arrays 11002a-c can be selectively activated in order to counterbalance undesired lateral vibrations and return the system to producing stable, longitudinal motion. Second, in some cases lateral or torsional movement of the end effector is desired. Therefore in these cases, the segmented transducer arrays 11002a-c can be selectively activated in an asymmetric manner in order to induce the desired non-longitudinal movement at the end effector. The activation of the piezoelectric elements 11006a-f in the transducer arrays 11002a-c can be controlled, e.g., by controlling the amount of electrical current applied to the individual piezoelectric elements 11006a-f.

FIGS. 33A-C illustrate D31 ultrasonic transducer 11100, 11200, 11300 configurations having asymmetrically excitable piezoelectric transducer assemblies 11102, 11202, 11302, according to one aspect of this disclosure. As discussed above with respect to FIGS. 32A-B, it can be advantageous for ultrasonic transducers to be able to produce unbalanced or asymmetric vibrations in certain cases, such as for counteracting undesired non-longitudinal vibrations within the surgical system or to intentionally induce non-longitudinal movement at the end effector. In some aspects, asymmetry can be achieved by having the piezoelectric elements arranged asymmetrically relative to the longitudinal axis of the ultrasonic waveguide. In other aspects, asymmetry can be achieved by having the piezoelectric elements arranged symmetrically relative to the longitudinal axis of the ultrasonic waveguide, but selectively activatable in an asymmetric manner. In aspects where the ultrasonic transducers are capable of generating both symmetrical or asymmetrical vibrations depending upon the selective activation of the piezoelectric elements consisting the transducer array, the surgical systems incorporating the ultrasonic transducers can be configured to interchangeably switch between the symmetric and asymmetric activation modes by reversibly activating (i.e., electrically exciting) or deactivating the individual piezoelectric elements.

FIG. 33A illustrates a D31 ultrasonic transducer 11100 configuration including a transducer base plate 11108 (e.g., a transducer mounting portion) comprising flat faces on opposite sides to receive piezoelectric elements 11106a-c thereon. The piezoelectric elements 11106a-c are sized, shaped, and arranged asymmetrically about the longitudinal axis of the waveguide 11104. The first piezoelectric element 11106a and the third piezoelectric element 11106c are roughly triangular in shape and the second piezoelectric element 11106b is irregular in shape. In this aspect, the first piezoelectric element 11106a and the second piezoelectric element 11106b are configured to generate a symmetrical vibration about the longitudinal axis of the waveguide 11104. Likewise, the first piezoelectric element 11106a and the third piezoelectric element 11106c are configured to generate a symmetrical vibration about the longitudinal axis of the waveguide 11104. However, activation of all three piezoelectric elements 11106a-c or activation of the second piezoelectric element 11106b and the third piezoelectric element 11106c is configured to generate an asymmetrical vibration due to the sizes, shapes, and arrangements of the piezoelectric elements 11106a-c.

FIG. 33B illustrates a D31 ultrasonic transducer 11200 configuration including a transducer base plate 11208 (e.g., a transducer mounting portion) comprising flat faces on opposite sides to receive piezoelectric elements 11206a-c thereon. The piezoelectric elements 11206a-c are sized, shaped, and arranged symmetrically about the longitudinal axis of the waveguide 11204, but can be selectively activated to generate asymmetrical vibrations. Specifically, either activation of all three piezoelectric elements 11206a-c or activation of the first piezoelectric element 11206a and the third piezoelectric element 11206c are configured to generate symmetrical vibrations. Conversely, activation of the second piezoelectric element 11206b and one of the first piezoelectric element 11206a or the third piezoelectric element 11206c is configured to generate asymmetrical vibrations.

FIG. 33C illustrates a D31 ultrasonic transducer 11300 configuration including a transducer base plate 11308 (e.g., a transducer mounting portion) comprising flat faces on opposite sides to receive piezoelectric elements 11306a-c thereon. The piezoelectric elements 11306a-c are sized and shaped equivalently to each other, but are arranged asymmetrically about the longitudinal axis of the waveguide 11304. Activation of the first piezoelectric element 11306a and the second piezoelectric element 11306b is configured to generate symmetrical vibrations; however, activation of any other combination of the piezoelectric elements 11306a-c is configured to generate asymmetrical vibrations.

It should be noted that FIGS. 32A-33C are merely exemplary and a variety of other configurations of segmented ultrasonic transducer arrays configured to generate symmetrical vibrations, asymmetrical vibrations, or a combination of symmetrical vibrations or asymmetrical vibrations are contemplated. Furthermore, the descriptions of various aspects of ultrasonic transducer arrays incorporating 2, 3, and 4 piezoelectric elements are merely exemplary. The teachings herein are likewise applicable to ultrasonic transducer arrays incorporating more than 4 piezoelectric elements. Still further, in various aspects the piezoelectric elements of the ultrasonic transducer arrays may be activated synchronously, asynchronously, or with a variety of ultrasound activation signals that may differ in frequency, phase, or amplitude.

FIGS. 34A-B illustrate a D31 ultrasonic transducer 11400 configuration wherein the piezoelectric elements 11406a-b are offset relative to each other, according to one aspect of this disclosure. The ultrasonic transducer 11400 includes a transducer base plate 11408 (e.g., a transducer mounting portion), a first piezoelectric element 11406a disposed on a first face of the transducer base plate 11408, and a second piezoelectric element 11406b disposed on a second face opposing the first face. The first piezoelectric element 11406a and the second piezoelectric element 11406b are longitudinally offset from each. In one aspect, each of the piezoelectric elements 11406a-b are positioned at a node of the acoustic assembly on the transducer base plate 11408. A node is a minimum or zero crossing in the vibratory motion standing wave (i.e., where motion is usually minimal). Therefore, the piezoelectric elements 11406a-b are offset from each other by a distance equal to a one-half wavelength ($\lambda/2$) of the acoustic assembly.

In aspects of ultrasonic transducers incorporating piezoelectric elements that are arranged in an aligned manner (i.e., are not offset from each other) on the transducer base plate 11408, the ultrasonic transducers generate half waves. Conversely, arranging the piezoelectric elements 11406a-b such that they are offset by a one-half wavelength ($\lambda/2$) of the acoustic assembly causes the ultrasonic transducer 11400 to generate a full wave. A full wave vibratory motion can be utilized to introduce non-longitudinal motion to an end effector driven by the acoustic assembly. The ultrasonic transducer 11400 can additionally incorporate one or more balancing features configured to balance or compensate for the bending motion or flexure mode induced by the full wave generated by the offset piezoelectric elements 11406a-b. If additional balancing features are utilized to compensate for the offset piezoelectric elements 11406a-b, the ultrasonic transducer 11400 induces a longitudinal motion at the end effector, as depicted in FIG. 34C. If balancing features are not utilized to compensate for the piezoelectric elements 11406a-b, the ultrasonic transducer 11400 induces a non-longitudinal or bending motion at the end effector, as depicted in FIG. 34D. In some aspects, the balancing features can be selectively activatable, allowing a surgical instrument incorporating the ultrasonic transducer 11400 to switch between longitudinal and non-longitudinal modes for the end effector.

It should be noted that the teachings of any aspect of an ultrasonic transducer assembly depicted as a specific transducer architecture, e.g., a D31 transducer architecture or a D33 transducer architecture, are equally applicable to ultrasonic transducers utilizing other configurations, unless stated otherwise or if such a teaching would be in conflict with the structure of the particular transducer architecture. For example, the teachings of an aspect of an ultrasonic transducer assembly depicted as a D31 transducer architecture, such as in FIGS. 19A-23, 25A-26D, and 31, are likewise applicable to a D33 transducer assembly, such as in FIGS. 24A-C, 27-30D, and 32A-34B, and vice versa (unless they would be in conflict with the structure of the particular transducer architecture).

Figure 35B:
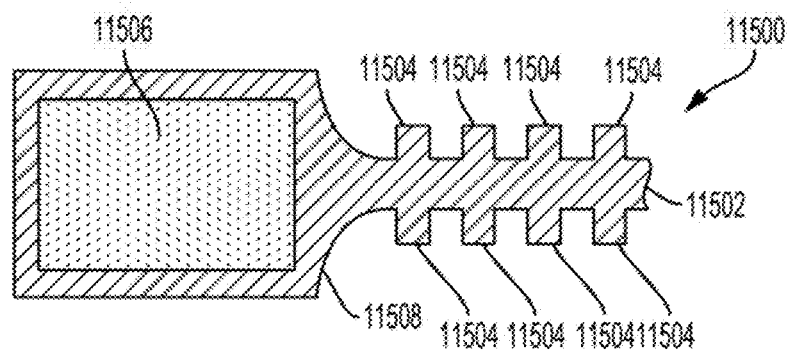
Figure 35C:
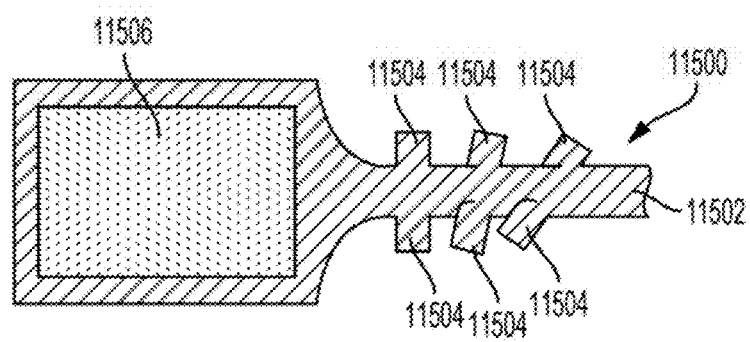
Figure 35D:
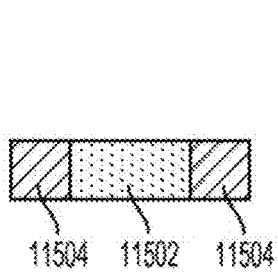
Figure 35E:
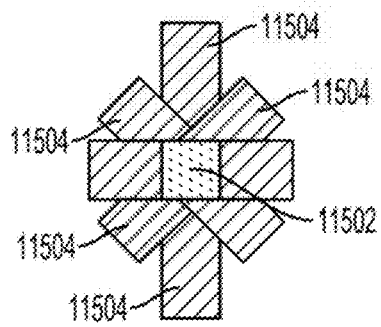

FIGS. 35A-E illustrate various views of a surgical tool 11500 including of a waveguide 11508 of a surgical instrument having complex features and a fabrication process thereof, according to one aspect of this disclosure. The surgical tool 11500 comprises a proximal transducer base plate 11506 (e.g., a transducer mounting portion), a distal end effector 11502, and a longitudinal portion or waveguide 11508 extending therebetween. In various aspects, the waveguide 11508 further comprises a plurality of teeth 11504 disposed along its length. Furthermore, in various aspects the waveguide 11508 is twisted such that the teeth 11504 extend from the longitudinal axis of the waveguide 11508 at a variety of different angles, as depicted in FIG. 35E.

In order to fabricate the surgical instrument 11500, the first step is to fabricate a flat plate surgical tool 11500 comprising a plurality of teeth 11504, as depicted in FIGS. 35B and 35D. The surgical tool 11500 can be fabricated via a variety of manufacturing processes including, e.g., metal injection molding. The teeth 11504 can be formed on the surgical instrument 11500 via the metal injection molding process or via, e.g., forming, machining, cutting, forging, grinding, polishing, de-burring, tumbling, or any other such manufacturing process. Next, the waveguide 11508 is gradually twisted, as depicted in FIG. 35C. The waveguide 11508 can be twisted via a variety of manufacturing processes including, e.g., passing the waveguide 11508 through a series of progressive dies. The twisting may also be used to adjust various features of the waveguide 11508, such as curvature, offset, flex section, and thin or tapered tissue clamping sections. The waveguide 11508 can be twisted at any point along its length. In one aspect, the waveguide is twisted such that the teeth 11504 are symmetrically offset from each other (i.e., adjacent teeth 11504 are angularly separated by a fixed amount). In this aspect, the angularly symmetric teeth 11504 generate both a longitudinal motion and a torsional (i.e., non-longitudinal) motion at the end effector 11502.

FIGS. 36A-D illustrate various views of a D31 ultrasonic transducer 11600 configuration configured to generate non-longitudinal motion and components thereof, according to one aspect of this disclosure. The ultrasonic transducer 11600 includes a metal housing 11608 including a recess 11602 (see FIG. 36A) configured to receive a cylindrical piezoelectric element 11604 therein (see FIGS. 36C, 36D). The ultrasonic transducer 11600 further comprises a cylindrical transducer support 11610 (see FIGS. 36B, 36C) configured to support the cylindrical element 11604 thereon and a plurality of electrodes 11612a-c (see FIG. 36C) arranged about the piezoelectric element 11604. In one aspect, the electrodes 11612a-c are angularly offset from each other by a fixed amount (i.e., the electrodes 11612a-c angularly symmetric). The piezoelectric element 11604 can be affixed to the transducer support 11610 by, e.g., a conductive epoxy. The transducer support 11610 can be affixed to the interior sidewalls of the recess 11602, thereby supporting the piezoelectric element 11604 and electrodes 11612a-c within the recess. In various aspects, each of the electrodes 11612a-c is asymmetric or unbalanced about at least one axis (i.e., x, y, or z), thereby causing each of the electrodes 11612a-c to have a net mass offset. When the ultrasonic transducer 11600 is in use, the angularly offset electrodes 11612a-c that are asymmetrically weighted cause the ultrasonic transducer 11600 to induce both a longitudinal motion and a torsional (i.e., non-longitudinal) motion at the end effector of the surgical instrument.

FIG. 37 illustrates a perspective view of an electrical connector 11700 to an ultrasonic signal generator for a surgical instrument, according to one aspect of this disclosure. Various surgical instruments, such as ones disclosed in U.S. patent application Ser. No. 15/679,967 entitled "TISSUE LOADING OF A SURGICAL INSTRUMENT," now U.S. Patent Application Publication No. 2018/0078268 which is herein incorporated by reference in its entirety, include an electrical connector 11700 that is connectable to an ultrasonic signal generator for driving the piezoelectric elements. The electrical connector 11700 includes a base structure 11710 that supports a first wire 11706a and a second wire 11706b disposed on an interior side 11704 of the base structure 11710, which is configured to be enclosed within the housing of the surgical instrument, and a first pin 11708a and a second pin 11708b disposed on the exterior side 11702 of the base structure 11710 that are configured to be connected to an ultrasonic signal generator. The first wire 11706a and the second wire 11706b are electrically connected to the piezoelectric elements of the ultrasonic transducer and transmit the signal generated by the ultrasonic signal generator thereto.

The interior side 11704 of the electrical connector 11700 is intended to be sealed from the surrounding environment to avoid the ingress of moisture, microbes, and other contaminants that can damage the function of the surgical instrument or otherwise be safety risks for operators and/or patients. If contaminants enter the housing of the surgical instrument, it can be desirable to have the surgical instrument generate an alarm or alert, cease functioning, or perform some other action to notify operators of the instrument that an error has occurred. In this aspect, the electrical connector 11700 comprises a first conductive pathway 11712a and a second conductive pathway 11712b extending along the interior side 11704 of the electrical connector 11700 from the first wire 11706a and the second wire 11706b, respectively. The conductive pathways 11712a-b can include, e.g., soldered channels. The conductive pathways 11712a-b extend towards each other, but terminate such that they are separated by a gap that is sufficiently large to prevent arcing therebetween, but small enough such that a relatively small amount of water can bridge the gap. In one aspect, the gap between the conductive pathways 11712a-b is filled with a hydrophilic coating 11714, as depicted in FIG. 37. In another aspect, the geometry of the electrical connector 11700 is configured to channel fluid to the gap between the conductive pathways 11712a-b (e.g., the interior side 11704 is constructed as a curved surface with a local or global minimum situated at the gap). In either aspect, if fluid enters the housing of the surgical instrument, it is funneled or attracted to the gap between the conductive pathways 11712a-b. When fluid reaches the gap, it causes a short in the electrical system. In one aspect, the short causes the surgical instrument to cease functioning. Therefore, the surgical instrument is prevented from being used if its internal housing is contaminated with moisture. In another aspect, the short causes the circuit of the surgical instrument to generate an error signal, which can in turn be detected and cause an alert or alarm to be generated.

FIGS. 38-41 illustrate various views of a D33 ultrasonic transducer 11800 configuration, according to one aspect of this disclosure. The ultrasonic transducer 11800 includes a metal housing 11808 defining an open interior 11802 that is configured to receive a plurality of piezoelectric elements 11806a-f in the form of a Langevin stack. The housing 11816 includes a connector 11816 that is configured to receive an ultrasonic waveguide. The ultrasonic transducer 11800 further includes a threaded plug or threaded rod 11804 extending through a threaded aperture 11814 disposed at the proximal end of the housing 11808 into the housing interior 11802. The ultrasonic transducer 11800 still further includes a plate 11812 situated between the stack of piezoelectric elements 11806a-f and the distal end 11810 of the threaded rod 11804. As the threaded rod 11804 is tightened, the distal end 11810 thereof contacts the plate 11812 and applies a compressive force to compress the piezoelectric elements 11806a-f stack in the housing 11808. In various aspects, the plate 11812 is constructed from an electrically conductive material.

Once a desired compressive force is achieved, the threaded rod 11804 will be maintained in the particular tightened position due to its engagement with the threaded aperture 11814. The degree of compressive force applied by the threaded rod 11804 can be adjusted by loosening or tightening the threaded rod 11804 in order to tune the frequency of the stack of piezoelectric elements 11806a-f, without the need to disassemble the ultrasonic transducer 11800. In some aspects, the ultrasonic transducer 11800 can switch between operating frequencies according to the degree of applied compressive force on the stack of piezoelectric elements 11806a-d. When the ultrasonic transducer 11800 is utilized in conjunction with a surgical instrument, being able to switch between operating frequencies in the field can allow for the ultrasonic transducer 11800 to adjust to tissue effects encountered by the surgical instrument or to different end effector types.

The ultrasonic transducer 11800 further includes a first wire 11818 and a second wire 11820 that are electrically coupled to the stack of piezoelectric elements 11806a-f. The first wire 11818 can be utilized to deliver a first electrical potential and the second wire 11820 can be utilized to deliver a second electrical potential. In one aspect, the first electrical potential is positive and the second electrical potential is ground or negative. In one aspect, the connection points 11822a-c of the first wire 11818 and the connection points 11824a-d of the second wire 11820 are attached at the junctions between the plate 11812 and each of the piezoelectric elements 11806a-f, which may be connected by, e.g., a conductive adhesive. The connection points 11822a-c of the first wire 11818 and the connection points 11824a-d of the second wire 11820 can be arranged such that they alternate with each other. In one aspect, the connection points 11824a-d of the second wire 11820, representing the negative or ground connection, can be situated at the external connection points 11824a, 11824d of the stack of piezoelectric elements 11806a-f.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although various aspects have been described herein, many modifications and variations to those aspects may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered examples:

Example 1. A compressed ultrasonic transducer assembly, comprising: a metal housing defining an opening; at least two piezoelectric elements disposed within the opening and compressed by a compressive force, wherein the at least two piezoelectric elements are configured to work in a D33 mode; and a metal plug joined to the metal housing to close the opening and to maintain the at least two piezoelectric elements in a compressed state within the metal housing.

Example 2. The compressed ultrasonic transducer assembly of Example 1, further comprising a welded joint to join the metal plug to the metal housing.

Example 3. The compressed ultrasonic transducer assembly of Example 1 or Example 2, further comprising an epoxy joint to join the metal plug to the metal housing.

Example 4. The compressed ultrasonic transducer assembly of one or more of Example 1 through Example 3, wherein the metal housing and the metal plug each comprise a threaded end and the metal housing and the metal plug are threadingly coupled.

Example 5. The compressed ultrasonic transducer assembly of one or more of Example 1 through Example 4, further comprising a swaged joint to join the metal plug to the metal housing.

Example 6. The compressed ultrasonic transducer assembly of one or more of Example 1 through Example 5, wherein the metal housing has a fork-like metal frame.

Example 7. An ultrasonic surgical instrument, comprising: an ultrasonic waveguide; an ultrasonic transducer mounted to the ultrasonic waveguide and configured to operated in a D31 mode, ultrasonic transducer comprising: a first ceramic piezoelectric element having a first side attached to a first side of the ultrasonic waveguide by a first bonding material; and a second ceramic piezoelectric element having a first side attached to a second side of the ultrasonic waveguide by the first bonding material, wherein the first side of the ultrasonic waveguide is opposite the second side of the ultrasonic waveguide.

Example 8. The ultrasonic surgical instrument of Example 7, further comprising: a first electrically conductive plate attached to a second side of the first ceramic piezoelectric element by a second bonding material; and a second electrically conductive plate attached to a second side of the second ceramic piezoelectric element by the second bonding material.

Example 9. The ultrasonic surgical instrument of Example 7 or Example 8, wherein the first bonding material is the same as the second bonding material.

Example 10. The ultrasonic surgical instrument of one or more of Example 8 through Example 9, wherein the first bonding material is a solder bonding material and the second bonding material is a conductive epoxy bonding material.

Example 11. The ultrasonic surgical instrument of one or more of Example 8 through Example 10, wherein the solder is a metal solder alloy bonding material.

Example 12. The ultrasonic surgical instrument of one or more of Example 7 through Example 11, wherein the first bonding material is a solder bonding material.

Example 13. The ultrasonic surgical instrument of Example 12, wherein the solder material is a metal solder alloy bonding material.

Example 14. The ultrasonic surgical instrument of one or more of Example 7 through Example 13, wherein the first ceramic piezoelectric element has a poling axis in a direction from the first side to the second side of the first ceramic piezoelectric element and the second ceramic piezoelectric element has a poling axis in a direction from the first side to the second side of the second ceramic piezoelectric element to operate in a D31 mode.

Example 15. The ultrasonic surgical instrument of Example 14, wherein a motion axis of the ultrasonic waveguide is orthogonal to the poling axes of the first and second ceramic piezoelectric elements.

Example 16. The ultrasonic surgical instrument of one or more of Example 14 through Example 15, wherein the first and second piezoelectric elements are unpoled prior to bonding to the respective first and second sides of the ultrasonic waveguide and are poled after the first and second piezoelectric elements are bonded to the respective first and second sides of the ultrasonic waveguide.

Example 17. An ultrasonic surgical instrument, comprising: an ultrasonic waveguide comprising: a base portion; first and second walls extending from one side of the base portion; and first and second ledges projecting from the corresponding first and second walls, wherein a first space is defined between the first ledge and the base portion and wherein a second space is defined between the second ledge and the base portion; and an ultrasonic transducer attached to the ultrasonic waveguide, wherein the ultrasonic transducer comprises at least one piezoelectric element slidably disposed between the first and second spaces and fixed therein.

Example 18. The ultrasonic surgical instrument of Example 17, wherein the at least one piezoelectric element is attached to the base portion of the ultrasonic waveguide by a bonding material.

Example 19. The ultrasonic surgical instrument of Example 17 or Example 18, wherein the first and second ledges are biased toward the base portion of the ultrasonic waveguide to attach the at least one piezoelectric element to the base portion of the ultrasonic waveguide.

Example 20. The ultrasonic surgical instrument of one or more of Example 17 through Example 19, wherein the at least one piezoelectric element is attached to the base portion of the ultrasonic waveguide by a bonding material, and wherein the first and second ledges are biased toward the base portion of the ultrasonic waveguide to attach the at least one piezoelectric element to the base portion of the ultrasonic waveguide in combination with the bonding material.

Example 21. The ultrasonic surgical instrument of one or more of Example 17 through Example 20, wherein the ultrasonic waveguide further comprises third and fourth walls extending from an opposite side of the base portion; third and fourth ledges projecting from the corresponding third and fourth walls, wherein a third space is defined between the third ledge and the base portion and wherein a fourth space is defined between the fourth ledge and the base portion.

Example 22. The ultrasonic surgical instrument of Example 21, wherein the ultrasonic transducer further comprises a second piezoelectric element slidably disposed between the third and fourth spaces and fixed therein.

Example 23. The ultrasonic surgical instrument of Example 22, wherein the second piezoelectric element is attached to the base portion of the ultrasonic waveguide by a bonding material.

Example 24. The ultrasonic surgical instrument of one or more of Example 22 through Example 23, wherein the third and fourth ledges are biased toward the base portion of the ultrasonic waveguide to attach the second piezoelectric element to the base portion of the ultrasonic waveguide.

Example 25. The ultrasonic surgical instrument of one or more of Example 22 through Example 24, wherein the second piezoelectric element is attached to the base portion of the ultrasonic waveguide by a bonding material, and wherein the third and fourth ledges are biased toward the base portion of the ultrasonic waveguide to attach the second piezoelectric element to the base portion of the ultrasonic waveguide in combination with the bonding material.

Example 26. An ultrasonic surgical instrument, comprising: an ultrasonic waveguide; and an ultrasonic transducer attached to the ultrasonic waveguide; wherein the ultrasonic waveguide comprises a tuning-fork-like frame comprising: an upper prong; and a lower prong defining a U-shaped aperture therebetween configured to receive the ultrasonic transducer therein.

Example 27. The ultrasonic instrument of Example 26, wherein the upper prong of the tuning-fork-like frame defines an aperture to provide access for an electrical connection to the ultrasonic transducer.

Example 28. The ultrasonic instrument of Example 26 or Example 27, wherein the ultrasonic transducer comprises: a piezoelectric element; a first electrically conductive plate attached to a top side of the piezoelectric element by an electrically conductive bonding material; and a second electrically conductive plate attached to a bottom top side of the piezoelectric element by an electrically conductive bonding material.

Example 29. The ultrasonic instrument of Example 28, further comprising: an electrically insulative bonding material disposed between the first electrically conductive plate and an internal surface of the upper prong; and an electrically conductive bonding material disposed between the second electrically conductive plate and an internal surface of the lower prong.

The invention claimed is:

1. An ultrasonic transducer assembly, comprising:
a metal waveguide comprising a first flat side and a second flat side opposite the first flat side;
a first ceramic piezoelectric element and a second ceramic piezoelectric element, the first ceramic piezoelectric element attached to the metal waveguide on the first flat side by a first bonding material and the second ceramic piezoelectric element attached to the metal waveguide on the second flat side by the first bonding material, wherein the first and second ceramic piezoelectric elements are configured to work in a D31 mode;
wherein the first ceramic piezoelectric element has a poling axis in a direction from the first flat side of the metal waveguide to a side of the first ceramic piezoelectric element opposite the first flat side, and the second ceramic piezoelectric element has a poling axis in a direction from the second flat side to a side of the second ceramic piezoelectric element opposite the second flat side, to operate in the D31 mode; and
wherein the ultrasonic transducer assembly is manufactured such that the first and second ceramic piezoelectric elements are unpoled prior to bonding to the respective first and second sides of the metal waveguide and are poled after the first and second ceramic piezoelectric elements are bonded to the respective first and second sides of the metal waveguide.

2. The ultrasonic transducer assembly of claim 1, further comprising:
a first electrically conductive plate attached to a second side of the first ceramic piezoelectric element by a second bonding material; and
a second electrically conductive plate attached to a second side of the second ceramic piezoelectric element by the second bonding material.

3. The ultrasonic transducer assembly of claim 2, wherein the first bonding material is the same as the second bonding material.

4. The ultrasonic transducer assembly of claim 2, wherein the first bonding material is a solder bonding material and the second bonding material is a conductive epoxy bonding material.

5. The ultrasonic transducer assembly of claim 4, wherein the solder bonding material is a metal solder alloy bonding material.

6. The ultrasonic transducer assembly of claim 1, wherein the first bonding material is a solder bonding material.

7. The ultrasonic transducer assembly of claim 6, wherein the solder bonding material is a metal solder alloy bonding material.

8. The ultrasonic transducer assembly of claim 1, wherein a motion axis of the metal waveguide is orthogonal to the poling axes of the first and second ceramic piezoelectric elements.

9. The ultrasonic transducer assembly of claim 1, wherein the first bonding material is a metal alloy solder, and wherein the first ceramic piezoelectric element is bonded to the metal waveguide using the metal alloy solder in an adhesive bonding process.

10. The ultrasonic transducer assembly of claim 1, wherein the first bonding material is a metal alloy solder, and wherein the first ceramic piezoelectric element is bonded to the metal waveguide using the metal alloy solder in a metallurgical/chemical bonding process.

* * * * *